(12) United States Patent
Campos-Neto et al.

(10) Patent No.: US 7,968,694 B2
(45) Date of Patent: Jun. 28, 2011

(54) TUBERCULOSIS ANTIGEN DETECTION ASSAYS AND VACCINES

(75) Inventors: Antonio Campos-Neto, Westborough, MA (US); Suely S. Kashino, Boston, MA (US)

(73) Assignee: Forsyth Dental Infirmary for Children, Cambridge, MA (US)

( * ) Notice: Subject to any disclaimer, the term of this patent is extended or adjusted under 35 U.S.C. 154(b) by 0 days.

(21) Appl. No.: 11/478,366

(22) Filed: Jun. 29, 2006

(65) Prior Publication Data

US 2007/0036816 A1    Feb. 15, 2007

Related U.S. Application Data

(60) Provisional application No. 60/696,439, filed on Jul. 1, 2005, provisional application No. 60/717,062, filed on Sep. 14, 2005.

(51) Int. Cl.
*C07H 21/04* (2006.01)
*C07H 21/02* (2006.01)
*A61K 39/04* (2006.01)

(52) U.S. Cl. ............. 536/23.7; 536/23.1; 536/24.3; 536/24.32; 530/300; 530/350; 424/9.2; 424/184.1; 424/190.1; 424/234.1; 424/248.1

(58) Field of Classification Search .......... 424/9.2, 424/184.1, 190.1, 234.1, 248.1; 435/4, 6; 530/300, 350; 536/23.1, 23.7, 24.3, 24.32
See application file for complete search history.

(56) References Cited

U.S. PATENT DOCUMENTS

| 6,183,957 B1 * | 2/2001 | Cole et al. .................. 435/6 |
| 6,294,328 B1 * | 9/2001 | Fleischmann et al. ........ 435/6 |
| 7,026,465 B2 | 4/2006 | Skeiky et al. |
| 7,064,195 B2 | 6/2006 | Skeiky et al. |

FOREIGN PATENT DOCUMENTS

| WO | WO 02/48175 A2 | 6/2002 |
| WO | WO 03/004520 A2 | 1/2003 |

OTHER PUBLICATIONS

Mukherjee S, et al.,"Potential serological use of a recombinant protein that is a replica of a *Mycobacterium tuberculosis* protein found in the urine of infected mice" *Clin Diagn Lab Immunol*. 11(2):280-6 (2004).

Liu, C. et al., "Expression and purification of immunologically reactive DPPD, a recombinant *Mycobacterium tuberculosis* skin test antigen, using *Mycobacterium smegmatis* and *Escherichia coli* host cells" *Can J Microbiol*. Feb;50(2):97-105 (2004).

Grobusch, Martin P. et al., "Rapid Immunochromatographic Assay for Diagnosis of Tuberculosis, Letter to the Editor" *J Clin. Microb*. 36(11):3443 (1998).

Mukherjee S. et al. "Alternative approach to express *Mycobacterium tuberculosis* proteins in *Escherichia coli*." *Biotechniques* Jul;35(1):34-6, 38, 40. (2003).

Mukherjee S. et al. "Cloning of the gene encoding a protective *Mycobacterium tuberculosis* secreted protein detected in vivo during the initial phases of the infectious process." *J Immunol*. Oct 15;175(8):5298-305 (2005).

Fleischmann R.D. et al. "Whole-genome comparison of *Mycobacterium tuberculosis* clinical and laboratory strains." Journal of Bacteriology. 184(19):5479-5490, (Oct. 2002).

Database Uniprot Phosphoribosylglycinamide formyltransferase 2, Acc. No. P95197, (May 1, 1997).

Flyer D. C. et al. "Identification by mass spectrometry of CD8+-T-cell *Mycobacterium tuberculosis* epitopes within the Rv 0341 product." Infection and Immunity, American Society for Microbiology. Washington, US. 70(6):2926-2932, (Jun. 2006).

* cited by examiner

*Primary Examiner* — Rodney P. Swartz
(74) *Attorney, Agent, or Firm* — Antoinette G. Giugliano, PC; AGG Intellectual Property Law

(57) ABSTRACT

The present invention relates to isolated Tuberculosis (TB) antigens that are useful in therapeutic and vaccine compositions for stimulating a TB specific immunological response. The identified antigens are also useful in diagnostic assays to determine the presence of active TB in an individual. Accordingly, the present invention includes polypeptide molecules, nucleic acid molecules, vaccine compositions, diagnostic assays, and methods of diagnosis and monitoring treatment related to these TB antigens.

18 Claims, 24 Drawing Sheets

Protein Sequence

SEQ ID NO: 2 - DGYVGAPAH

>MT0401
MIDGWTEEQHEPTVRHERPAAPQDVRRVMLLGSAEPSRELAIALQGLGAEVIAV
DGYVGAPAHRIADQSVVVTMTDAEELTAVIRRLQPDFLVTVTAAVSVDALDAVEQADGECTELV
PNARAVRCTADREGLRRLAADQLGLPTAPFWFVGSLGELQAVAVHAGFPLLVSPVAGVAGQG
SSVVAGPNEVEPAWQRAAGHQVQPQTGGVSPRVCAESVVEIEFLVTMIVVCSQGPNGPLI
EFCAPIGHRDADAGELESWQPQKLSTAALDAAKSIAARIVKALGGRGVFGVELMINGDEV
YFADVTVCPAGSAWVTVRSQRLSVFELQARAILGLAVDTLMISPGAARVINPDHTAGRAA
VGAAPPADALTGALGVPESDVVIFGRGLGVALATAPEVAIARERAREVASRLNVPDSRE
(SEQ ID NO: 4)

DNA Sequence

SEQ ID NO: 1 - GACGGCTATGTCGGCGCGCCTGCCCAC

>MT0401
GTGATCGACGGCTGGACGGAAGAACAGCACGAACCCACCGTTAGGCATGAGCGCCCAGCA
GCTCCCCAAGACGTTCGGCGGGTGATGTTGCTGGGTTCGGCCGAACCCAGCCGGGAGCTG
GCGATCGCGTTGCAGGGCTTGGGCGCGGAGGTGATCGCCGTC **GACGGCTATGTCGGCGCG
CCTGCCCAC**CGGATAGCCGACCAGTCGGTGGTGGTCACCATGACCGATGCTGAAGAGCTG
ACGGCGGTGATCCGGCGGCTGCAACCGGATTTCTTGGTGACGGTCACCGCCGCGGTGTCT
GTGGATGCTCTCGATGCCGTCGAGCAAGCCGACGGCGAGTGCACTGAGCTGGTGCCGAAC
GCCCGTGCCGTCCGGTGCACGGCCGACCGGGAGGGCCTGCGCCGGCTGGCCGCCGATCAG
CTCGGCCTGCCCACAGCCCCGTTCTGGTTCGTCGGATCCCTTGGCGAACTTCAAGCGGTG
GCCGTCCATGCTGGGTTTCCGTTGCTGGTGAGCCCGGTGGCAGGGGTGGCTGGCCAGGGT
AGCTCGGTGGTCGCCGGGCCCAACGAGGTCGAGCCCGCCTGGCAGCGCGCGGCAGGCCAT
CAAGTACAGCCGCAGACTGGGGGAGTGAGCCCTCGGGTGTGCGCCGAGTCGGTGGTCGAG
ATCGAGTTTTTGGTCACCATGATCGTTGTGTGCAGTCAGGGCCCGAACGGGCCGCTCATC
GAGTTCTGTGCACCTATCGGTCATCGCGACGCCGATGCCGGTGAGTTGGAATCCTGGCAA
CCGCAGAAGCTGAGCACGGCGGCGCTGGACGCGGCCAAGTCGATCGCCGCGCGCATCGTC
AAGGCGCTCGGGGGACGCGGGGTTTTCGGCGTCGAATTGATGATCAACGGCGATGAGGTG
TATTTCGCCGATGTCACCGTGTGTCCTGCCGGGAGTGCCTGGGTCACCGTGCGCAGCCAG
CGGCTTTCGGTGTTCGAACTGCAGGCCCGGGCGATCCTGGGTCTGGCGGTGGACACCCTG
ATGATCTCGCCGGGTGCCGCGCGGGTGATCAACCCGGACCACACGGCAGGCCGGGCAGCG
GTCGGCGCCGCACCACCTGCCGATGCGCTGACCGGTGCGCTCGGTGTGCCGGAAAGCGAC
GTCGTGATATTCGGCCGCGGGCTTGGGGTGGCGCTGGCCACCGCACCCGAGGTGGCAATC
GCCCGCGAACGCGCCCGCGAAGTTGCATCTCGGCTAAATGTGCCAGACTCACGCGAGTGA
(SEQ ID NO: 3)

Fig. 1A

Protein Sequence

SEQ ID NO: 6 - LAAVVGVVLAQVL

>Mb0073
MLFAALRDMQWRKRRLVITIISTGLIFGMTLVLTGLANGFRVEARHTVDSMGVDVFVVRS
GAAGPFLGSIPFPDVDLARVAAEPGVMAAAPLGSVGTIMKEGTSTRNVTVFGAPEHGPGM
PRVSEGRSPSKPDEVAASSTMGRHLGDTVEVGARRLRVVGIVPNSTALAKIPNVFLTTEG
LQKLAYNGQPNITSIGIIGMPRQLPEGYQTFDRVGAVNDLVRPLKVAVNSISIVAVLLWI
VAVLIVGSVVYLSALERLRDFAVFKAIGTPTRSIMAGLALQALVIAL<u>LAAVVGVVLAQVL</u>
APLFPMIVAVPVGAYLALPVAAIVIGLFASVAGLKRVVTVDPAQAFGGP (SEQ ID NO: 8)

DNA Sequence

SEQ ID NO: 5 - CTTGCGGCGGTGGTGGGCGTCGTCCTGGCGCAGGTGTTG

>Mb0073
ATGCTCTTCGCGGCCCTGCGTGACATGCAATGGAGAAAGCGCCGCCTGGTCATCACGATC
ATCAGCACCGGGCTGATCTTCGGGATGACGCTTGTTTTGACCGGACTCGCGAACGGCTTC
CGGGTGGAGGCCCGGCACACCGTCGATTCCATGGGTGTCGATGTATTCGTCGTCAGATCC
GGCGCTGCTGGACCTTTTCTGGGTTCAATACCGTTTCCCGATGTTGACCTGGCCCGAGTG
GCCGCTGAACCCGGTGTCATGGCCGCGGCCCCGTTGGGCAGCGTGGGGACGATCATGAAA
GAAGGCACGTCGACGCGAAACGTCACGGTCTTCGGCGCGCCCGAGCACGGACCTGGCATG
CCACGGGTCTCAGAGGGTCGGTCACCGTCGAAACCGGACGAAGTCGCGGCATCGAGCACG
ATGGGCCGACACCTCGGTGACACTGTCGAGGTCGGCGCGCGCAGATTGCGGGTCGTTGGC
ATTGTGCCGAATTCCACCGCGCTGGCCAAGATCCCCAATGTCTTCCTCACGACCGAGGGC
TTACAGAAATTGGCGTACAACGGGCAGCCGAATATCACGTCCATCGGGATCATAGGTATG
CCCCGACAGCTGCCGGAGGGTTACCAGACTTTCGATCGGGTGGGCGCTGTCAATGATTTG
GTGCGCCCATTGAAGGTCGCAGTGAATTCGATCTCGATCGTGGCTGTTTTGCTGTGGATT
GTGGCGGTGCTGATCGTCGGCTCGGTGGTGTACCTTTCGGCTCTTGAGCGGCTACGTGAC
TTCGCGGTGTTCAAGGCGATTGGCACGCCAACGCGCTCGATTATGGCCGGGCTCGCATTA
CAGGCGCTGGTCATTGCGTTG<u>CTTGCGGCGGTGGTGGGCGTCGTCCTGGCGCAGGTGTTG</u>
GCACCACTGTTTCCGATGATTGTCGCGGTACCCGTCGGTGCTTACCTGGCGCTACCGGTG
GCCGCGATCGTCATCGGTCTGTTCGCTAGTGTTGCCGGATTGAAGCGCGTGGTGACGGTC
GATCCCGCGCAGGCGTTCGGAGGTCCCTAG (SEQ ID NO: 7)

Fig. 1B

Protein Sequence

SEQ ID NO: 10 - RSGAATPVR

>MT2160.1
MPAAPSTREKDCMLVLHGFWSNSGGMRLWAEDSDLLVKSPSQALRSGAATPVRGAR (SEQ ID NO: 12)

DNA Sequence

SEQ ID NO: 9 - CGCTCCGGCGCGGCCACACCCGTTCGC

>MT2160.1
GTGCCGGCCGCTCCGTCGACAAGAGAGAAGGACTGCATGCTGGTTTTGCACGGCTTCTGG
TCCAACTCCGGCGGGATGCGGCTGTGGGCGGAGGACTCCGATCTGCTGGTGAAGAGCCCG
AGTCAGGCGCTGCGCTCCGGCGCGGCCACACCCGTTCGCGGCGCCCGCTGA (SEQ ID NO: 11)

Fig. 1C

Protein Sequence

SEQ ID NO: 14 - TCLPFAL

>MT0910.2
MSAPPAQAPVCGALAARPTAPGNASCTRPAKRDCRYGSRCE<u>TCLPFAL</u>AKDCRQASSRLQ
AATEPDETTTTSVISMRSPGSLQYQPAT (SEQ ID NO: 16)

DNA Sequence

SEQ ID NO: 13 - ACCTGCCTCCCATTCGCACTA

>MT0910.2
ATGTCCGCGCCACCCGCTCAAGCGCCGGTATGTGGCGCCTTGGCGGCTAGGCCAACCGCC
CCCGGCAACGCCAGCTGCACACGCCCAGCGAAGCGCGATTGTCGGTACGGGTCGCGCTGC
GAA<u>ACCTGCCTCCCATTCGCACTA</u>GCAAAAGACTGTCGACAAGCGAGCAGTCGACTTCAG
GCCGCGACCGAACCCGACGAGACGACAACAACATCTGTCATCTCAATGCGCTCACCAGGA
TCGCTACAATATCAGCCAGCTACATGA (SEQ ID NO: 15)

Fig. 1D

Protein Sequence

SEQ ID NO: 18 - TTMPLFAD

>Mb1654c
MPEVTREEPAIDGWFTTDKAGNPHLLGGKCPQCGTYVFPPRADNCPNPACGSDTLESVGL
STRGKLWSYTENRYAPPPPYPAPDPFEPFAVAAVELADEGLIVLGKVVDGTLAADLKVGM
EMEL<u>TTMPLFAD</u>DDGVQRIVYAWRIPSRAGDDAERSDAEERRR (SEQ ID NO: 20)

DNA Sequence

SEQ ID NO: 17 - ACGACCATGCCGCTGTTCGCCGAC

>Mb1654c
GTGCCAGAGGTCACCCGTGAAGAACCGGCAATCGATGGATGGTTCACCACCGATAAGGCC
GGCAACCCGCATCTGCTCGGCGGCAAGTGTCCCCAGTGCGGCACGTACGTCTTCCCACCC
CGGGCGGACAATTGTCCGAATCCGGCTTGCGGCAGCGACACACTAGAGTCGGTCGGACTG
TCGACCCGCGGAAAGCTTTGGAGCTACACCGAAAACCGGTACGCCCCGCCACCGCCGTAC
CCGGCACCCGACCCCTTTGAGCCGTTTGCCGTGGCCGCGGTGGAACTGGCCGACGAGGGA
CTGATCGTGCTGGGCAAAGTGGTCGATGGCACGCTGGCCGCCGATCTGAAGGTCGGCATG
GAGATGGAGCTG<u>ACGACCATGCCGCTGTTCGCCGAC</u>GACGACGGTGTGCAGCGCATCGTC
TACGCGTGGCGGATCCCATCGCGCGCCGGCGACGATGCAGAGCGCAGCGATGCTGAGGAG
CGGCGCCGATGA (SEQ ID NO: 19)

Fig. 1E

Protein Sequence

SEQ ID NO: 22 – VLVALAALGTQPWQDFAEQETAGLAIILDNVTHGEWASTILAAGAVV

>Mb2347c
MPTTSMSLRELMLRRRPVSGAPVASGASGNLKRSFGTFQLTMFGVGATIGTGIFFVLAQA
VPEAGPGVIVSFIIAGIAAGLAAICYAELASAVPISGSAYSYAYTTLGEAVAMVVAACLL
LEYGVATAAVAVGWSGYVNKLLSNLFGFQMPHVLSAAPWDTHPGWVNLPAVILIGLCALL
LIRGASESARVNAIMVLIKLGVLGMFMIIAFSAYSADHLKDFVPFGVAGIGSAAGTIFFS
YIGLDAVSTAGDEVKDPQKTMPRALIAALVVVTGVY**VLVALAALGTQPWQDFAEQETAGLAII
LDNVTHGEWASTILAAGAVV**SIFTVTLVTMYGQTRILFAMGRDGLLPARFAKVNPRTMTPVHNT
VIVAIFASTLAAFIPLDSLADMVSIGTLTAFSVVAVGVIVLRVREPDLPRGFK
VPGYPVTPVLSVLACGYILASLHWYTWLAFSGWVAVAVIFYLMWGRHHSALNEEVP (SEQ ID NO: 24)

DNA Sequence

SEQ ID NO: 21 -
GTGCTGGTCGCACTGGCCGCGCTGGGCACCCAACCGTGGCAGGACTTCGCAGAGCAGG
AAACCGCCGGGCTGGCCATCATCTTGGACAACGTCACGCATGGCGAATGGGCCAGCACG
ATTCTGGCCGCCGGTGCGGTGGTC

>Mb2347c
TTGCCGACAACGTCGATGAGCCTTCGAGAACTGATGCTGCGGCGCCGCCCGGTGAGCGGC
GCCCCGGTCGCATCCGGGGCATCGGGGAACCTCAAGCGGAGTTTCGGCACCTTCCAGCTG
ACCATGTTCGGGGTTGGCGCGACGATAGGTACCGGCATCTTTTTCGTGCTTGCCCAGGCA
GTTCCAGAGGCCGGCCCGGGCGTGATTGTTTCGTTCATCATCGCCGGCATCGCCGCTGGG
CTCGCGGCTATCTGCTACGCGGAACTGGCTTCCGCCGTGCCGATTTCCGGGTCGGCGTAC
TCCTACGCGTACACGACGCTGGGCGAGGCGGTCGCGATGGTGGTGGCGGCCTGCCTACTG
CTGGAATACGGGGTAGCCACCGCAGCGGTCGCGGTCGGCTGGAGTGGCTACGTGAACAAG
CTGCTGAGTAATCTGTTCGGATTTCAGATGCCGCACGTATTGTCGGCGGCGCCGTGGGAC
ACCCATCCCGGTTGGGTGAACCTGCCCGCCGTCATCCTGATCGGGCTATGCGCGCTGCTG
TTGATTCGAGGGGCCAGCGAGTCGGCGAGGGTCAACGCGATCATGGTGCTGATCAAGCTC
GGCGTGCTGGGCATGTTCATGATCATCGCGTTCAGCGCGTACAGCGCCGACCACCTCAAG
GATTTCGTCCCATTCGGCGTCGCCGGCATCGGCTCCGCGGCGGGCACGATCTTCTTCTCA
TACATCGGCCTTGACGCGGTGTCGACCGCCGGCGACGAGGTGAAGGACCCGCAGAAGACC
ATGCCGCGTGCGCTGATCGCAGCGCTGGTGGTCGTCACCGGTGTCTAC**GTGCTGGTCGCA
CTGGCCGCGCTGGGCACCCAACCGTGGCAGGACTTCGCAGAGCAGGAAACCGCCGGGC
TGGCCATCATCTTGGACAACGTCACGCATGGCGAATGGGCCAGCACGATTCTGGCCGCC
GGTGCGGTGGTC**TCGATTTTCACCGTCACGCTGGTCACCATGTACGGCCAGACCCGGATCCT
GTTCGCGATGGGGCGCGACGGGCTGCTGCCGGCGCGGTTCGCGAAGGTGAATCCGCGCACC
ATGACGCCGGTGCACAACACGGTGATCGTCGCGATCTTCGCATCGACGCTGGCCGCCTTC
ATACCGCTGGATAGCTTGGCGGACATGGTGTCCATCGGCACGCTCACCGCGTTCAGCGTG
GTGGCTGTGGGTGTGATCGTTCTACGGGTGCGCGAGCCCGACTTACCCCGAGGGTTCAAG
GTACCCGGTTACCCTGTGACGCCTGTTCTTTCGGTGCTGGCCTGCGGGTATATCCTGGCC
AGCTTGCACTGGTACACCTGGCTGGCGTTCAGCGGATGGGTGGCGGTGGCAGTGATCTTT
TACCTGATGTGGGGTCGGCACCACAGTGCGCTCAACGAGGAAGTGCCGTGA (SEQ ID NO: 23)

Fig. 1F

Protein Sequence

SEQ ID NO: 26 - CAVVLATMPPLLSAIANA
>MT1515
MTLTACEVTAAEAPFDRVSKTIPHPLSWGAALWSVVSVRWATVALLLFLAGLVAQLNGAP
EAMWWTLYLACYLAGGWGSAWAGAQALRNKALDVDLLMIAAAVGAVAIGQIFDGALLIVI
FATSGALDDIATRHTAESVKGLLDLAPDQAVVVQGDGSERVVAASELVVGDRVVVRPGDR
IPADGAVLSGASDVDQRSITGESMPVAKARGDEVFAGTVNGSGVLHLVVTRDPSQTVVAR
IVELVADASATKAKTQLFIEKIEQRYSLGMVAATLALIVIPLMFGADLRPVLLRAMTFMI
VASP<u>CAVVLATMPPLLSAIANA</u>GRHGVLVKSAVVVERLADTSIVALDKTGTLTRGIPRLA
SVAPLDPNVVDARRLLQLAAAAEQSSEHPLGRAIVAEARRRGIAIPPAKDFRAVPGCVH
ALVGNDFVEIASPQSYRGAPLAELAPLLSAGATAAIVLLDGVAIGVLGLTDQLRPDAVES
VAAMAALTAAPPVLLTGDNGRAAWRVARNAGITDVRAALLPEQKVEVVRNLQAGGHQVLL
VGDGVNDAPAMAAARAAVAMGAGADLTLQTADGVTIRDELHTIPTIIGLARQARRVVTVN
LAIAATFIAVLVLWDLFGQLPLPLGVVGHEGSTVLVALNGMRLLTNRSWRAAASAAR (SEQ ID
NO: 28)

DNA Sequence

SEQ ID NO: 25 - TGCGCGGTGGTGCTGGCCACCATGCCGCCGCTGCTTTCGGCGATCGCC
AACGCA
>MT1515
ATGACCTTGACCGCTTGTGAAGTAACTGCCGCGGAGGCTCCTTTCGACCGCGTTTCAAAG
ACCATTCCCCACCCATTGAGCTGGGGAGCCGCGCTGTGGTCGGTAGTCTCCGTGCGCTGG
GCCACCGTGGCGCTGCTGCTGTTTCTCGCCGGACTAGTGGCGCAACTGAACGGTGCTCCC
GAGGCCATGTGGTGGACGCTTTACCTGGCCTGTTATCTGGCCGGCGGCTGGGGCTCGGCA
TGGGCGGGCGCACAAGCGTTGCGGAACAAGGCACTTGATGTGGATCTGCTGATGATTGCC
GCGGCGGTCGGAGCGGTCGCGATTGGGCAGATCTTCGACGGCGCGCTGCTGATCGTGATC
TTCGCCACGTCCGGTGCGCTGGATGACATTGCCACCAGACACACCGCGGAATCGGTCAAA
GGCCTGCTGGACCTCGCGCCGGATCAGGCGGTGGTGGTCCAGGGCGACGGCAGCGAACGG
GTGGTGGCGGCCAGCGAGCTGGTGGTGGGGGACCGGGTGGTGGTGCGGCCGGGGGACCGG
ATACCCGCAGACGGTGCGGTGCTGTCGGGGGCTAGCGACGTCGACCAACGCTCGATCACC
GGTGAATCGATGCCGGTGGCCAAGGCCCGCGGTGACGAGGTGTTCGCCGGCACCGTGAAC
GGATCGGGTGTATTGCATCTGGTGGTCACCCGTGACCCGAGCCAGACCGTGGTAGCCCGC
ATCGTCGAACTGGTCGCCGACGCTTCGGCGACGAAGGCCAAAACCCAACTGTTCATTGAG
AAAATCGAGCAACGCTACTCCCTGGGCATGGTCGCGGCCACCCTTGCCCTCATCGTTATT
CCGCTGATGTTCGGCGCCGACCTGCGGCCGGTGCTGCTGCGCGCCATGACCTTCATGATC
GTGGCATCGCCA<u>TGCGCGGTGGTGCTGGCCACCATGCCGCCGCTGCTTTCGGCGATCGC
CAACGCA</u>GGCCGTCATGGGGTGCTGGTCAAATCCGCGGTGGTCGTCGAACGCCTGGCCGAT
ACCAGCATCGTCGCTTTGGACAAGACCGGTACGCTGACCCGTGGCATCCCGCGACTGGCT
TCCGTCGCACCGCTGGACCCCAACGTGGTCGATGCCCGGCGATTGTTGCAATTGGCAGCT
GCCGCAGAACAATCCAGCGAGCACCCGCTTGGCCGGGCGATCGTCGCGGAAGCTCGTCGG
CGTGGTATCGCCATACCGCCCGCCAAGGACTTCCGCGCGGTCCCGGGCTGCGGGGTCCAC
GCCCTGGTGGGCAACGATTTCGTCGAGATCGCCAGCCCGCAAAGCTACCGCGGTGCACCG
CTAGCAGAGCTGGCGCCGCTCCTTTCTGCCGGCGCCACTGCCGCCATCGTCTTGTTGGAT
GGAGTTGCCATCGGTGTGCTCGGGCTCACCGATCAGCTTCGTCCGGATGCCGTGGAGTCC
GTCGCGGCGATGGCTGCATTGACCGCCGCACCACCGGTGCTGCTCACGGGTGACAACGGG
CGAGCGGCTTGGCGGGTCGCTCGGAACGCCGGGATCACCGATGTGCGAGCCGCATTGCTG
CCCGAGCAGAAGGTTGAAGTCGTGCGCAACCTGCAGGCCGGTGGTCACCAGGTGCTGCTC
GTCGGCGACGGCGTCAACGACGCTCCCGCCATGGCCGCCGCCCGCGCCGCTGTCGCCATG
GGCGCCGGCGCCGATCTGACCCTACAGACCGCAGACGGGGTGACCATACGGGACGAACTG
CACACCATCCCGACGATCATCGGGTTGGCACGGCAGGCGCGCCGGGTGGTCACCGTCAAC
CTGGCCATCGCGGCCACCTTCATCGCCGTCCTGGTGCTGTGGGACCTTTTGGGCAGCTG
CCGCTGCCACTGGGTGTGGTGGGTCACGAAGGGTCCACTGTGCTGGTGGCCCTCAACGGC
ATGCGGCTATTGACCAACCGGTCGTGGCGGGCCGCGGCTTCGGCTGCGCGTTAG (SEQ ID NO:
27)

Fig. 1G

| SEQ ID NO: | Sequence | TIGR annotation | Swiss-Prot | Protein Name |
|---|---|---|---|---|
| 2 | DGYVGAPAH (9mer) | MT0401 | P95197 | 5'-PHOSPHORIBOSYLGLYCINAMIDE TRANSFORMYLASE 2 |
| 6 | LAAVVGVVLAQVL (13mer) | Mb0073 | Q7U2X3 | PROBABLE GLUTAMINE TRANSPORT TRANSMEMBRANE PROTEIN ABC TRANSPORTER |
| 10 | RSGAATPVR (9mer) | MT2160.1 | Q8VJQ5 | HYPOTHETICA PROTEIN |
| 14 | TCLPFAL (7mer) | MT0910.2 | Q8VKC1 | HYPOTHETICAL PROTEIN |
| 18 | TTMPLFAD (8mer) | Mb1654c | Q7TZV3 | HYPOTHETCAL PROTEIN |
| 22 | VLVALAALGTQPWQDFAEQETAGLAIILDNV THGEWASTILAAGAVV (47mer) | Mb2347c | Q7TYU0 | PROBABLE CATIONIC AMINO ACID TRANSPORT INTEGRAL MEMBRANE PROTEIN ROCE |
| 26 | CAVVLATMPPLLSAIANA (8mer) | Mb1504 | O53160 | PROBABLE CATION TRANSPORTING PTYPE ATPASE D |

Fig. 1H

Protein and DNA sequences of TB peptide found in urine of TB patient:

Protein Sequence

SEQ ID NO: 30 - MVIIELMRR

\>MT1721
MVIIELMRRVVGLAQGATAEVAVYGDRDRDLAERWCANTGNTLVRADVDQTGVGTLVVRR
GHPPDPASVLGPDRLPGVRLWLYTNFHCNLCCDYCCVSSSPSTPHRELGAERIGRIVGEA
ARWGVRELFLTGGEPFLLPDIDTIIATCVKQLPTTVLTNGMVFKGRGRRALESLPRGLAL
QISLDSATPELHDAHRGAGTWVKAVAGIRLALSLGFRVRVAATVASPAPGELTAFHDFLD
GLGIAPGDQLVRPIALEGAASQGVALTRESLVPEVTVTADGVYWHPVAATDERALVTRTV
EPLTPALDMVSRLFAEQWTRAAEEAALFPCA (SEQ ID NO: 32)

DNA Sequence

SEQ ID NO: 29 - ATGGTGATCATAGAGCTGATGCGCCGG

\>MT1721
ATGGTGATCATAGAGCTGATGCGCCGGGTGGTAGGTCTCGCACAGGGAGCTACCGCCGAG
GTCGCCGTCTATGGCGACCGAGATCGTGATCTCGCGGAGCGATGGTGCGCGAACACCGGA
AACACCCTGGTGCGCGCCGACGTGGACCAGACCGGCGTCGGCACCCTGGTGGTGCGCCGC
GGCCATCCGCCTGACCCGGCAAGCGTGTTGGGCCCCGACCGGCTACCCGGGGTCCGGTTG
TGGCTGTACACCAACTTCCACTGCAACCTGTGCTGCGACTACTGCTGCGTCTCGTCGTCA
CCAAGCACCCCGCATCGCGAACTGGGGCGGAGCGGATCGGCCGAATCGTCGGTGAAGCG
GCGCGCTGGGGAGTGCGCGAACTGTTCCTCACCGGCGGTGAGCCGTTCCTGCTGCCCGAC
ATCGACACGATCATCGCGACCTGTGTGAAGCAGTTGCCCACCACCGTCCTCACCAACGGC
ATGGTGTTCAAAGGGCGGGGTCGGCGCGCGCTGGAATCCCTACCTAGAGGGCTCGCCTTG
CAGATCAGCCTGGACTCGGCCACCCCGGAGCTGCACGATGCGCACCGCGGCGCGGGGACG
TGGGTCAAGGCAGTAGCTGGTATCCGGTTGGCGCTCTCACTTGGCTTCCGGGTGCGGGTG
GCCGCGACGGTTGCCAGCCCCGCACCTGGCGAGCTGACGGCGTTTCACGACTTCCTCGAC
GGGCTTGGCATCGCACCCGGGGATCAGCTGGTCCGGCCGATCGCGCTGGAGGGCGCCGCG
TCGCAAGGGGTGGCGCTCACCCGCGAATCGCTGGTTCCCGAGGTGACCGTCACCGCCGAC
GGCGTGTACTGGCACCCAGTGGCCGCCACCGACGAGCGCGCCCTGGTCACCCGTACCGTC
GAACCCTTGACCCCGGCGCTGGACATGGTAAGCCGGCTATTCGCCGAACAGTGGACACGA
GCCGCCGAAGAGGCCGCGTTGTTCCCGTGTGCGTAG (SEQ ID NO: 31)

Fig. 2

*Mycobacterium tuberculosis* peptides found in the urine of patients with pulmonary tuberculosis

| SEQ ID NO: | Peptide | *M. tuberculosis* donor protein |
| --- | --- | --- |
| 34 | RATADQIGTQTTQIAAIKA | Homoserine O-acetyltransferase |
| 38 | RTAEERANAVRGRADSLRR | Chromosome partition protein smc |
| 42 | RLHAQKALLVWLLERS | Ornithine carbamoyltransferase |
| 46 | RWTDETFGDIGGAGGGVSGHRG | Phosphoadenosine phosphosulfate reductase |

Fig. 5

Protein: Homoserine O-acetyltransferase

Peptide: RATADQIGTQTTQIAAIKA (SEQ ID NO: 34)

| TIGR Annotation for MT3444 ||
|---:|:---|
| TIGR Locus Name: | MT3444 |
| Primary Locus Name: | None |
| SWISS-PROT/TrEMBL AC: | O53391 |
| Putative identification: | homoserine O-acetyltransferase |
| Gene Symbol: | metA |
| TIGR Cellular role(s): | Amino acid biosynthesis: Aspartate family |
| Coordinates: | 3725096 to 3726235 |
| DNA Molecule Name: | chromosome Mycobacterium tuberculosis CDC1551 |
| Gene length: | 1140 |
| Protein length: | 379 |
| Molecular Weight: | 39798.68 |
| pI: | 5.3912 |
| Percent GC: | 69.31% |
| Enzyme Commission #: | 2.3.1.31 |
| Kingdom: | Bacteria |
| Family: | Actinobacteria |

Fig. 6A

Protein Sequence

SEQ ID NO: 34 - RATADQIGTQTTQIAAIKA

>MT3444
MTISDVPTQTLPAEGEIGLIDVGSLQLESGAVIDDVCIAVQRWGKLSPARDNVVVVLHAL
TGDSHITGPAGPGHPTPGWWDGVAGPSAPIDTTRWCAVATNVLGGCRGSTGPSSLARDGK
PWGSRFPLISIRDQVQADVAALAALGITEVAAVVGGSMGGARALEWVVGYPDRVRAGLLL
AVGARATADQIGTQTTQIAAIKADPDWQSGDYHETGRAPDAGLRLARRFAHLTYRGEIEL
DTRFANHNQGNEDPTAGGRYAVQSYLEHQGDKLLSRFDAGSYVILTEALNSHDVGRGRGG
VSAALRACPVPVVVGGITSDRLYPLRLQQELADLLPGCAGLRVVESVYGHDGFLVETEAV
GELIRQTLGLADREGACRR (SEQ ID NO: 36)

DNA Sequence

SEQ ID NO: 33 -
**CGTGCCACCGCAGACCAGATCGGCACGCAGACAACGCAAATCGCGGCC
ATCAAAGCC**

>MT3444
ATGACGATCTCCGATGTACCCACCCAGACGCTGCCCGCCGAAGGCGAAATCGGCCTGATA
GACGTCGGCTCGCTGCAACTGGAAAGCGGGGCGGTGATCGACGATGTCTGTATCGCCGTG
CAACGCTGGGGCAAATTGTCGCCCGCACGGGACAACGTGGTGGTGGTCTTGCACGCGCTC
ACCGGCGACTCGCACATCACTGGACCCGCCGGACCCGGCCACCCCACCCCCGGCTGGTGG
GACGGGGTGGCCGGGCCGAGTGCGCCGATTGACACCACCCGCTGGTGCGCGGTAGCTACC
AATGTGCTCGGCGGCTGCCGCGGCTCCACCGGGCCCAGCTCGCTTGCCCGCGACGGAAAG
CCTTGGGGCTCAAGATTTCCGCTGATCTCGATACGTGACCAGGTGCAGGCGGACGTCGCG
GCGCTGGCCGCGCTGGGCATCACCGAGGTCGCCGCCGTCGTCGGCGGCTCCATGGGCGGC
GCCCGGGCCCTGGAATGGGTGGTCGGCTACCCGGATCGGGTCCGAGCCGGATTGCTGCTG
GCGGTCGGTGCG**CGTGCCACCGCAGACCAGATCGGCACGCAGACAACGCAAATCGCGGCC
ATCAAAGCC**GACCCGGACTGGCAGAGCGGCGACTACCACGAGACGGGGAGGGCACCAGAC
GCCGGGCTGCGACTCGCCCGCCGCTTCGCGCACCTCACCTACCGCGGCGAGATCGAGCTC
GACACCCGGTTCGCCAACCACAACCAGGGCAACGAGGATCCGACGGCCGGCGGGCGCTAC
GCGGTGCAAAGTTATCTGGAACACCAAGGAGACAAACTGTTATCCCGGTTCGACGCCGGC
AGCTACGTGATTCTCACCGAGGCGCTCAACAGCCACGACGTCGGCCGCGGCCGCGGCGGG
GTCTCCGCGGCTCTGCGCGCCTGCCCGGTGCCGGTGGTGGTGGGCGGCATCACCTCCGAC
CGGCTCTACCCGCTGCGCCTGCAGCAGGAGCTGGCCGACCTGCTGCCGGGCTGCGCCGGG
CTGCGAGTCGTCGAGTCGGTCTACGGACACGACGGCTTCCTGGTGGAAACCGAGGCCGTG
GGCGAATTGATCCGCCAGACACTGGGATTGGCTGATCGTGAAGGCGCGTGTCGGCGGTGA
(SEQ ID NO: 35)

Fig. 6B

Protein: Chromosome partition protein smc

Peptide: RTAEERANAVRGRADSLRR (SEQ ID NO: 38)

| TIGR Annotation for MT2990 ||
|---:|:---|
| TIGR Locus Name: | MT2990 |
| Primary Locus Name: | None |
| SWISS-PROT/TrEMBL AC: | Q10970 |
| Putative identification: | chromosome segregation SMC protein, putative |
| TIGR Cellular role(s): | Cellular processes: Cell division |
| Coordinates: | 3232127 to 3228510 |
| DNA Molecule Name: | chromosome Mycobacterium tuberculosis CDC1551 |
| Gene length: | 3618 |
| Protein length: | 1205 |
| Molecular Weight: | 130637.03 |
| pI: | 4.9064 |
| Percent GC: | 67.28% |
| Kingdom: | Bacteria |
| Family: | Actinobacteria |

FIG. 7A

Protein Sequence

SEQ ID NO: 38 - RTAEERANAVRGRADSLRR

>MT2990
MYLKSLTLKGFKSFAAPTTLRFEPGITAVVGPNGSGKSNVVDALAWVMGEQGAKTLRGGK
MEDVIFAGTSSRAPLGRAEVTVSIDNSDNALPIEYTEVSITRRMFRDGASEYEINGSSCR
LMDVQELLSDSGIGREMHVIVGQGKLEEILQSRPEDRRAFIEEAAGVLKHRKRKEKALRK
LDTMAANLARLTDLTTELRRQLKPLGRQAEAAQRAAAIQADLRDARLRLAADDLVSRRAE
REAVFQAEAAMRREHDEAAARLAVASEELAAHESAVAELSTRAESIQHTWFGLSALAERV
DATVRIASERAHHLDIEPVAVSDTDPRKPEELEAEAQQVAVAEQQLLAELDAARARLDAA
RAELADRERRAAEADRAHLAAVREEADRREGLARLAGQVETMRARVESIDESVARLSERI
EDAAMRAQQTRAEFETVQGRIGELDQGEVGLDEHHERTVAALRLADERVAELQSAERAAE
RQVASLRARIDALAVGLQRKDGAAWLAHNRSGAGLFGSIAQLVKVRSGYEAALAAALGPA
ADALAVDGLTAAGSAVSALKQADGGRAVLVLSDWPAPQAPQSASGEMLPSGAQWALDLVE
SPPQLVGAMIAMLSGVAVVNDLTEAMGLVEIRPELRAVTVDGDLVGAGWVSGGSDRKLST
LEVTSEIDKARSELAAAEALAAQLNAALAGALTEQSARQDAAEQALAALNESDTAISAMY
EQLGRLGQEARAAEEEWNRLLQQRTEQEAVRTQTLDDVIQLETQLRKAQETQRVQVAQPI
DRQAISAAADRARGVEVEARLAVRTAEERANAVRGRADSLRRAAAAEREARVRAQQARAA
RLHAAAVAAAVADCGRLLAGRLHRAVDGASQLRDASAAQRQQRLAAMAAVRDEVNTLSAR
VGELTDSLHRDELANAQAALRIEQLEQMVLEQFGMAPADLITEYGPHVALPPTELEMAEF
EQARERGEQVIAPAPMPFDRVTQERRAKRAERALAELGRVNPLALEEFAALEERYNFLST
QLEDVKAARKDLLGVVADVDARILQVFNDAFVDVEREFRGVFTALFPGGEGRLRLTEPDD
MLTTGIEVEARPPGKKITRLSLLSGGEKALTAVAMLVAIFRARPSPFYIMDEVEAALDDV
NLRRLLSLFEQLREQSQIIIITHQKPTMEVADALYGVTMQNDGITAVISQRMRGQQVDQL
VTNSS (SEQ ID NO: 40)

DNA Sequence

SEQ ID NO: 37 -
**CGCACCGCCGAGGAACGCGCCAACGCGGTTCGCGGGCGGGCCGATTCGCTG
CGCCGT**
>MT2990
GTGTACCTCAAGAGTCTGACGTTGAAGGGCTTCAAGTCCTTCGCCGCGCCGACGACTTTA
CGCTTCGAGCCGGGCATTACGGCCGTCGTTGGGCCCAACGGCTCCGGCAAATCCAATGTG
GTCGATGCCCTGGCGTGGGTGATGGGGGAGCAGGGGGCAAAGACGCTGCGCGGCGGCAAG
ATGGAAGACGTCATCTTCGCCGGCACCTCGTCGCGTGCGCCGCTGGGCCGCGCCGAAGTC
ACCGTTAGCATCGACAACTCCGACAACGCACTGCCTATCGAATACACCGAGGTGTCGATC
ACCCGAAGAATGTTTCGCGACGGTGCCAGCGAATACGAAATCAACGGCAGCAGTTGCCGT
TTGATGGATGTGCAGGAGTTGCTGAGCGACTCCGGCATCGGCCGTGAGATGCATGTGATT
GTTGGGCAAGGGAAGCTCGAGGAGATCTTGCAGTCGCGGCCTGAGGATCGGCGGGCGTTC
ATCGAGGAAGCCGCCGGTGTGCTCAAGCATCGCAAGCGCAAGGAAAAAGCTCTGCGCAAA
CTCGACACGATGGCGGCGAACCTGGCCCGGCTCACCGATCTGACCACCGAGCTCCGGCGT
CAACTCAAACCGCTGGGCCGGCAGGCCGAGGCGGCCCAGCGTGCCGCGGCCATCCAAGCC
GATCTGCGCGACGCCCGGCTGCGCCTGGCGGCCGACGACTTGGTAAGCCGCAGAGCCGAA
CGGGAAGCGGTCTTTCAGGCCGAGGCTGCGATGCGCCGCGAGCATGACGAGGCCGCCGCC
CGGCTGGCGGTGGCATCCGAGGAGCTGGCCGCGCATGAGTCCGCGGTCGCCGAACTCTCG
ACGCGGGCCGAGTCGATCCAGCACACTTGGTTCGGGCTGTCTGCGCTGGCCGAACGGGTG
GACGCTACGGTGCGCATCGCCAGCGAACGCGCCCATCATCTCGATATCGAGCCGGTAGCG

FIG. 7B

```
GTCAGCGACACCGACCCCAGAAAGCCCGAGGAGCTAGAAGCCGAGGCCCAGCAGGTGGCC
GTCGCCGAGCAACAACTGTTAGCGGAGCTGGACGCGGCGCGTGCCCGACTCGATGCTGCC
CGTGCAGAGCTGGCCGACCGGGAGCGCCGCGCCGCCGAGGCCGACCGGGCACACCTGGCG
GCGGTCCGGGAGGAGGCGGACCGCCGTGAGGGACTGGCGCGGCTGGCTGGCCAGGTGGAG
ACCATGCGGGCGCGTGTCGAATCGATCGATGAGAGCGTGGCACGGTTGTCCGAGCGGATC
GAGGATGCCGCAATGCGCGCCCAGCAGACCCGAGCCGAGTTCGAAACCGTGCAGGGCCGC
ATCGGTGAACTGGATCAAGGCGAGGTCGGCCTGGATGAGCACCACGAGCGTACTGTGGCC
GCGTTGCGGTTGGCCGACGAACGCGTCGCCGAGCTGCAATCCGCCGAACGCGCCGCCGAA
CGCCAGGTGGCATCGCTACGGGCTCGCATCGATGCGCTCGCAGTGGGGCTACAGCGCAAG
GACGGCGCGGCGTGGCTGGCGCACAATCGCAGTGGCGCAGGGCTTTTCGGTTCGATCGCC
CAATTGGTGAAGGTACGTTCCGGCTATGAAGCGGCACTGGCCGCGGCGCTCGGGCCGGCG
GCCGACGCACTTGCGGTGGACGGCCTGACTGCCGCGGGTAGTGCCGTCAGCGCACTCAAA
CAAGCCGACGGCGGTCGCGCGGTCCTCGTGCTGAGTGACTGGCCGGCCCCGCAAGCCCCC
CAATCCGCCTCGGGGGAGATGCTGCCTAGCGGCGCCCAGTGGGCCCTAGACCTGGTCGAG
TCTCCACCGCAGTTGGTTGGCGCGATGATCGCCATGCTTTCGGGTGTCGCGGTGGTCAAC
GACCTGACTGAGGCAATGGGCCTGGTCGAGATTCGTCCGGAGCTACGCGCGGTCACCGTT
GACGGTGATCTGGTGGGCGCCGGCTGGGTCAGCGGCGGATCGGACCGCAAGCTGTCCACC
TTGGAGGTCACCTCCGAGATCGACAAGGCCAGGAGTGAGCTGGCCGCTGCCGAGGCGCTG
GCGGCGCAATTGAATGCGGCCCTGGCCGGTGCGCTGACCGAGCAGTCCGCCCGCCAGGAC
GCGGCCGAGCAAGCCTTGGCCGCGCTTAACGAATCCGACACGGCCATCTCGGCGATGTAC
GAGCAGCTGGGCCGCCTCGGGCAGGAGGCCCGCGCGGCGGAAGAAGAGTGGAACCGGTTG
CTGCAGCAGCGTACGGAACAGGAAGCCGTGCGCACACAGACTCTCGACGACGTCATACAA
CTTGAGACCCAGCTGCGTAAGGCCCAGGAGACCCAACGGGTGCAGGTGGCCCAACCGATC
GACCGCCAGGCGATCAGTGCCGCTGCCGATCGCGCCCGCGGTGTCGAAGTGGAAGCCCGG
CTGGCGGTG**CGCACCGCCGAGGAACGCGCCAACGCGGTTCGCGGGCGGGCCGATTCGCTG
CGCCGT**GCGGCAGCGGCGGAACGTGAGGCGCGGGTGCGGGCTCAGCAAGCACGCGCCGCA
AGACTGCATGCGGCCGCGGTGGCCGCAGCGGTCGCCGACTGCGGACGGCTGCTGGCCGGG
CGGTTGCACCGGGCGGTGGACGGGGCGTCGCAACTGCGCGACGCGTCGGCCGCGCAACGT
CAGCAGCGGTTAGCGGCGATGGCCGCGGTGCGCGACGAGGTGAACACGCTGAGCGCCCGA
GTGGGGGAACTCACCGATTCGCTGCACCGCGACGAGCTGGCTAACGCGCAGGCGGCGCTG
CGTATCGAGCAGCTTGAGCAGATGGTGCTAGAGCAGTTCGGAATGGCGCCGGCCGACTTG
ATCACCGAATACGGTCCACATGTGGCGCTACCACCGACCGAGCTCGAGATGGCTGAGTTC
GAGCAAGCCCGCGAACGCGGCGAGCAGGTGATTGCGCCCGCCCCATGCCGTTCGACCGG
GTTACCCAGGAGCGCCGGGCCAAACGCGCCGAGCGTGCGCTTGCCGAGTTGGGCAGGGTC
AACCCGCTGGCGCTCGAAGAGTTTGCTGCCTTGGAGGAGCGCTACAATTTCCTGTCCACC
CAACTCGAGGATGTCAAGGCTGCCCGCAAGGATCTGCTGGGCGTCGTCGCCGATGTTGAC
GCCCGCATCCTGCAGGTGTTCAATGACGCGTTCGTAGACGTGGAACGCGAATTTCGCGGC
GTGTTCACCGCATTGTTCCCCGGTGGTGAAGGACGGCTGCGGCTGACCGAGCCCGACGAC
ATGCTCACCACCGGCATCGAGGTCGAAGCCCGCCCGCCGGGCAAGAAGATTACCCGACTG
TCTTTGCTCTCCGGTGGCGAGAAGGCGCTGACCGCGGTGGCGATGCTGGTCGCGATCTTT
CGTGCCCGTCCATCGCCGTTCTACATCATGGACGAGGTGGAGGCCGCCCTCGACGACGTG
AACCTGCGCCGACTGCTCAGCCTGTTCGAACAGCTGCGAGAGCAGTCGCAGATCATCATC
ATCACCCACCAGAAGCCGACGATGGAGGTCGCGGACGCACTGTACGGCGTAACCATGCAG
AACGACGGCATCACCGCGGTCATCTCGCAGCGCATGCGCGGTCAGCAGGTGGATCAGCTG
GTTACCAATTCCTCGTAG (SEQ ID NO: 39)
```

FIG. 7C

Protein: Ornithine carbamoyltransferase

Peptide: RLHAQKALLVWLLERS (SEQ ID NO: 42)

| TIGR Annotation for MT1694 ||
|---:|:---|
| TIGR Locus Name: | MT1694 |
| Primary Locus Name: | None |
| SWISS-PROT/TrEMBL AC: | P94991 |
| Putative identification: | ornithine carbamoyltransferase |
| Gene Symbol: | argF |
| TIGR Cellular role(s): | Amino acid biosynthesis: Glutamate family |
| Coordinates: | 1860829 to 1861752 |
| DNA Molecule Name: | chromosome Mycobacterium tuberculosis CDC1551 |
| Gene length: | 924 |
| Protein length: | 307 |
| Molecular Weight: | 33057.22 |
| pI: | 5.0574 |
| Percent GC: | 68.95% |
| Enzyme Commission #: | 2.1.3.3 |
| Kingdom: | Bacteria |
| Family: | Actinobacteria |

FIG. 8A

Protein Sequence

SEQ ID NO: 42 - RLHAQKALLVWLLERS

>MT1694
MIRHFLRDDDLSPAEQAEVLELAAELKKDPVSRRPLQGPRGVAVIFDKNSTRTRFSFELG
IAQLGGHAVVVDSGSTQLGRDETLQDTAKVLSRYVDAIVWRTFGQERLDAMASVATVPVI
NALSDEFHPCQVLADLQTIAERKGALRGLRLSYFGDGANNMAHSLLLGGVTAGIHVTVAA
PEGFLPDPSVRAAAERRAQDTGASVTVTADAHAAAAGADVLVTDTWTSMGQENDGLDRVK
PFRPFQLNSRLLALADSDAIVLHCLPAHRGDEITDAVMDGPASAVWDEAEN**RLHAQKALL
VWLLERS** (SEQ ID NO: 44)

DNA Sequence

SEQ ID NO: 41 - CTGCACGCGCAGAAGGCGCTGCTGGTGTGGCTGCTGGAGCGCTCATGA

>MT1694
GTGATCAGGCATTTCCTGCGCGACGACGATCTGTCCCCGGCCGAACAGGCCGAGGTGCTC
GAGCTCGCGGCCGAGCTGAAGAAAGACCCGGTTAGCCGTCGTCCCCTGCAAGGGCCGCGC
GGGGTGGCGGTCATCTTCGACAAGAACTCCACCCGCACCCGGTTCTCCTTCGAGCTGGGC
ATCGCGCAGCTGGGCGGGCATGCCGTCGTCGTCGACAGCGGCAGCACCCAGCTGGGCCGC
GACGAAACCCTGCAGGACACCGCAAAGGTGTTGTCCCGCTACGTCGATGCCATCGTCTGG
CGAACCTTCGGCCAAGAGCGGCTGGACGCCATGGCGTCGGTCGCGACGGTGCCCGTGATC
AACGCGCTCTCCGATGAGTTCCATCCGTGTCAGGTGTTGGCCGACCTGCAGACCATCGCC
GAACGCAAGGGGGCGCTGCGCGGCCTGAGGTTGTCCTACTTCGGCGACGGCGCCAACAAC
ATGGCCCACTCGCTGCTGCTCGGCGGGGTCACCGCGGGTATCCACGTCACCGTCGCGGCT
CCCGAGGGCTTCCTGCCCGACCCGTCGGTGCGGGCCGCGGCCGAGCGCCGCGCCCAGGAT
ACCGGCGCCTCGGTGACTGTGACCGCCGACGCCCACGCGGCCGCCGCCGGCGCCGACGTT
CTGGTCACCGACACCTGGACGTCGATGGGCCAGGAAAACGACGGGTTGGACCGAGTGAAG
CCGTTTCGGCCGTTTCAGCTCAACTCGCGACTTCTGGCGCTGGCCGACTCGGATGCCATC
GTGTTGCATTGCCTGCCGGCCCATCGCGGCGACGAGATCACCGACGCGGTGATGGACGGG
CCGGCCAGCGCGGTGTGGACGAGGCCGAAAACCGG**CTGCACGCGCAGAAGGCGCTGCTG
GTGTGGCTGCTGGAGCGCTCATGA** (SEQ ID NO: 43)

FIG. 8B

Protein: Probable phosphoadenosine phosphosulfate reductase

Peptide: RWTDETFGDIGGAGGGVSGHRG (SEQ ID NO: 46)

| TIGR Annotation for MT2462 ||
|---:|:---|
| TIGR Locus Name: | MT2462 |
| Primary Locus Name: | None |
| SWISS-PROT/TrEMBL AC: | P71752 |
| Putative identification: | phosphoadenosine phosphosulfate reductase |
| Gene Symbol: | cysH |
| TIGR Cellular role(s): | Amino acid biosynthesis: Serine family<br>Central intermediary metabolism: Sulfur metabolism |
| Coordinates: | 2683698 to 2684462 |
| DNA Molecule Name: | chromosome Mycobacterium tuberculosis CDC1551 |
| Gene length: | 765 |
| Protein length: | 254 |
| Molecular Weight: | 27422.87 |
| pI: | 4.9994 |
| Percent GC: | 64.30% |
| Enzyme Commission #: | 1.8.99.4 |
| Kingdom: | Bacteria |
| Family: | Actinobacteria |

FIG. 9A

Protein Sequence

SEQ ID NO: 46 - RWTDETFGDIGGAGGGVSGHRG

>MT2462
MSGETTRLTEPQLRELAARGAAELDGATATDMLRWTDETFGDIGGAGGGVSGHRGWTTCN
YVVASNMADAVLVDLAAKVRPGVPVIFLDTGYHFVETIGTRDAIESVYDVRVLNVTPEHT
VAEQDELLGKDLFARNPHECCRLRKVVPLGKTLRGYSAWVTGLRRVDAPTRANAPLVSFD
ETFKLVKVNPLAAWTDQDVQEYIADNDVLVNPLVREGYPSIGCAPCTAKPAEGADPRSGR
WQGLAKTECGLHAS (SEQ ID NO: 48)

DNA Sequence

SEQ ID NO: 45 - **CGCTGGACCGACGAAACCTTCGGCGACATCGGCGGCGCC
GGCGGCGGCGTGAGCGGACATCGCGGG**

>MT2462
ATGAGCGGCGAGACAACCAGGCTGACCGAACCGCAACTACGTGAGCTGGCCGCGCGCGGA
GCTGCCGAACTCGACGGCGCCACCGCCACCGACATGTTG**CGCTGGACCGACGAAACCTTC
GGCGACATCGGCGGCGCCGGCGGCGGCGTGAGCGGACATCGCGGG**TGGACAACGTGCAAC
TACGTAGTTGCTTCCAACATGGCTGATGCGGTGCTGGTGGATCTGGCCGCCAAGGTGCGA
CCGGGCGTACCGGTCATCTTTCTTGATACCGGCTACCACTTCGTCGAAACAATCGGCACC
AGAGATGCGATCGAGTCCGTCTATGACGTCCGGGTGCTCAATGTCACTCCGGAGCACACA
GTGGCCGAGCAGGACGAACTGCTGGGCAAGGACTTGTTCGCCCGCAACCCCCATGAATGC
TGCCGGTTGCGCAAGGTCGTTCCCCTGGGCAAGACGCTGCGTGGCTACTCCGCGTGGGTG
ACCGGGCTACGGCGGGTCGATGCACCGACCCGGGCCAATGCCCCGCTGGTCAGCTTCGAT
GAGACGTTCAAACTAGTGAAGGTCAACCCGCTGGCGGCGTGGACCGACCAAGATGTGCAG
GAATACATTGCCGACAACGACGTGCTGGTTAATCCGCTTGTGCGGGAAGGCTATCCGTCG
ATCGGTTGCGCTCCGTGCACAGCCAAACCCGCCGAAGGCGCCGACCCGCGCAGCGGACGC
TGGCAGGGGCTGGCCAAGACCGAATGCGGGTTGCACGCCTCGTGA (SEQ ID NO:47)

FIG. 9B

SEQUENCE LISTING

```
<160> NUMBER OF SEQ ID NOS: 48

<210> SEQ ID NO 1
<211> LENGTH: 27
<212> TYPE: DNA
<213> ORGANISM: Mycobacterium tuberculosis

<400> SEQUENCE: 1
gacggctatg tcggcgcgcc tgcccac                                          27

<210> SEQ ID NO 2
<211> LENGTH: 9
<212> TYPE: PRT
<213> ORGANISM: Mycobacterium tuberculosis

<400> SEQUENCE: 2

Asp Gly Tyr Val Gly Ala Pro Ala His
1               5

<210> SEQ ID NO 3
<211> LENGTH: 1260
<212> TYPE: DNA
<213> ORGANISM: Mycobacterium tuberculosis

<400> SEQUENCE: 3
gtgatcgacg gctggacgga agaacagcac gaacccaccg ttaggcatga gcgcccagca      60
gctccccaag acgttcggcg ggtgatgttg ctgggttcgg ccgaacccag ccgggagctg     120
gcgatcgcgt tgcagggctt gggcgcggag gtgatcgccg tcgacggcta tgtcggcgcg     180
```

```
cctgcccacc ggatagccga ccagtcggtg gtggtcacca tgaccgatgc tgaagagctg    240
acggcggtga tccggcggct gcaaccggat tcttggtga cggtcaccgc cgcggtgtct    300
gtggatgctc tcgatgccgt cgagcaagcc gacggcgagt gcactgagct ggtgccgaac    360
gcccgtgccg tccggtgcac ggccgaccgg gagggcctgc gccggctggc cgccgatcag    420
ctcggcctgc ccacagcccc gttctggttc gtcggatccc ttggcgaact tcaagcggtg    480
gccgtccatg ctgggtttcc gttgctggtg agcccggtgg caggggtggc tggccagggt    540
agctcggtgg tcgccgggcc caacgaggtc gagcccgcct ggcagcgcgc ggcaggccat    600
caagtacagc cgcagactgg gggagtgagc cctcgggtgt gcgccgagtc ggtggtcgag    660
atcgagtttt tggtcaccat gatcgttgtg tgcagtcagg gcccgaacgg gccgctcatc    720
gagttctgtg cacctatcgg tcatcgcgac gccgatgccg gtgagttgga atcctggcaa    780
ccgcagaagc tgagcacggc ggcgctggac gcggccaagt cgatcgccgc gcgcatcgtc    840
aaggcgctcg ggggacgcgg ggttttcggc gtcgaattga tgatcaacgg cgatgaggtg    900
tatttcgccg atgtcaccgt gtgtcctgcc gggagtgcct gggtcaccgt gcgcagccag    960
cggctttcgg tgttcgaact gcaggcccgg gcgatcctgg gtctggcggt ggacaccctg   1020
atgatctcgc cgggtgccgc gcgggtgatc aacccggacc acacggcagg ccgggcagcg   1080
gtcggcgccg caccacctgc cgatgcgctg accggtgcgc tcggtgtgcc ggaaagcgac   1140
gtcgtgatat tcggccgcgg gcttggggtg gcgctggcca ccgcacccga ggtggcaatc   1200
gcccgcgaac gcgcccgcga agttgcatct cggctaaatg tgccagactc acgcgagtga   1260
```

<210> SEQ ID NO 4
<211> LENGTH: 419
<212> TYPE: PRT
<213> ORGANISM: Mycobacterium tuberculosis

<400> SEQUENCE: 4

```
Met Ile Asp Gly Trp Thr Glu Glu Gln His Glu Pro Thr Val Arg His
1               5                   10                  15

Glu Arg Pro Ala Ala Pro Gln Asp Val Arg Arg Val Met Leu Leu Gly
            20                  25                  30

Ser Ala Glu Pro Ser Arg Glu Leu Ala Ile Ala Leu Gln Gly Leu Gly
        35                  40                  45

Ala Glu Val Ile Ala Val Asp Gly Tyr Val Gly Ala Pro Ala His Arg
    50                  55                  60

Ile Ala Asp Gln Ser Val Val Thr Met Thr Asp Ala Glu Glu Leu
65                  70                  75                  80

Thr Ala Val Ile Arg Arg Leu Gln Pro Asp Phe Leu Val Thr Val Thr
                85                  90                  95

Ala Ala Val Ser Val Asp Ala Leu Asp Ala Val Glu Gln Ala Asp Gly
            100                 105                 110

Glu Cys Thr Glu Leu Val Pro Asn Ala Arg Ala Val Arg Cys Thr Ala
        115                 120                 125

Asp Arg Glu Gly Leu Arg Arg Leu Ala Ala Asp Gln Leu Gly Leu Pro
    130                 135                 140

Thr Ala Pro Phe Trp Phe Val Gly Ser Leu Gly Glu Leu Gln Ala Val
145                 150                 155                 160

Ala Val His Ala Gly Phe Pro Leu Leu Val Ser Pro Val Ala Gly Val
                165                 170                 175

Ala Gly Gln Gly Ser Ser Val Val Ala Gly Pro Asn Glu Val Glu Pro
            180                 185                 190
```

```
Ala Trp Gln Arg Ala Ala Gly His Gln Val Gln Pro Gln Thr Gly Gly
        195                 200                 205

Val Ser Pro Arg Val Cys Ala Glu Ser Val Val Glu Ile Glu Phe Leu
    210                 215                 220

Val Thr Met Ile Val Val Cys Ser Gln Gly Pro Asn Gly Pro Leu Ile
225                 230                 235                 240

Glu Phe Cys Ala Pro Ile Gly His Arg Asp Ala Asp Ala Gly Glu Leu
                245                 250                 255

Glu Ser Trp Gln Pro Gln Lys Leu Ser Thr Ala Ala Leu Asp Ala Ala
            260                 265                 270

Lys Ser Ile Ala Ala Arg Ile Val Lys Ala Leu Gly Gly Arg Gly Val
        275                 280                 285

Phe Gly Val Glu Leu Met Ile Asn Gly Asp Glu Val Tyr Phe Ala Asp
    290                 295                 300

Val Thr Val Cys Pro Ala Gly Ser Ala Trp Val Thr Val Arg Ser Gln
305                 310                 315                 320

Arg Leu Ser Val Phe Glu Leu Gln Ala Arg Ala Ile Leu Gly Leu Ala
                325                 330                 335

Val Asp Thr Leu Met Ile Ser Pro Gly Ala Ala Arg Val Ile Asn Pro
            340                 345                 350

Asp His Thr Ala Gly Arg Ala Ala Val Gly Ala Ala Pro Pro Ala Asp
        355                 360                 365

Ala Leu Thr Gly Ala Leu Gly Val Pro Glu Ser Asp Val Val Ile Phe
    370                 375                 380

Gly Arg Gly Leu Gly Val Ala Leu Ala Thr Ala Pro Glu Val Ala Ile
385                 390                 395                 400

Ala Arg Glu Arg Ala Arg Glu Val Ala Ser Arg Leu Asn Val Pro Asp
                405                 410                 415

Ser Arg Glu

<210> SEQ ID NO 5
<211> LENGTH: 39
<212> TYPE: DNA
<213> ORGANISM: Mycobacterium tuberculosis

<400> SEQUENCE: 5
cttgcggcgg tggtgggcgt cgtcctggcg caggtgttg                          39

<210> SEQ ID NO 6
<211> LENGTH: 13
<212> TYPE: PRT
<213> ORGANISM: Mycobacterium tuberculosis

<400> SEQUENCE: 6

Leu Ala Ala Val Val Gly Val Val Leu Ala Gln Val Leu
1               5                   10

<210> SEQ ID NO 7
<211> LENGTH: 1050
<212> TYPE: DNA
<213> ORGANISM: Mycobacterium tuberculosis

<400> SEQUENCE: 7
atgctcttcg cggccctgcg tgacatgcaa tggagaaagc gccgcctggt catcacgatc     60
atcagcaccg ggctgatctt cgggatgacg cttgttttga ccggactcgc gaacggcttc    120
cgggtggagg cccggcacac cgtcgattcc atgggtgtcg atgtattcgt cgtcagatcc    180
```

```
ggcgctgctg gacctttttct gggttcaata ccgtttcccg atgttgacct ggcccgagtg    240
gccgctgaac cggtgtcat ggccgcggcc ccgttgggca gcgtggggac gatcatgaaa     300
gaaggcacgt cgacgcgaaa cgtcacggtc ttcggcgcgc ccgagcacgg acctggcatg    360
ccacgggtct cagagggtcg gtcaccgtcg aaaccggacg aagtcgcggc atcgagcacg    420
atgggccgac acctcggtga cactgtcgag gtcggcgcgc gcagattgcg ggtcgttggc    480
attgtgccga attccaccgc gctggccaag atccccaatg tcttcctcac gaccgagggc    540
ttacagaaat ggcgtacaa cgggcagccg aatatcacgt ccatcgggat cataggtatg    600
ccccgacagc tgccggaggg ttaccagact ttcgatcggg tgggcgctgt caatgatttg    660
gtgcgcccat tgaaggtcgc agtgaattcg atctcgatcg tggctgttt gctgtggatt    720 gtggcggtgc tgatcgtcgg ctcggtggtg taccttcgg ctcttgagcg gctacgtgac    780
ttcgcggtgt tcaaggcgat tggcacgcca acgcgctcga ttatggccgg gctcgcatta    840
caggcgctgg tcattgcgtt gcttgcggcg gtggtgggcg tcgtcctggc gcaggtgttg    900
gcaccactgt ttccgatgat tgtcgcggta cccgtcggtg cttacctggc gctaccggtg    960
gccgcgatcg tcatcggtct gttcgctagt gttgccggat tgaagcgcgt ggtgacggtc   1020
gatcccgcgc aggcgttcgg aggtccctag                                    1050
```

<210> SEQ ID NO 8
<211> LENGTH: 349
<212> TYPE: PRT
<213> ORGANISM: Mycobacterium tuberculosis

<400> SEQUENCE: 8

```
Met Leu Phe Ala Ala Leu Arg Asp Met Gln Trp Arg Lys Arg Arg Leu
1               5                   10                  15

Val Ile Thr Ile Ile Ser Thr Gly Leu Ile Phe Gly Met Thr Leu Val
            20                  25                  30

Leu Thr Gly Leu Ala Asn Gly Phe Arg Val Glu Ala Arg His Thr Val
        35                  40                  45

Asp Ser Met Gly Val Asp Val Phe Val Val Arg Ser Gly Ala Ala Gly
    50                  55                  60

Pro Phe Leu Gly Ser Ile Pro Phe Pro Asp Val Asp Leu Ala Arg Val
65                  70                  75                  80

Ala Ala Glu Pro Gly Val Met Ala Ala Pro Leu Gly Ser Val Gly
            85                  90                  95

Thr Ile Met Lys Glu Gly Thr Ser Thr Arg Asn Val Thr Val Phe Gly
        100                 105                 110

Ala Pro Glu His Gly Pro Gly Met Pro Arg Val Ser Glu Gly Arg Ser
    115                 120                 125

Pro Ser Lys Pro Asp Glu Val Ala Ala Ser Ser Thr Met Gly Arg His
130                 135                 140

Leu Gly Asp Thr Val Glu Val Gly Ala Arg Arg Leu Arg Val Val Gly
145                 150                 155                 160

Ile Val Pro Asn Ser Thr Ala Leu Ala Lys Ile Pro Asn Val Phe Leu
            165                 170                 175

Thr Thr Glu Gly Leu Gln Lys Leu Ala Tyr Asn Gly Gln Pro Asn Ile
        180                 185                 190

Thr Ser Ile Gly Ile Ile Gly Met Pro Arg Gln Leu Pro Glu Gly Tyr
    195                 200                 205

Gln Thr Phe Asp Arg Val Gly Ala Val Asn Asp Leu Val Arg Pro Leu
    210                 215                 220
```

Lys Val Ala Val Asn Ser Ile Ser Ile Val Ala Val Leu Leu Trp Ile
225                 230                 235                 240

Val Ala Val Leu Ile Val Gly Ser Val Val Tyr Leu Ser Ala Leu Glu
            245                 250                 255

Arg Leu Arg Asp Phe Ala Val Phe Lys Ala Ile Gly Thr Pro Thr Arg
        260                 265                 270

Ser Ile Met Ala Gly Leu Ala Leu Gln Ala Leu Val Ile Ala Leu Leu
    275                 280                 285

Ala Ala Val Gly Val Val Leu Ala Gln Val Leu Ala Pro Leu Phe
290                 295                 300

Pro Met Ile Val Ala Val Pro Val Gly Ala Tyr Leu Ala Leu Pro Val
305                 310                 315                 320

Ala Ala Ile Val Ile Gly Leu Phe Ala Ser Val Ala Gly Leu Lys Arg
                325                 330                 335

Val Val Thr Val Asp Pro Ala Gln Ala Phe Gly Gly Pro
            340                 345

<210> SEQ ID NO 9
<211> LENGTH: 27
<212> TYPE: DNA
<213> ORGANISM: Mycobacterium tuberculosis

<400> SEQUENCE: 9
cgctccggcg cggccacacc cgttcgc                                           27

<210> SEQ ID NO 10
<211> LENGTH: 9
<212> TYPE: PRT
<213> ORGANISM: Mycobacterium tuberculosis

<400> SEQUENCE: 10

Arg Ser Gly Ala Ala Thr Pro Val Arg
1               5

<210> SEQ ID NO 11
<211> LENGTH: 171
<212> TYPE: DNA
<213> ORGANISM: Mycobacterium tuberculosis

<400> SEQUENCE: 11
gtgccggccg ctccgtcgac aagagagaag gactgcatgc tggttttgca cggcttctgg      60
tccaactccg gcgggatgcg gctgtgggcg gaggactccg atctgctggt gaagagcccg     120
agtcaggcgc tgcgctccgg cgcggccaca cccgttcgcg gcgcccgctg a              171

<210> SEQ ID NO 12
<211> LENGTH: 56
<212> TYPE: PRT
<213> ORGANISM: Mycobacterium tuberculosis

<400> SEQUENCE: 12

Met Pro Ala Ala Pro Ser Thr Arg Glu Lys Asp Cys Met Leu Val Leu
1               5                   10                  15

His Gly Phe Trp Ser Asn Ser Gly Gly Met Arg Leu Trp Ala Glu Asp
            20                  25                  30

Ser Asp Leu Leu Val Lys Ser Pro Ser Gln Ala Leu Arg Ser Gly Ala
        35                  40                  45

Ala Thr Pro Val Arg Gly Ala Arg
    50                  55

```
<210> SEQ ID NO 13
<211> LENGTH: 21
<212> TYPE: DNA
<213> ORGANISM: Mycobacterium tuberculosis

<400> SEQUENCE: 13
acctgcctcc cattcgcact a                                             21

<210> SEQ ID NO 14
<211> LENGTH: 7
<212> TYPE: PRT
<213> ORGANISM: Mycobacterium tuberculosis

<400> SEQUENCE: 14

Thr Cys Leu Pro Phe Ala Leu
1               5

<210> SEQ ID NO 15
<211> LENGTH: 267
<212> TYPE: DNA
<213> ORGANISM: Mycobacterium tuberculosis

<400> SEQUENCE: 15
atgtccgcgc acccgctca agcgccggta tgtggcgcct tggcggctag gccaaccgcc      60
cccggcaacg ccagctgcac acgcccagcg aagcgcgatt gtcggtacgg gtcgcgctgc     120
gaaacctgcc tcccattcgc actagcaaaa gactgtcgac aagcgagcag tcgacttcag     180
gccgcgaccg aacccgacga acgacaacaa acatctgtca tctcaatgcg ctcaccagga     240
tcgctacaat atcagccagc tacatga                                       267

<210> SEQ ID NO 16
<211> LENGTH: 88
<212> TYPE: PRT
<213> ORGANISM: Mycobacterium tuberculosis

<400> SEQUENCE: 16

Met Ser Ala Pro Pro Ala Gln Ala Pro Val Cys Gly Ala Leu Ala Ala
1               5                   10                  15

Arg Pro Thr Ala Pro Gly Asn Ala Ser Cys Thr Arg Pro Ala Lys Arg
            20                  25                  30

Asp Cys Arg Tyr Gly Ser Arg Cys Glu Thr Cys Leu Pro Phe Ala Leu
        35                  40                  45

Ala Lys Asp Cys Arg Gln Ala Ser Ser Arg Leu Gln Ala Ala Thr Glu
    50                  55                  60

Pro Asp Glu Thr Thr Thr Thr Ser Val Ile Ser Met Arg Ser Pro Gly
65                  70                  75                  80

Ser Leu Gln Tyr Gln Pro Ala Thr
                85

<210> SEQ ID NO 17
<211> LENGTH: 24
<212> TYPE: DNA
<213> ORGANISM: Mycobacterium tuberculosis

<400> SEQUENCE: 17
acgaccatgc cgctgttcgc cgac                                          24

<210> SEQ ID NO 18
<211> LENGTH: 8
<212> TYPE: PRT
<213> ORGANISM: Mycobacterium tuberculosis
```

-continued

<400> SEQUENCE: 18

Thr Thr Met Pro Leu Phe Ala Asp
1               5

<210> SEQ ID NO 19
<211> LENGTH: 492
<212> TYPE: DNA
<213> ORGANISM: Mycobacterium tuberculosis

<400> SEQUENCE: 19

```
gtgccagagg tcacccgtga agaaccggca atcgatggat ggttcaccac cgataaggcc    60
ggcaacccgc atctgctcgg cggcaagtgt ccccagtgcg gcacgtacgt cttcccaccc   120
cgggcggaca attgtccgaa tccggcttgc ggcagcgaca cactagagtc ggtcggactg   180
tcgacccgcg gaaagctttg gagctacacc gaaaaccggt acgccccgcc accgccgtac   240
ccggcacccg accccttga gccgtttgcc gtggccgcgg tggaactggc cgacgaggga   300
ctgatcgtgc tgggcaaagt ggtcgatggc acgctggccg ccgatctgaa ggtcggcatg   360
gagatggagc tgacgaccat gccgctgttc gccgacgacg acggtgtgca gcgcatcgtc   420
tacgcgtggc ggatcccatc gcgcgccggc gacgatgcag agcgcagcga tgctgaggag   480
cggcgccgat ga                                                       492
```

<210> SEQ ID NO 20
<211> LENGTH: 163
<212> TYPE: PRT
<213> ORGANISM: Mycobacterium tuberculosis

<400> SEQUENCE: 20

Met Pro Glu Val Thr Arg Glu Glu Pro Ala Ile Asp Gly Trp Phe Thr
1               5                   10                  15

Thr Asp Lys Ala Gly Asn Pro His Leu Leu Gly Gly Lys Cys Pro Gln
            20                  25                  30

Cys Gly Thr Tyr Val Phe Pro Pro Arg Ala Asp Asn Cys Pro Asn Pro
        35                  40                  45

Ala Cys Gly Ser Asp Thr Leu Glu Ser Val Gly Leu Ser Thr Arg Gly
    50                  55                  60

Lys Leu Trp Ser Tyr Thr Glu Asn Arg Tyr Ala Pro Pro Pro Tyr
65                  70                  75                  80

Pro Ala Pro Asp Pro Phe Glu Pro Phe Ala Val Ala Ala Val Glu Leu
                85                  90                  95

Ala Asp Glu Gly Leu Ile Val Leu Gly Lys Val Val Asp Gly Thr Leu
            100                 105                 110

Ala Ala Asp Leu Lys Val Gly Met Glu Met Glu Leu Thr Thr Met Pro
        115                 120                 125

Leu Phe Ala Asp Asp Asp Gly Val Gln Arg Ile Val Tyr Ala Trp Arg
    130                 135                 140

Ile Pro Ser Arg Ala Gly Asp Asp Ala Glu Arg Ser Asp Ala Glu Glu
145                 150                 155                 160

Arg Arg Arg

<210> SEQ ID NO 21
<211> LENGTH: 140
<212> TYPE: DNA
<213> ORGANISM: Mycobacterium tuberculosis

<400> SEQUENCE: 21

```
gtgctggtcg cactggccgc gctgggcacc caaccgtggc aggacttcgc agagcaggaa    60
```

```
accgccgggc tggccatcat cttggacaac gtcacgcatg gcgaatgggc cagcacgatt    120
ctggccgcgg tgcggtggtc                                                140

<210> SEQ ID NO 22
<211> LENGTH: 47
<212> TYPE: PRT
<213> ORGANISM: Mycobacterium tuberculosis

<400> SEQUENCE: 22

Val Leu Val Ala Leu Ala Ala Leu Gly Thr Gln Pro Trp Gln Asp Phe
1               5                   10                  15

Ala Glu Gln Glu Thr Ala Gly Leu Ala Ile Ile Leu Asp Asn Val Thr
            20                  25                  30

His Gly Glu Trp Ala Ser Thr Ile Leu Ala Ala Gly Ala Val Val
        35                  40                  45

<210> SEQ ID NO 23
<211> LENGTH: 1430
<212> TYPE: DNA
<213> ORGANISM: Mycobacterium tuberculosis

<400> SEQUENCE: 23
ttgccgacaa cgtcgatgag ccttcgagaa ctgatgctgc ggcgccgccc ggtgagcggc     60
gccccggtcg catccggggc atcggggaac ctcaagcgga gtttcggcac cttccagctg    120
accatgttcg gggttggcgc gacgataggt accggcatct ttttcgtgct tgcccaggca    180
gttccagagg ccggcccggg cgtgattgtt tcgttcatca tcgccggcat cgccgctggg    240
ctcgcggcta tctgctacgc ggaactggct tccgccgtgc cgatttccgg gtcggcgtac    300
tcctacgcgt acacgacgct gggcgaggcg gtcgcgatgg tggtggcggc ctgcctactg    360
ctggaatacg gggtagccac cgcagcggtc gcggtcggct ggagtggcta cgtgaacaag    420
ctgctgagta atctgttcgg atttcagatg ccgcacgtat tgtcggcggc gccgtgggac    480
acccatcccg gttgggtgaa cctgcccgcc gtcatcctga tcgggctatg cgcgctgctg    540
ttgattcgag gggccagcga gtcggcgagg gtcaacgcga tcatggtgct gatcaagctc    600
ggcgtgctgg gcatgttcat gatcatcgcg ttcagcgcgt acagcgccga ccacctcaag    660
gatttcgtcc cattcggcgt cgccggcatc ggctccgcgg cgggcacgat cttcttctca    720
tacatcggcc ttgacgcggt gtcgaccgcc ggcgacgagg tgaaggaccc gcagaagacc    780
atgccgcgtg cgctgatcgc agcgctggtg gtcgtcaccg tgtctacgt gctggtcgca    840 ctggccgcgc tgggcaccca accgtggcag gacttcgcag agcaggaaac cgccgggctg    900
gccatcatct tggacaacgt cacgcatggc gaatgggcca gcacgattct ggccgccggt    960
gcggtggctc gattttcacc gtcacgctgg tcaccatgta cggccagacc cggatcctgt   1020
tcgcgatggg gcgcgacggg ctgctgccgg cgcggttcgc gaaggtgaat ccgcgcacca   1080
tgacgccggt gcacaacacg gtgatcgtcg cgatcttcgc atcgacgctg ccgccttca    1140 taccgctgga tagcttggcg gacatggtgt ccatcggcac gctcaccgcg ttcagcgtgg   1200
tggctgtggg tgtgatcgtt ctacgggtgc gcgagcccga cttaccccga gggttcaagg   1260
tacccggtta ccctgtgacg cctgttcttt cggtgctggc ctgcgggtat atccggcca    1320 gcttgcactg gtacacctgg ctggcgttca gcggatgggt ggcggtggca gtgatctttt   1380
acctgatgtg gggtcggcac cacagtgcgc tcaacgagga agtgccgtga             1430

<210> SEQ ID NO 24
```

<211> LENGTH: 475
<212> TYPE: PRT
<213> ORGANISM: Mycobacterium tuberculosis

<400> SEQUENCE: 24

```
Met Pro Thr Thr Ser Met Ser Leu Arg Glu Leu Met Leu Arg Arg
1               5                   10                  15

Pro Val Ser Gly Ala Pro Val Ala Ser Gly Ala Ser Gly Asn Leu Lys
            20                  25                  30

Arg Ser Phe Gly Thr Phe Gln Leu Thr Met Phe Gly Val Gly Ala Thr
                35                  40                  45

Ile Gly Thr Gly Ile Phe Val Leu Ala Gln Ala Val Pro Glu Ala
    50                  55                  60

Gly Pro Gly Val Ile Val Ser Phe Ile Ile Ala Gly Ile Ala Ala Gly
65                  70                  75                  80

Leu Ala Ala Ile Cys Tyr Ala Glu Leu Ala Ser Ala Val Pro Ile Ser
                85                  90                  95

Gly Ser Ala Tyr Ser Tyr Ala Tyr Thr Leu Gly Glu Ala Val Ala
                100                 105                 110

Met Val Ala Ala Cys Leu Leu Glu Tyr Gly Val Ala Thr Ala
            115                 120                 125

Ala Val Ala Val Gly Trp Ser Gly Tyr Val Asn Lys Leu Leu Ser Asn
    130                 135                 140

Leu Phe Gly Phe Gln Met Pro His Val Leu Ser Ala Ala Pro Trp Asp
145                 150                 155                 160

Thr His Pro Gly Trp Val Asn Leu Pro Ala Val Ile Leu Ile Gly Leu
                165                 170                 175

Cys Ala Leu Leu Leu Ile Arg Gly Ala Ser Glu Ser Ala Arg Val Asn
            180                 185                 190

Ala Ile Met Val Leu Ile Lys Leu Gly Val Leu Gly Met Phe Met Ile
        195                 200                 205

Ile Ala Phe Ser Ala Tyr Ser Ala Asp His Leu Lys Asp Phe Val Pro
    210                 215                 220

Phe Gly Val Ala Gly Ile Gly Ser Ala Ala Gly Thr Ile Phe Phe Ser
225                 230                 235                 240

Tyr Ile Gly Leu Asp Ala Val Ser Thr Ala Gly Asp Glu Val Lys Asp
                245                 250                 255

Pro Gln Lys Thr Met Pro Arg Ala Leu Ile Ala Ala Leu Val Val Val
            260                 265                 270

Thr Gly Val Tyr Val Leu Val Ala Leu Ala Ala Leu Gly Thr Gln Pro
        275                 280                 285

Trp Gln Asp Phe Ala Glu Gln Glu Thr Ala Gly Leu Ala Ile Ile Leu
    290                 295                 300

Asp Asn Val Thr His Gly Glu Trp Ala Ser Thr Ile Leu Ala Ala Gly
305                 310                 315                 320

Ala Val Val Ser Ile Phe Thr Val Thr Leu Val Thr Met Tyr Gly Gln
                325                 330                 335

Thr Arg Ile Leu Phe Ala Met Gly Arg Asp Gly Leu Leu Pro Ala Arg
            340                 345                 350

Phe Ala Lys Val Asn Pro Arg Thr Met Thr Pro Val His Asn Thr Ile
        355                 360                 365

Val Ala Ile Phe Ala Ser Thr Leu Ala Ala Phe Ile Pro Leu Asp Ser
    370                 375                 380

Leu Ala Asp Met Val Ser Ile Gly Thr Leu Thr Ala Phe Ser Val Val
385                 390                 395                 400
```

```
Ala Val Gly Val Ile Val Leu Arg Val Arg Glu Pro Asp Leu Pro Arg
            405                 410                 415

Gly Phe Lys Val Pro Gly Tyr Pro Val Thr Pro Val Leu Ser Val Leu
            420                 425                 430

Ala Cys Gly Tyr Ile Leu Ala Ser Leu His Trp Tyr Thr Trp Leu Ala
            435                 440                 445

Phe Ser Gly Trp Val Ala Val Ala Val Ile Phe Tyr Leu Met Trp Gly
        450                 455                 460

Arg His His Ser Ala Leu Asn Glu Glu Val Pro
465                 470                 475

<210> SEQ ID NO 25
<211> LENGTH: 54
<212> TYPE: DNA
<213> ORGANISM: Mycobacterium tuberculosis

<400> SEQUENCE: 25
tgcgcggtgg tgctggccac catgccgccg ctgctttcgg cgatcgccaa cgca      54

<210> SEQ ID NO 26
<211> LENGTH: 18
<212> TYPE: PRT
<213> ORGANISM: Mycobacterium tuberculosis

<400> SEQUENCE: 26

Cys Ala Val Val Leu Ala Thr Met Pro Pro Leu Leu Ser Ala Ile Ala
1               5                   10                  15

Asn Ala

<210> SEQ ID NO 27
<211> LENGTH: 1974
<212> TYPE: DNA
<213> ORGANISM: Mycobacterium tuberculosis

<400> SEQUENCE: 27
atgaccttga ccgcttgtga agtaactgcc gcggaggctc ctttcgaccg cgtttcaaag    60
accattcccc acccattgag ctggggagcc gcgctgtggt cggtagtctc cgtgcgctgg   120
gccaccgtgg cgctgctgct gtttctcgcc ggactagtgg cgcaactgaa cggtgctccc   180
gaggccatgt ggtggacgct ttacctggcc tgttatctgg ccggcggctg gggctcggca   240
tgggcgggcg cacaagcgtt gcggaacaag gcacttgatg tggatctgct gatgattgcc   300
gcggcggtcg gagcggtcgc gattgggcag atcttcgacg gcgcgctgct gatcgtgatc   360
ttcgccacgt ccggtgcgct ggatgacatt gccaccagac acaccgcgga atcggtcaaa   420
ggcctgctgg acctcgcgcc ggatcaggcg gtggtggtcc agggcgacgg cagcgaacgg   480
gtggtggcgg ccagcgagct ggtggtgggg gaccgggtgg tggtgcggcc ggggaccgg    540 ataccccgcag acggtgcggt gctgtcgggg gctagcgacg tcgaccaacg ctcgatcacc   600
ggtgaatcga tgccggtggc caaggcccgc ggtgacgagg tgttcgccgg caccgtgaac   660
ggatcgggtg tattgcatct ggtggtcacc cgtgacccga ccagaccgt ggtagcccgc    720 atcgtcgaac tggtcgccga cgcttcggcg acgaaggcca aaacccaact gttcattgag   780
aaaatcgagc aacgctactc cctgggcatg gtcgcggcca cccttgccct catcgttatt    840
ccgctgatgt tcggcgccga cctgcggccg gtgctgctgc gcgccatgac cttcatgatc    900
gtggcatcgc catgcgcggt ggtgctggcc accatgccgc cgctgctttc ggcgatcgcc    960
aacgcaggcc gtcatggggt gctggtcaaa tccgcggtgg tcgtcgaacg cctggccgat   1020
```

-continued

```
accagcatcg tcgctttgga caagaccggt acgctgaccc gtggcatccc gcgactggct  1080
tccgtcgcac cgctggaccc caacgtggtc gatgcccggc gattgttgca attggcagct  1140
gccgcagaac aatccagcga gcacccgctt ggccgggcga tcgtcgcgga agctcgtcgg  1200
cgtggtatcg ccataccgcc cgccaaggac ttccgcgcgg tcccgggctg cggggtccac  1260
gccctggtgg gcaacgattt cgtcgagatc gccagcccgc aaagctaccg cggtgcaccg  1320
ctagcagagc tggcgccgct cctttctgcc ggcgccactg ccgccatcgt cttgttggat  1380
ggagttgcca tcggtgtgct cgggctcacc gatcagcttc gtccggatgc cgtggagtcc  1440
gtcgcggcga tggctgcatt gaccgccgca ccaccggtgc tgctcacggg tgacaacggg  1500
cgagcggctt ggcgggtcgc tcggaacgcc gggatcaccg atgtgcgagc cgcattgctg  1560
cccgagcaga aggttgaagt cgtgcgcaac ctgcaggccg tggtcacca ggtgctgctc   1620 gtcggcgacg cgtcaacga cgctcccgcc atggccgccg cccgcgccgc tgtcgccatg   1680
ggcgccggcg ccgatctgac cctacagacc gcagacgggg tgaccatacg ggacgaactg  1740
cacaccatcc cgacgatcat cgggttggca cggcaggcgc gccgggtggt caccgtcaac  1800
ctggccatcg cggccacctt catcgccgtc ctggtgctgt gggacttttt tgggcagctg  1860
ccgctgccac tgggtgtggt gggtcacgaa gggtccactg tgctggtggc cctcaacggc  1920
atgcggctat tgaccaaccg gtcgtggcgg gccgcggctt cggctgcgcg ttag        1974
```

<210> SEQ ID NO 28
<211> LENGTH: 657
<212> TYPE: PRT
<213> ORGANISM: Mycobacterium tuberculosis

<400> SEQUENCE: 28

```
Met Thr Leu Thr Ala Cys Glu Val Thr Ala Ala Glu Ala Pro Phe Asp
1               5                   10                  15

Arg Val Ser Lys Thr Ile Pro His Pro Leu Ser Trp Gly Ala Ala Leu
            20                  25                  30

Trp Ser Val Val Ser Val Arg Trp Ala Thr Val Ala Leu Leu Leu Phe
        35                  40                  45

Leu Ala Gly Leu Val Ala Gln Leu Asn Gly Ala Pro Glu Ala Met Trp
    50                  55                  60

Trp Thr Leu Tyr Leu Ala Cys Tyr Leu Ala Gly Trp Gly Ser Ala
65                  70                  75                  80

Trp Ala Gly Ala Gln Ala Leu Arg Asn Lys Ala Leu Asp Val Asp Leu
                85                  90                  95

Leu Met Ile Ala Ala Val Gly Ala Val Ala Ile Gly Gln Ile Phe
            100                 105                 110

Asp Gly Ala Leu Leu Ile Val Ile Phe Ala Thr Ser Gly Ala Leu Asp
        115                 120                 125

Asp Ile Ala Thr Arg His Thr Ala Glu Ser Val Lys Gly Leu Leu Asp
    130                 135                 140

Leu Ala Pro Asp Gln Ala Val Val Gln Gly Asp Gly Ser Glu Arg
145                 150                 155                 160

Val Val Ala Ala Ser Glu Leu Val Val Gly Asp Arg Val Val Arg
                165                 170                 175

Pro Gly Asp Arg Ile Pro Ala Asp Gly Ala Val Leu Ser Gly Ala Ser
            180                 185                 190

Asp Val Asp Gln Arg Ser Ile Thr Gly Glu Ser Met Pro Val Ala Lys
        195                 200                 205
```

```
Ala Arg Gly Asp Glu Val Phe Ala Gly Thr Val Asn Gly Ser Gly Val
    210                 215                 220

Leu His Leu Val Val Thr Arg Asp Pro Ser Gln Thr Val Val Ala Arg
225                 230                 235                 240

Ile Val Glu Leu Val Ala Asp Ala Ser Ala Thr Lys Ala Lys Thr Gln
                245                 250                 255

Leu Phe Ile Glu Lys Ile Glu Gln Arg Tyr Ser Leu Gly Met Val Ala
                260                 265                 270

Ala Thr Leu Ala Leu Ile Val Ile Pro Leu Met Phe Gly Ala Asp Leu
            275                 280                 285

Arg Pro Val Leu Leu Arg Ala Met Thr Phe Met Ile Val Ala Ser Pro
290                 295                 300

Cys Ala Val Val Leu Ala Thr Met Pro Pro Leu Leu Ser Ala Ile Ala
305                 310                 315                 320

Asn Ala Gly Arg His Gly Val Leu Val Lys Ser Ala Val Val Glu
                325                 330                 335

Arg Leu Ala Asp Thr Ser Ile Val Ala Leu Asp Lys Thr Gly Thr Leu
                340                 345                 350

Thr Arg Gly Ile Pro Arg Leu Ala Ser Val Ala Pro Leu Asp Pro Asn
        355                 360                 365

Val Val Asp Ala Arg Arg Leu Leu Gln Leu Ala Ala Ala Glu Gln
    370                 375                 380

Ser Ser Glu His Pro Leu Gly Arg Ala Ile Val Ala Glu Ala Arg Arg
385                 390                 395                 400

Arg Gly Ile Ala Ile Pro Pro Ala Lys Asp Phe Arg Ala Val Pro Gly
                405                 410                 415

Cys Gly Val His Ala Leu Val Gly Asn Asp Phe Val Glu Ile Ala Ser
                420                 425                 430

Pro Gln Ser Tyr Arg Gly Ala Pro Leu Ala Glu Leu Ala Pro Leu Leu
            435                 440                 445

Ser Ala Gly Ala Thr Ala Ala Ile Val Leu Leu Asp Gly Val Ala Ile
450                 455                 460

Gly Val Leu Gly Leu Thr Asp Gln Leu Arg Pro Asp Ala Val Glu Ser
465                 470                 475                 480

Val Ala Ala Met Ala Ala Leu Thr Ala Ala Pro Pro Val Leu Leu Thr
                485                 490                 495

Gly Asp Asn Gly Arg Ala Ala Trp Arg Val Ala Arg Asn Ala Gly Ile
                500                 505                 510

Thr Asp Val Arg Ala Ala Leu Leu Pro Glu Gln Lys Val Glu Val Val
            515                 520                 525

Arg Asn Leu Gln Ala Gly Gly His Gln Val Leu Leu Val Gly Asp Gly
530                 535                 540

Val Asn Asp Ala Pro Ala Met Ala Ala Ala Arg Ala Ala Val Ala Met
545                 550                 555                 560

Gly Ala Gly Ala Asp Leu Thr Leu Gln Thr Ala Asp Gly Val Thr Ile
                565                 570                 575

Arg Asp Glu Leu His Thr Ile Pro Thr Ile Gly Leu Ala Arg Gln
            580                 585                 590

Ala Arg Arg Val Val Thr Val Asn Leu Ala Ile Ala Ala Thr Phe Ile
        595                 600                 605

Ala Val Leu Val Leu Trp Asp Leu Phe Gly Gln Leu Pro Leu Pro Leu
    610                 615                 620

Gly Val Val Gly His Glu Gly Ser Thr Val Leu Val Ala Leu Asn Gly
625                 630                 635                 640
```

```
Met Arg Leu Leu Thr Asn Arg Ser Trp Arg Ala Ala Ser Ala Ala
                645                 650                 655

Arg

<210> SEQ ID NO 29
<211> LENGTH: 27
<212> TYPE: DNA
<213> ORGANISM: Mycobacterium tuberculosis

<400> SEQUENCE: 29
atggtgatca tagagctgat gcgccgg                                             27

<210> SEQ ID NO 30
<211> LENGTH: 9
<212> TYPE: PRT
<213> ORGANISM: Mycobacterium tuberculosis

<400> SEQUENCE: 30

Met Val Ile Ile Glu Leu Met Arg Arg
1               5

<210> SEQ ID NO 31
<211> LENGTH: 996
<212> TYPE: DNA
<213> ORGANISM: Mycobacterium tuberculosis

<400> SEQUENCE: 31
atggtgatca tagagctgat gcgccgggtg gtaggtctcg cacagggagc taccgccgag         60
gtcgccgtct atggcgaccg agatcgtgat ctcgcggagc gatggtgcgc gaacaccgga        120
aacaccctgg tgcgcgccga cgtggaccag accggcgtcg gcaccctggt ggtgcgccgc        180
ggccatccgc ctgacccggc aagcgtgttg gccccgacc ggctaccgg gtccggttg          240 tggctgtaca ccaacttcca ctgcaacctg tgctgcgact actgctgcgt ctcgtcgtca        300
ccaagcaccc cgcatcgcga actggggggcg gagcggatcg gccgaatcgt cggtgaagcg       360
gcgcgctggg gagtgcgcga actgttcctc accggcggtg agccgttcct gctgcccgac       420
atcgacacga tcatcgcgac ctgtgtgaag cagttgccca ccaccgtcct caccaacggc       480
atggtgttca aagggcgggg tcggcgcgcg ctggaatccc tacctagagg gctcgccttg        540
cagatcagcc tggactcggc caccccggag ctgcacgatg cgcaccgcgg cgcggggacg        600
tgggtcaagg cagtagctgg tatccggttg gcgctctcac ttggcttccg ggtgcgggtg        660
gccgcgacgg ttgccagccc cgcacctggc gagctgacgg cgtttcacga cttcctcgac        720
gggcttggca tcgcacccgg ggatcagctg gtccggccga tcgcgctgga gggcgccgcg        780
tcgcaagggg tggcgctcac ccgcgaatcg ctggttcccg aggtgaccgt caccgccgac        840
ggcgtgtact ggcacccagt ggccgccacc gacgagcgcg ccctggtcac ccgtaccgtc        900
gaacccttga ccccggcgct ggacatggta agccggctat cgccgaaca gtggacacga        960 gccgccgaag aggccgcgtt gttcccgtgt gcgtag                                  996

<210> SEQ ID NO 32
<211> LENGTH: 331
<212> TYPE: PRT
<213> ORGANISM: Mycobacterium tuberculosis

<400> SEQUENCE: 32

Met Val Ile Ile Glu Leu Met Arg Arg Val Val Gly Leu Ala Gln Gly
1               5                   10                  15
```

```
Ala Thr Ala Glu Val Ala Val Tyr Gly Asp Arg Asp Arg Asp Leu Ala
            20                  25                  30

Glu Arg Trp Cys Ala Asn Thr Gly Asn Thr Leu Val Arg Ala Asp Val
        35                  40                  45

Asp Gln Thr Gly Val Gly Thr Leu Val Val Arg Arg Gly His Pro Pro
    50                  55                  60

Asp Pro Ala Ser Val Leu Gly Pro Asp Arg Leu Pro Gly Val Arg Leu
65                  70                  75                  80

Trp Leu Tyr Thr Asn Phe His Cys Asn Leu Cys Cys Asp Tyr Cys Cys
                85                  90                  95

Val Ser Ser Pro Ser Thr Pro His Arg Glu Leu Gly Ala Glu Arg
                100                 105                 110

Ile Gly Arg Ile Val Gly Glu Ala Ala Arg Trp Gly Val Arg Glu Leu
            115                 120                 125

Phe Leu Thr Gly Gly Glu Pro Phe Leu Leu Pro Asp Ile Asp Thr Ile
        130                 135                 140

Ile Ala Thr Cys Val Lys Gln Leu Pro Thr Thr Val Leu Thr Asn Gly
145                 150                 155                 160

Met Val Phe Lys Gly Arg Gly Arg Arg Ala Leu Glu Ser Leu Pro Arg
                165                 170                 175

Gly Leu Ala Leu Gln Ile Ser Leu Asp Ser Ala Thr Pro Glu Leu His
            180                 185                 190

Asp Ala His Arg Gly Ala Gly Thr Trp Val Lys Ala Val Ala Gly Ile
        195                 200                 205

Arg Leu Ala Leu Ser Leu Gly Phe Arg Val Arg Val Ala Ala Thr Val
210                 215                 220

Ala Ser Pro Ala Pro Gly Glu Leu Thr Ala Phe His Asp Phe Leu Asp
225                 230                 235                 240

Gly Leu Gly Ile Ala Pro Gly Asp Gln Leu Val Arg Pro Ile Ala Leu
                245                 250                 255

Glu Gly Ala Ala Ser Gln Gly Val Ala Leu Thr Arg Glu Ser Leu Val
            260                 265                 270

Pro Glu Val Thr Val Thr Ala Asp Gly Val Tyr Trp His Pro Val Ala
        275                 280                 285

Ala Thr Asp Glu Arg Ala Leu Val Thr Arg Thr Val Glu Pro Leu Thr
290                 295                 300

Pro Ala Leu Asp Met Val Ser Arg Leu Phe Ala Glu Gln Trp Thr Arg
305                 310                 315                 320

Ala Ala Glu Glu Ala Ala Leu Phe Pro Cys Ala
                325                 330

<210> SEQ ID NO 33
<211> LENGTH: 57
<212> TYPE: DNA
<213> ORGANISM: Mycobacterium tuberculosis

<400> SEQUENCE: 33
cgtgccaccg cagaccagat cggcacgcag acaacgcaaa tcgcggccat caaagcc     57

<210> SEQ ID NO 34
<211> LENGTH: 19
<212> TYPE: PRT
<213> ORGANISM: Mycobacterium tuberculosis

<400> SEQUENCE: 34

Arg Ala Thr Ala Asp Gln Ile Gly Thr Gln Thr Thr Gln Ile Ala Ala
1               5                   10                  15
```

Ile Lys Ala

<210> SEQ ID NO 35
<211> LENGTH: 1140
<212> TYPE: DNA
<213> ORGANISM: Mycobacterium tuberculosis

<400> SEQUENCE: 35

| | |
|---|---|
| atgacgatct ccgatgtacc cacccagacg ctgcccgccg aaggcgaaat cggcctgata | 60 |
| gacgtcggct cgctgcaact ggaaagcggg gcggtgatcg acgatgtctg tatcgccgtg | 120 |
| caacgctggg gcaaattgtc gcccgcacgg acaacgtgg tggtggtctt gcacgcgctc | 180 |
| accggcgact cgcacatcac tggacccgcc ggacccggcc accccacccc cggctggtgg | 240 |
| gacggggtgg ccgggccgag tgcgccgatt gacaccaccc gctggtgcgc ggtagctacc | 300 |
| aatgtgctcg gcggctgccg cggctccacc gggcccagct cgcttgcccg cgacggaaag | 360 |
| ccttggggct caagatttcc gctgatctcg atacgtgacc aggtgcaggc ggacgtcgcg | 420 |
| gcgctggccg cgctgggcat caccgaggtc gccgccgtcg tcggcggctc catgggcggc | 480 |
| gcccgggccc tggaatgggt ggtcggctac ccggatcggg tccgagccgg attgctgctg | 540 |
| gcggcggtcg gtcgtgccac cgcagaccag atcggcacgc agacaacgca atcgcggcc | 600 |
| atcaaagccg accggactg gcagagcggc gactaccacg agacggggag ggcaccagac | 660 |
| gccgggctgc gactcgcccg ccgcttcgcg cacctcacct accgcggcga atcgagctc | 720 |
| gacacccggt tcgccaacca caaccagggc aacgaggatc cgacgccgg cgggcgctac | 780 |
| gcggtgcaaa gttatctgga acaccaagga gacaaactgt tatcccggtt cgacgccggc | 840 |
| agctacgtga ttctcaccga ggcgctcaac agccacgacg tcggccgcgg ccgcggcggg | 900 |
| gtctccgcgg ctctgcgcgc ctgcccggtg ccggtggtgg tgggcggcat cacctccgac | 960 |
| cggctctacc cgctgcgcct gcagcaggag ctggccgacc tgctgccggg ctgcgccggg | 1020 |
| ctgcgagtcg tcgagtcggt ctacggacac gacggcttcc tggtggaaac cgaggccgtg | 1080 |
| ggcgaattga tccgccagac actgggattg ctgatcgtg aaggcgcgtg tcggcggtga | 1140 |

<210> SEQ ID NO 36
<211> LENGTH: 379
<212> TYPE: PRT
<213> ORGANISM: Mycobacterium tuberculosis

<400> SEQUENCE: 36

Met Thr Ile Ser Asp Val Pro Thr Gln Thr Leu Pro Ala Glu Gly Glu
1               5                   10                  15

Ile Gly Leu Ile Asp Val Gly Ser Leu Gln Leu Glu Ser Gly Ala Val
            20                  25                  30

Ile Asp Asp Val Cys Ile Ala Val Gln Arg Trp Gly Lys Leu Ser Pro
        35                  40                  45

Ala Arg Asp Asn Val Val Val Leu His Ala Leu Thr Gly Asp Ser
    50                  55                  60

His Ile Thr Gly Pro Ala Gly Pro Gly His Pro Thr Pro Gly Trp Trp
65                  70                  75                  80

Asp Gly Val Ala Gly Pro Ser Ala Pro Ile Asp Thr Thr Arg Trp Cys
                85                  90                  95

Ala Val Ala Thr Asn Val Leu Gly Gly Cys Arg Gly Ser Thr Gly Pro
            100                 105                 110

Ser Ser Leu Ala Arg Asp Gly Lys Pro Trp Gly Ser Arg Phe Pro Leu
        115                 120                 125

```
Ile Ser Ile Arg Asp Gln Val Gln Ala Asp Val Ala Ala Leu Ala Ala
    130                 135                 140

Leu Gly Ile Thr Glu Val Ala Ala Val Val Gly Ser Met Gly Gly
145                 150                 155                 160

Ala Arg Ala Leu Glu Trp Val Val Gly Tyr Pro Asp Arg Val Arg Ala
                165                 170                 175

Gly Leu Leu Leu Ala Val Gly Ala Arg Ala Thr Ala Asp Gln Ile Gly
            180                 185                 190

Thr Gln Thr Thr Gln Ile Ala Ala Ile Lys Ala Asp Pro Asp Trp Gln
            195                 200                 205

Ser Gly Asp Tyr His Glu Thr Gly Arg Ala Pro Asp Ala Gly Leu Arg
210                 215                 220

Leu Ala Arg Arg Phe Ala His Leu Thr Tyr Arg Gly Glu Ile Glu Leu
225                 230                 235                 240

Asp Thr Arg Phe Ala Asn His Asn Gln Gly Asn Glu Asp Pro Thr Ala
                245                 250                 255

Gly Gly Arg Tyr Ala Val Gln Ser Tyr Leu Glu His Gln Gly Asp Lys
            260                 265                 270

Leu Leu Ser Arg Phe Asp Ala Gly Ser Tyr Val Ile Leu Thr Glu Ala
            275                 280                 285

Leu Asn Ser His Asp Val Gly Arg Gly Arg Gly Val Ser Ala Ala
290                 295                 300

Leu Arg Ala Cys Pro Val Pro Val Val Gly Ile Thr Ser Asp
305                 310                 315                 320

Arg Leu Tyr Pro Leu Arg Leu Gln Gln Glu Leu Ala Asp Leu Leu Pro
                325                 330                 335

Gly Cys Ala Gly Leu Arg Val Val Glu Ser Val Tyr Gly His Asp Gly
            340                 345                 350

Phe Leu Val Glu Thr Glu Ala Val Gly Glu Leu Ile Arg Gln Thr Leu
            355                 360                 365

Gly Leu Ala Asp Arg Glu Gly Ala Cys Arg Arg
    370                 375

<210> SEQ ID NO 37
<211> LENGTH: 57
<212> TYPE: DNA
<213> ORGANISM: Mycobacterium tuberculosis

<400> SEQUENCE: 37
cgcaccgccg aggaacgcgc caacgcggtt cgcgggcggg ccgattcgct gcgccgt     57

<210> SEQ ID NO 38
<211> LENGTH: 19
<212> TYPE: PRT
<213> ORGANISM: Mycobacterium tuberculosis

<400> SEQUENCE: 38

Arg Thr Ala Glu Glu Arg Ala Asn Ala Val Arg Gly Arg Ala Asp Ser
1               5                   10                  15

Leu Arg Arg

<210> SEQ ID NO 39
<211> LENGTH: 3618
<212> TYPE: DNA
<213> ORGANISM: Mycobacterium tuberculosis

<400> SEQUENCE: 39
```

-continued

```
gtgtacctca agagtctgac gttgaagggc ttcaagtcct tcgccgcgcc gacgacttta    60
cgcttcgagc cgggcattac ggccgtcgtt gggcccaacg gctccggcaa atccaatgtg   120
gtcgatgccc tggcgtgggt gatggggag caggggcaa agacgctgcg cggcggcaag    180
atggaagacg tcatcttcgc cggcacctcg tcgcgtgcgc cgctgggccg cgccgaagtc   240
accgttagca tcgacaactc cgacaacgca ctgcctatcg aatacaccga ggtgtcgatc   300
acccgaagaa tgtttcgcga cggtgccagc gaatacgaaa tcaacggcag cagttgccgt   360
ttgatggatg tgcaggagtt gctgagcgac tccggcatcg gccgtgagat gcatgtgatt   420
gttgggcaag ggaagctcga ggagatcttg cagtcgcggc ctgaggatcg gcgggcgttc   480
atcgaggaag ccgccggtgt gctcaagcat cgcaagcgca aggaaaaagc tctgcgcaaa   540
ctcgacacga tggcggcgaa cctggccggg ctcaccgatc tgaccaccga gctccggcgt   600
caactcaaac cgctgggccg gcaggccgag gcggcccagc gtgccgcggc catccaagcc   660
gatctgcgcg acgccggct cgcgcctggcg gccgacgact tggtaagccg cagagccgaa   720
cgggaagcgg tctttcaggc cgaggctgcg atgcgccgcg agcatgacga ggccgccgcc   780
cggctggcg tggcatccga ggagctggcc gcgcatgagt ccgcggtcgc cgaactctcg   840
acgcgggccg agtcgatcca gcacacttgg ttcgggctgt ctgcgctggc cgaacgggtg   900
gacgctacgg tgcgcatcgc cagcgaacgc gcccatcatc tcgatatcga gccggtagcg   960
gtcagcgaca ccgaccccag aaagcccgag gagctagaag ccgaggccca gcaggtggcc  1020
gtcgccgagc aacaactgtt agcggagctg gacgcggcgc gtgcccgact cgatgctgcc  1080
cgtgcagagc tggccgaccg ggagcgccgc gccgccgagg ccgaccgggc acacctggcg  1140
gcggtccggg aggaggcgga ccgccgtgag ggactggcgc ggctggctgg ccaggtggag  1200
accatgcggg cgcgtgtcga atcgatcgat gagagcgtgg cacggttgtc cgagcggatc  1260
gaggatgccg caatgcgcgc ccagcagacc cgagccgagt tcgaaaccgt gcagggccgc  1320
atcggtgaac tggatcaagg cgaggtcggc ctggatgagc accacgagcg tactgtggcc  1380
gcgttgcggt tggccgacga acgcgtcgcc gagctgcaat ccgccgaacg cgccgccgaa  1440
cgccaggtgg catcgctacg ggctcgcatc gatgcgctcg cagtggggct acagcgcaag  1500
gacggcgcgg cgtggctggc gcacaatcgc agtggcgcag ggcttttcgg ttcgatcgcc  1560
caattggtga aggtacgttc cggctatgaa gcggcactgg ccgcggcgct cgggccggcg  1620
gccgacgcac ttgcggtgga cggcctgact gccgcgggta gtgccgtcag cgcactcaaa  1680
caagccgacg gcggtcgcgc ggtcctcgtg ctgagtgact ggccggcccc gcaagccccc  1740
caatccgcct cgggggagat gctgcctagc ggcgcccagt gggccctaga cctggtcgag  1800
tctccaccgc agttggttgg cgcgatgatc gccatgcttt cgggtgtcgc ggtggtcaac  1860
gacctgactg aggcaatggg cctggtcgag attcgtccgg agctacgcgc ggtcaccgtt  1920
gacggtgatc tggtgggcgc cggctgggtc agcggcggat cggaccgcaa gctgtccacc  1980
ttggaggtca cctccgagat cgacaaggcc aggagtgagc tggccgctgc cgaggcgctg  2040
gcggcgcaat tgaatgcggc cctggccggt gcgctgaccg agcagtccgc ccgccaggac  2100
gcggccgagc aagccttggc cgcgcttaac gaatccgaca cggccatctc ggcgatgtac  2160
gagcagctgg gccgcctcgg gcaggaggcc cgcgcggcgc aagaagagtg gaaccggttg  2220
ctgcagcagc gtacggaaca ggaagccgtg cgcacacaga ctctcgacga cgtcatacaa  2280
cttgagaccc agctgcgtaa ggcccaggag acccaacggg tgcaggtggc ccaaccgatc  2340
gaccgccagg cgatcagtgc cgctgccgat cgcgcccgcg gtgtcgaagt ggaagcccgg  2400
```

-continued

```
ctggcggtgc gcaccgccga ggaacgcgcc aacgcggttc gcgggcgggc cgattcgctg    2460
cgccgtgcgg cagcggcgga acgtgaggcg cgggtgcggg ctcagcaagc acgcgccgca    2520
agactgcatg cggccgcggt ggccgcagcg gtcgccgact gcggacggct gctggccggg    2580
cggttgcacc gggcggtgga cggggcgtcg caactgcgcg acgcgtcggc cgcgcaacgt    2640
cagcagcggt tagcggcgat ggccgcggtg cgcgacgagg tgaacacgct gagcgcccga    2700 gtggggggaac tcaccgattc gctgcaccgc gacgagctgg ctaacgcgca ggcggcgctg    2760
cgtatcgagc agcttgagca gatggtgcta gagcagttcg gaatggcgcc ggccgacttg    2820
atcaccgaat acggtccaca tgtggcgcta ccaccgaccg agctcgagat ggctgagttc    2880
gagcaagccc gcgaacgcgg cgagcaggtg attgcgcccg ccccatgcc gttcgaccgg      2940 gttacccagg agcgccgggc caaacgcgcc gagcgtgcgc ttgccgagtt gggcagggtc    3000
aacccgctgg cgctcgaaga gtttgctgcc ttggaggagc gctacaattt cctgtccacc    3060
caactcgagg atgtcaaggc tgcccgcaag gatctgctgg gcgtcgtcgc cgatgttgac    3120
gcccgcatcc tgcaggtgtt caatgacgcg ttcgtagacg tggaacgcga atttcgcggc    3180
gtgttcaccg cattgttccc cggtggtgaa ggacggctgc ggctgaccga gcccgacgac    3240
atgctcacca ccggcatcga ggtcgaagcc cgcccgccgg gcaagaagat tacccgactg    3300
tctttgctct ccggtggcga gaaggcgctg accgcggtgg cgatgctggt cgcgatcttt    3360
cgtgcccgtc catcgccgtt ctacatcatg gacgaggtgg aggccgccct cgacgacgtg    3420
aacctgcgcc gactgctcag cctgttcgaa cagctgcgag agcagtcgca gatcatcatc    3480
atcacccacc agaagccgac gatggaggtc gcggacgcac tgtacggcgt aaccatgcag    3540
aacgacggca tcaccgcggt catctcgcag cgcatgcgcg tcagcaggt ggatcagctg      3600 gttaccaatt cctcgtag                                                    3618
```

<210> SEQ ID NO 40
<211> LENGTH: 1205
<212> TYPE: PRT
<213> ORGANISM: Mycobacterium tuberculosis

<400> SEQUENCE: 40

```
Met Tyr Leu Lys Ser Leu Thr Leu Lys Gly Phe Lys Ser Phe Ala Ala
1               5                   10                  15

Pro Thr Thr Leu Arg Phe Glu Pro Gly Ile Thr Ala Val Val Gly Pro
            20                  25                  30

Asn Gly Ser Gly Lys Ser Asn Val Val Asp Ala Leu Ala Trp Val Met
        35                  40                  45

Gly Glu Gln Gly Ala Lys Thr Leu Arg Gly Gly Lys Met Glu Asp Val
    50                  55                  60

Ile Phe Ala Gly Thr Ser Ser Arg Ala Pro Leu Gly Arg Ala Glu Val
65                  70                  75                  80

Thr Val Ser Ile Asp Asn Ser Asp Asn Ala Leu Pro Ile Glu Tyr Thr
                85                  90                  95

Glu Val Ser Ile Thr Arg Arg Met Phe Arg Asp Gly Ala Ser Glu Tyr
            100                 105                 110

Glu Ile Asn Gly Ser Ser Cys Arg Leu Met Asp Val Gln Glu Leu Leu
        115                 120                 125

Ser Asp Ser Gly Ile Gly Arg Glu Met His Val Ile Val Gly Gln Gly
    130                 135                 140

Lys Leu Glu Glu Ile Leu Gln Ser Arg Pro Glu Asp Arg Arg Ala Phe
145                 150                 155                 160
```

```
Ile Glu Glu Ala Ala Gly Val Leu Lys His Arg Lys Arg Lys Glu Lys
                165                 170                 175
Ala Leu Arg Lys Leu Asp Thr Met Ala Asn Leu Ala Arg Leu Thr
        180                 185                 190
Asp Leu Thr Thr Glu Leu Arg Arg Gln Leu Lys Pro Leu Gly Arg Gln
        195                 200                 205
Ala Glu Ala Ala Gln Arg Ala Ala Ile Gln Ala Asp Leu Arg Asp
    210                 215                 220
Ala Arg Leu Arg Leu Ala Ala Asp Asp Leu Val Ser Arg Ala Glu
225                 230                 235                 240
Arg Glu Ala Val Phe Gln Ala Glu Ala Met Arg Arg Glu His Asp
                245                 250                 255
Glu Ala Ala Ala Arg Leu Ala Val Ala Ser Glu Glu Leu Ala Ala His
            260                 265                 270
Glu Ser Ala Val Ala Glu Leu Ser Thr Arg Ala Glu Ser Ile Gln His
        275                 280                 285
Thr Trp Phe Gly Leu Ser Ala Leu Ala Glu Arg Val Asp Ala Thr Val
        290                 295                 300
Arg Ile Ala Ser Glu Arg Ala His His Leu Asp Ile Glu Pro Val Ala
305                 310                 315                 320
Val Ser Asp Thr Asp Pro Arg Lys Pro Glu Glu Leu Glu Ala Glu Ala
                325                 330                 335
Gln Gln Val Ala Val Ala Glu Gln Gln Leu Leu Ala Glu Leu Asp Ala
            340                 345                 350
Ala Arg Ala Arg Leu Asp Ala Ala Arg Ala Glu Leu Ala Asp Arg Glu
        355                 360                 365
Arg Arg Ala Ala Glu Ala Asp Arg Ala His Leu Ala Ala Val Arg Glu
        370                 375                 380
Glu Ala Asp Arg Arg Glu Gly Leu Ala Arg Leu Ala Gly Gln Val Glu
385                 390                 395                 400
Thr Met Arg Ala Arg Val Glu Ser Ile Asp Glu Ser Val Ala Arg Leu
                405                 410                 415
Ser Glu Arg Ile Glu Asp Ala Ala Met Arg Ala Gln Gln Thr Arg Ala
            420                 425                 430
Glu Phe Glu Thr Val Gln Gly Arg Ile Gly Glu Leu Asp Gln Gly Glu
        435                 440                 445
Val Gly Leu Asp Glu His His Glu Arg Thr Val Ala Ala Leu Arg Leu
        450                 455                 460
Ala Asp Glu Arg Val Ala Glu Leu Gln Ser Ala Glu Arg Ala Ala Glu
465                 470                 475                 480
Arg Gln Val Ala Ser Leu Arg Ala Arg Ile Asp Ala Leu Ala Val Gly
                485                 490                 495
Leu Gln Arg Lys Asp Gly Ala Ala Trp Leu Ala His Asn Arg Ser Gly
            500                 505                 510
Ala Gly Leu Phe Gly Ser Ile Ala Gln Leu Val Lys Val Arg Ser Gly
        515                 520                 525
Tyr Glu Ala Ala Leu Ala Ala Leu Gly Pro Ala Ala Asp Ala Leu
        530                 535                 540
Ala Val Asp Gly Leu Thr Ala Gly Ser Ala Val Ser Ala Leu Lys
545                 550                 555                 560
Gln Ala Asp Gly Gly Arg Ala Val Leu Val Leu Ser Asp Trp Pro Ala
                565                 570                 575
Pro Gln Ala Pro Gln Ser Ala Ser Gly Glu Met Leu Pro Ser Gly Ala
            580                 585                 590
```

```
Gln Trp Ala Leu Asp Leu Val Glu Ser Pro Gln Leu Val Gly Ala
        595                 600                 605

Met Ile Ala Met Leu Ser Gly Val Ala Val Val Asn Asp Leu Thr Glu
610                 615                 620

Ala Met Gly Leu Val Glu Ile Arg Pro Glu Leu Arg Ala Val Thr Val
625                 630                 635                 640

Asp Gly Asp Leu Val Gly Ala Gly Trp Val Ser Gly Gly Ser Asp Arg
                    645                 650                 655

Lys Leu Ser Thr Leu Glu Val Thr Ser Glu Ile Asp Lys Ala Arg Ser
                660                 665                 670

Glu Leu Ala Ala Ala Glu Ala Leu Ala Ala Gln Leu Asn Ala Ala Leu
    675                 680                 685

Ala Gly Ala Leu Thr Glu Gln Ser Ala Arg Gln Asp Ala Ala Glu Gln
    690                 695                 700

Ala Leu Ala Ala Leu Asn Glu Ser Asp Thr Ala Ile Ser Ala Met Tyr
705                 710                 715                 720

Glu Gln Leu Gly Arg Leu Gly Gln Glu Ala Arg Ala Ala Glu Glu Glu
                725                 730                 735

Trp Asn Arg Leu Leu Gln Arg Thr Glu Gln Glu Ala Val Arg Thr
                740                 745                 750

Gln Thr Leu Asp Asp Val Ile Gln Leu Glu Thr Gln Leu Arg Lys Ala
        755                 760                 765

Gln Glu Thr Gln Arg Val Gln Val Ala Gln Pro Ile Asp Arg Gln Ala
    770                 775                 780

Ile Ser Ala Ala Ala Asp Arg Ala Arg Gly Val Glu Val Glu Ala Arg
785                 790                 795                 800

Leu Ala Val Arg Thr Ala Glu Glu Arg Ala Asn Ala Val Arg Gly Arg
                805                 810                 815

Ala Asp Ser Leu Arg Arg Ala Ala Ala Glu Arg Glu Ala Arg Val
                820                 825                 830

Arg Ala Gln Gln Ala Arg Ala Ala Arg Leu His Ala Ala Val Ala
    835                 840                 845

Ala Ala Val Ala Asp Cys Gly Arg Leu Leu Ala Gly Arg Leu His Arg
    850                 855                 860

Ala Val Asp Gly Ala Ser Gln Leu Arg Asp Ala Ser Ala Ala Gln Arg
865                 870                 875                 880

Gln Gln Arg Leu Ala Ala Met Ala Ala Val Arg Asp Glu Val Asn Thr
                885                 890                 895

Leu Ser Ala Arg Val Gly Glu Leu Thr Asp Ser Leu His Arg Asp Glu
                900                 905                 910

Leu Ala Asn Ala Gln Ala Ala Leu Arg Ile Glu Gln Leu Glu Gln Met
        915                 920                 925

Val Leu Glu Gln Phe Gly Met Ala Pro Ala Asp Leu Ile Thr Glu Tyr
    930                 935                 940

Gly Pro His Val Ala Leu Pro Pro Thr Glu Leu Glu Met Ala Glu Phe
945                 950                 955                 960

Glu Gln Ala Arg Glu Arg Gly Glu Gln Val Ile Ala Pro Ala Pro Met
                965                 970                 975

Pro Phe Asp Arg Val Thr Gln Glu Arg Arg Ala Lys Arg Ala Glu Arg
                980                 985                 990

Ala Leu Ala Glu Leu Gly Arg Val  Asn Pro Leu Ala Leu  Glu Glu Phe
    995                 1000                1005

Ala Ala  Leu Glu Glu Arg Tyr  Asn Phe Leu Ser Thr  Gln Leu Glu
```

```
                     1010                1015                1020
Asp Val Lys Ala Ala Arg Lys Asp Leu Leu Gly Val  Val Ala Asp
    1025                1030                1035

Val Asp Ala Arg Ile Leu Gln Val Phe Asn Asp Ala  Phe Val Asp
    1040                1045                1050

Val Glu Arg Glu Phe Arg Gly Val Phe Thr Ala Leu  Phe Pro Gly
    1055                1060                1065

Gly Glu Gly Arg Leu Arg Leu Thr Glu Pro Asp Asp  Met Leu Thr
    1070                1075                1080

Thr Gly Ile Glu Val Glu Ala Arg Pro Pro Gly Lys  Lys Ile Thr
    1085                1090                1095

Arg Leu Ser Leu Leu Ser Gly Gly Glu Lys Ala Leu  Thr Ala Val
    1100                1105                1110

Ala Met Leu Val Ala Ile Phe Arg Ala Arg Pro Ser  Pro Phe Tyr
    1115                1120                1125

Ile Met Asp Glu Val Glu Ala Ala Leu Asp Asp Val  Asn Leu Arg
    1130                1135                1140

Arg Leu Leu Ser Leu Phe Glu Gln Leu Arg Glu Gln  Ser Gln Ile
    1145                1150                1155

Ile Ile Ile Thr His Gln Lys Pro Thr Met Glu Val  Ala Asp Ala
    1160                1165                1170

Leu Tyr Gly Val Thr Met Gln Asn Asp Gly Ile Thr  Ala Val Ile
    1175                1180                1185

Ser Gln Arg Met Arg Gly Gln Val Asp Gln Leu  Val Thr Asn
    1190                1195                1200

Ser Ser
    1205

<210> SEQ ID NO 41
<211> LENGTH: 48
<212> TYPE: DNA
<213> ORGANISM: Mycobacterium tuberculosis

<400> SEQUENCE: 41
ctgcacgcgc agaaggcgct gctggtgtgg ctgctggagc gctcatga              48

<210> SEQ ID NO 42
<211> LENGTH: 16
<212> TYPE: PRT
<213> ORGANISM: Mycobacterium tuberculosis

<400> SEQUENCE: 42

Arg Leu His Ala Gln Lys Ala Leu Leu Val Trp Leu Leu Glu Arg Ser
1               5                   10                  15

<210> SEQ ID NO 43
<211> LENGTH: 924
<212> TYPE: DNA
<213> ORGANISM: Mycobacterium tuberculosis

<400> SEQUENCE: 43
gtgatcaggc atttcctgcg cgacgacgat ctgtccccgg ccgaacaggc cgaggtgctc      60
gagctcgcgg ccgagctgaa gaaagacccg gttagccgtc gtcccctgca agggccgcgc     120
ggggtggcgg tcatcttcga caagaactcc acccgcaccc ggttctcctt cgagctgggc     180
atcgcgcagc tgggcgggca tgccgtcgtc gtcgacagcg gcagcaccca gctgggccgc     240
gacgaaaccc tgcaggacac cgcaaaggtg ttgtcccgct acgtcgatgc catcgtctgg     300
```

```
cgaaccttcg gccaagagcg gctggacgcc atggcgtcgg tcgcgacggt gcccgtgatc    360
aacgcgctct ccgatgagtt ccatccgtgt caggtgttgg ccgacctgca gaccatcgcc    420
gaacgcaagg gggcgctgcg cggcctgagg ttgtcctact tcggcgacgg cgccaacaac    480
atggcccact cgctgctgct cggcggggtc accgcgggta tccacgtcac cgtcgcggct    540
cccgagggct tcctgcccga cccgtcggtg cgggccgcgg ccgagcgccg cgcccaggat    600 accgcgcct cggtgactgt gaccgccgac gcccacgcgg ccgccgccgg cgccgacgtt    660
ctggtcaccg acacctggac gtcgatgggc caggaaaacg acgggttgga ccgagtgaag    720
ccgtttcggc cgtttcagct caactcgcga cttctggcgc tggccgactc ggatgccatc    780
gtgttgcatt gcctgccggc ccatcgcggc gacgagatca ccgacgcggt gatggacggg    840
ccggccagcg cggtgtggga cgaggccgaa aaccggctgc acgcgcagaa ggcgctgctg    900
gtgtggctgc tggagcgctc atga                                           924
```

<210> SEQ ID NO 44
<211> LENGTH: 307
<212> TYPE: PRT
<213> ORGANISM: Mycobacterium tuberculosis

<400> SEQUENCE: 44

```
Met Ile Arg His Phe Leu Arg Asp Asp Asp Leu Ser Pro Ala Glu Gln
1               5                   10                  15

Ala Glu Val Leu Glu Leu Ala Ala Glu Leu Lys Lys Asp Pro Val Ser
            20                  25                  30

Arg Arg Pro Leu Gln Gly Pro Arg Gly Val Ala Val Ile Phe Asp Lys
        35                  40                  45

Asn Ser Thr Arg Thr Arg Phe Ser Phe Glu Leu Gly Ile Ala Gln Leu
    50                  55                  60

Gly Gly His Ala Val Val Asp Ser Gly Ser Thr Gln Leu Gly Arg
65                  70                  75                  80

Asp Glu Thr Leu Gln Asp Thr Ala Lys Val Leu Ser Arg Tyr Val Asp
                85                  90                  95

Ala Ile Val Trp Arg Thr Phe Gly Gln Glu Arg Leu Asp Ala Met Ala
            100                 105                 110

Ser Val Ala Thr Val Pro Val Ile Asn Ala Leu Ser Asp Glu Phe His
        115                 120                 125

Pro Cys Gln Val Leu Ala Asp Leu Gln Thr Ile Ala Glu Arg Lys Gly
    130                 135                 140

Ala Leu Arg Gly Leu Arg Leu Ser Tyr Phe Gly Asp Gly Ala Asn Asn
145                 150                 155                 160

Met Ala His Ser Leu Leu Leu Gly Gly Val Thr Ala Gly Ile His Val
                165                 170                 175

Thr Val Ala Ala Pro Glu Gly Phe Leu Pro Asp Pro Ser Val Arg Ala
            180                 185                 190

Ala Ala Glu Arg Arg Ala Gln Asp Thr Gly Ala Ser Val Thr Val Thr
        195                 200                 205

Ala Asp Ala His Ala Ala Ala Gly Ala Asp Val Leu Val Thr Asp
    210                 215                 220

Thr Trp Thr Ser Met Gly Gln Glu Asn Asp Gly Leu Asp Arg Val Lys
225                 230                 235                 240

Pro Phe Arg Pro Phe Gln Leu Asn Ser Arg Leu Leu Ala Leu Ala Asp
                245                 250                 255

Ser Asp Ala Ile Val Leu His Cys Leu Pro Ala His Arg Gly Asp Glu
            260                 265                 270
```

```
Ile Thr Asp Ala Val Met Asp Gly Pro Ala Ser Ala Val Trp Asp Glu
        275                 280                 285

Ala Glu Asn Arg Leu His Ala Gln Lys Ala Leu Leu Val Trp Leu Leu
    290                 295                 300

Glu Arg Ser
305

<210> SEQ ID NO 45
<211> LENGTH: 66
<212> TYPE: DNA
<213> ORGANISM: Mycobacterium tuberculosis

<400> SEQUENCE: 45
cgctggaccg acgaaacctt cggcgacatc ggcggcgccg gcggcggcgt gagcggacat      60
cgcggg                                                                66

<210> SEQ ID NO 46
<211> LENGTH: 22
<212> TYPE: PRT
<213> ORGANISM: Mycobacterium tuberculosis

<400> SEQUENCE: 46

Arg Trp Thr Asp Glu Thr Phe Gly Asp Ile Gly Gly Ala Gly Gly Gly
1               5                   10                  15

Val Ser Gly His Arg Gly
            20

<210> SEQ ID NO 47
<211> LENGTH: 765
<212> TYPE: DNA
<213> ORGANISM: Mycobacterium tuberculosis

<400> SEQUENCE: 47
atgagcggcg agacaaccag gctgaccgaa ccgcaactac gtgagctggc cgcgcgcgga      60
gctgccgaac tcgacggcgc caccgccacc gacatgttgc gctggaccga cgaaaccttc     120
ggcgacatcg gcggcgccgg cggcggcgtg agcggacatc gcgggtggac aacgtgcaac     180
tacgtagttg cttccaacat ggctgatgcg gtgctggtgg atctggccgc caaggtgcga     240
ccgggcgtac cggtcatctt tcttgatacc ggctaccact cgtcgaaac aatcggcacc      300 agagatgcga tcgagtccgt ctatgacgtc cgggtgctca atgtcactcc ggagcacaca     360
gtggccgagc aggacgaact gctgggcaag gacttgttcg cccgcaaccc ccatgaatgc     420
tgccggttgc gcaaggtcgt tcccctgggc aagacgctgc gtggctactc cgcgtgggtg     480
accgggctac ggcgggtcga tgcaccgacc cgggccaatg ccccgctggt cagcttcgat     540
gagacgttca aactagtgaa ggtcaacccg ctggcggcgt ggaccgacca agatgtgcag     600
gaatacattg ccgacaacga cgtgctggtt aatccgcttg tgcgggaagg ctatccgtcg     660
atcggttgcg ctccgtgcac agccaaaccc gccgaaggcg ccgacccgcg cagcggacgc     720
tggcaggggc tggccaagac cgaatgcggg ttgcacgcct cgtga                    765

<210> SEQ ID NO 48
<211> LENGTH: 254
<212> TYPE: PRT
<213> ORGANISM: Mycobacterium tuberculosis

<400> SEQUENCE: 48

Met Ser Gly Glu Thr Thr Arg Leu Thr Glu Pro Gln Leu Arg Glu Leu
1               5                   10                  15
```

```
Ala Ala Arg Gly Ala Ala Glu Leu Asp Gly Ala Thr Ala Thr Asp Met
            20                  25                  30

Leu Arg Trp Thr Asp Glu Thr Phe Gly Asp Ile Gly Gly Ala Gly Gly
        35                  40                  45

Gly Val Ser Gly His Arg Gly Trp Thr Thr Cys Asn Tyr Val Val Ala
    50                  55                  60

Ser Asn Met Ala Asp Ala Val Leu Val Asp Leu Ala Ala Lys Val Arg
65              70                  75                      80

Pro Gly Val Pro Val Ile Phe Leu Asp Thr Gly Tyr His Phe Val Glu
                85                  90                  95

Thr Ile Gly Thr Arg Asp Ala Ile Glu Ser Val Tyr Asp Val Arg Val
            100                 105                 110

Leu Asn Val Thr Pro Glu His Thr Val Ala Glu Gln Asp Glu Leu Leu
            115                 120                 125

Gly Lys Asp Leu Phe Ala Arg Asn Pro His Glu Cys Cys Arg Leu Arg
    130                 135                 140

Lys Val Val Pro Leu Gly Lys Thr Leu Arg Gly Tyr Ser Ala Trp Val
145                 150                 155                 160

Thr Gly Leu Arg Arg Val Asp Ala Pro Thr Arg Ala Asn Ala Pro Leu
                165                 170                 175

Val Ser Phe Asp Glu Thr Phe Lys Leu Val Lys Val Asn Pro Leu Ala
                180                 185                 190

Ala Trp Thr Asp Gln Asp Val Gln Glu Tyr Ile Ala Asp Asn Asp Val
            195                 200                 205

Leu Val Asn Pro Leu Val Arg Glu Gly Tyr Pro Ser Ile Gly Cys Ala
    210                 215                 220

Pro Cys Thr Ala Lys Pro Ala Glu Gly Ala Asp Pro Arg Ser Gly Arg
225                 230                 235                 240

Trp Gln Gly Leu Ala Lys Thr Glu Cys Gly Leu His Ala Ser
                245                 250
```

TUBERCULOSIS ANTIGEN DETECTION ASSAYS AND VACCINES

RELATED APPLICATION

This application claims the benefit of U.S. Provisional Application No. 60/696,439, filed Jul. 1, 2005, entitled "Tuberculosis Antigen Detection Assays and Vaccines", and claims the benefit of U.S. Provisional Application No. 60/717,062, filed Sep. 14, 2005, entitled "Tuberculosis Antigen Detection Assays and Vaccines". The entire teachings of the above applications are incorporated herein by reference.

GOVERNMENT SUPPORT

The invention was supported, in whole or in part, by a grant, No. TDA30469A from The World Health Organization, and No. NIH AI43529 from the National Institutes of Health. The Government has certain rights in the invention.

BACKGROUND OF THE INVENTION

More than one-third of the world population is infected with *Mycobacterium tuberculosis*, the bacterium that causes the Tuberculosis (TB) disease. Each year, 8 million people become infected with TB, and 2 million people die from the disease. TB significantly affects developing countries and is also becoming an increasing problem in developed areas of the world.

Persons infected with TB can be asymptomatic for a considerable period of time, and can be in a latent stage of the disease. In its active state, the disease is often manifested with an acute inflammation of the lungs, resulting in fever and a nonproductive cough. If untreated, serious complications and death typically result. Present diagnostic assays are often inaccurate, and are unable to distinguish between persons in the latent stage of the disease and those in the active stage.

Currently, vaccination with live bacteria is one method for immunizing persons against the disease. However, TB vaccination with certain live bacteria has often been the source of controversy in some countries, including the United States, and consequently has not been put into widespread use in the U.S. Additionally, current diagnostic tests are many times unable to distinguish between persons who have been immunized, and persons infected with TB.

Effective vaccination and accurate early diagnosis of the disease are important to control the disease. Consequently, a need exists for effective diagnostic assays that detect active infection by the TB bacteria. A further need exits for a vaccine that does not use a live bacteria and provides a protective immunogenic response to the disease.

SUMMARY OF THE INVENTION

The present invention relates to isolated polypeptide molecules that have an immunogenic portion of a *Mycobacterium tuberculosis* antigen, or a variant of the antigen that differs only in conservative substitutions and/or modifications. The antigen has an amino acid sequence of SEQ ID NO: 2, 4, 6, 8, 10, 12, 14, 16, 18, 20, 22, 24, 26, 28, 30, 32, 34, 36, 38, 40, 42, 44, 46, 48, or combination thereof; or an amino acid sequence encoded by a nucleic acid molecule having a sequence of SEQ ID NO: 1, 3, 5, 7, 9, 11, 13, 15, 17, 19, 21, 23, 25, 27, 29, 31, 33, 35, 37, 39, 41, 43, 45, 47, or combination thereof; the coding region of SEQ ID NO:1, 3, 5, 7, 9, 11, 13, 15, 17, 19, 21, 23, 25, 27, 29, 31, 33, 35, 37, 39, 41, 43, 45, 47, or combination thereof; a complement of SEQ ID NO:1, 3, 5, 7, 9, 11, 13, 15, 17, 19, 21, 23, 25, 27, 29, 31, 33, 35, 37, 39, 41, 43, 45, 47, or combination thereof; or a sequence that hybridizes (e.g., under high stringency conditions) to SEQ ID NO:1, 3, 5, 7, 9, 11, 13, 15, 17, 19, 21, 23, 25, 27, 29, 31, 33, 35, 37, 39, 41, 43, 45, 47, or combination thereof In one embodiment, the isolated polypeptide molecule stimulates an immunogenic specific Tuberculosis (TB) response in a host or an animal (e.g., human, mouse, pig, goat, monkey). In another embodiment, the present invention includes an isolated polypeptide molecule of an immunogenic portion of a *M. tuberculosis* antigen, wherein the antigen comprises an amino acid sequence encoded by a nucleic acid molecule having greater than or equal to about 70% identity (e.g., about 80% identity, 90% identity, about 95% identity) with any one of the sequences recited above. The present invention, in one embodiment, includes an isolated polypeptide molecule, wherein an amino acid sequence has greater than or equal to about 70% similarity (e.g., about 80% similarity, about 90% similarity, about 95% similarity) to the sequences recited herein.

The present invention further embodies isolated nucleic acid molecules that encode polypeptide molecules that have an immunogenic portion of a *M. tuberculosis* antigen, or a variant of the antigen that differs only in conservative substitutions and/or modifications. The antigen is encoded by a nucleic acid molecule having a sequence of SEQ ID NO: 1, 3, 5, 7, 9, 11, 13, 15, 17, 19, 21, 23, 25, 27, 29, 31, 33, 35, 37, 39, 41, 43, 45, 47, or combination thereof; the coding region of SEQ ID NO: 1, 3, 5, 7, 9, 11, 13, 15, 17, 19, 21, 23, 25, 27, 29, 31, 33, 35, 37, 39, 41, 43, 45, 47, or combination thereof; a complement of SEQ ID NO:1, 3, 5, 7, 9, 11, 13, 15, 17, 19, 21, 23, 25, 27, 29, 31, 33, 35, 37, 39, 41, 43, 45, 47, or combination thereof; that hybridizes (e.g., under high stringency conditions) to SEQ ID NO: 1, 3, 5, 7, 9, 11, 13, 15, 17, 19, 21, 23, 25, 27, 29, 31, 33, 35, 37, 39, 41, 43, 45, 47, or combination thereof; or that encodes SEQ ID NO: 2, 4, 6, 8, 10, 12, 14, 16, 18, 20, 22, 24, 26, 28, 30, 32, 34, 36, 38, 40, 42, 44, 46, 48, or combination thereof. The isolated nucleic acid molecule encodes a polypeptide molecule that stimulates an immunogenic specific TB response. The present invention also includes isolated nucleic acid molecules that encode a polypeptide molecule that has an immunogenic portion of a *M. tuberculosis* antigen, wherein the antigen is encoded by a nucleic acid molecule having greater than or equal to about 70% identity (e.g., about 80% identity, 90% identity, about 95% identity) of the recited sequences. The present invention, in one embodiment, includes isolated nucleic acid molecules that encode polypeptide molecules whose sequence has greater than or equal to about 70% similarity (e.g., about 80% similarity, about 90% similarity, about 95% similarity) to the sequences recited herein.

Yet another embodiment of the invention includes vectors, plasmids and host cells that contain the nucleic acid molecules or encode the polypeptide molecules described herein. The host cell can be any cell including, e.g., *E. coli*, yeast and mammalian cells. The present invention additionally includes probes that hybridize under stringency conditions (e.g., high or moderate) to a nucleic acid molecules described herein.

The present invention includes antibodies that bind to one or more of the polypeptide molecules described herein. The antibody can be a monoclonal antibody or a polyclonal antibody. The invention also pertains to fusion proteins that comprise one or more the polypeptide molecules described herein (e.g., two polypeptide molecules). In addition to including the polypeptide molecules of the present invention, the fusion protein can also include other *M. tuberculosis* antigens, including those presented on a MHC Class-2 molecule (e.g., a CD4+ T-cell pathway TB antigen).

The present invention includes methods for stimulating a specific immunogenic TB response in an individual, preventing or reducing the severity of the TB disease, by administering an amount of one or more of the polypeptide molecules or nucleic acid molecules described herein (e.g., in a carrier). In another aspect, the present invention includes compositions (e.g., vaccine compositions or pharmaceutical compositions) having the polypeptide molecules or nucleic acid molecules described herein, in a physiologically acceptable carrier. The composition can also include or can be co-administered with an immune response enhancer (e.g., an adjuvant, another TB antigen, immunostimulatory cytokine or chemokine). Examples of adjuvants include 3D-MPL and QS21. The composition can be formulated in an oil in water emulsion.

The present invention further embodies methods for monitoring treatment of the TB disease in an individual. The methods include detecting the level of one or more M. tuberculosis antigenic polypeptides described herein in a sample from the individual; and comparing the level with a standard. A level of TB antigenic peptides that is higher than the standard indicates ineffective treatment, and a level that is less than or equal to the standard indicates effective treatment. The method of monitoring treatment can also include detecting levels of one or more of the TB antigenic peptides described herein in a sample at one or more time points (e.g., a first or baseline time point, and second time point after commencement of treatment), and comparing the levels at the time points. Increases in the levels of the peptides indicates ineffective treatment, and decrease or no change in the levels indicates effective treatment.

The invention includes methods of diagnosing TB disease in an individual by detecting the presence, absence, or levels of one or more of the polypeptide molecules described herein. The diagnostic assays of the present invention also allow one to distinguish between an individual having the active TB disease and immunity to TB. Such a method includes detecting the presence, absence or level of one or more of the polypeptide molecules described herein, and measuring the stimulation of a TB specific immune response in the individual. The absence of the polypeptide molecules in a sample from the individual, and the presence of a TB specific immune response in the individual indicates that the individual has acquired some immunity to the TB disease and not the disease itself. Measuring the stimulation of a TB specific immune response includes measuring cell proliferation, interleukin-12 production, interferon-γ levels, or a combination thereof, in a sample from the individual.

The present invention includes, in an additional embodiment, methods for detecting M. tuberculosis infection in a biological sample, by assessing the presence of one or more of the polypeptide molecules described herein in the sample. The presence of one or more of the molecules indicate the presence of M. tuberculosis infection; and the absence of one or more of the molecules indicate the absence of M. tuberculosis infection. In particular, methods include contacting the sample with an antibody (e.g., a detectably labeled antibody) that binds with the polypeptide molecule, sufficiently to allow formation of a complex between the sample and the antibody, to thereby form an antigen-antibody complex; and detecting the antigen-antibody complex. The presence of the complex indicates the presence of M. tuberculosis infection, and the absence of a complex indicates the absence of M. tuberculosis infection. In one aspect, the method further includes contacting the sample with a second antibody specific to the antigen or the antigen-antibody complex. The polypeptide or the antibody can be bound to a solid support, and the biological sample can be urine, blood, sputum, cerebrospinal fluid, or tissue sample.

Methods for detecting M. tuberculosis infection in a biological sample also include contacting the sample with at least two oligonucleotide primers in a polymerase chain reaction, wherein at least one of the oligonucleotide primers (e.g., at least about 10 contiguous bases) is specific for one or more of the isolated nucleic acid molecules described herein, sufficiently to allow amplification of the primers; and detecting in the sample the amplified nucleic acid sequence. The presence any one of the amplified nucleic acid sequences indicates M. tuberculosis infection, and the absence of any one of the amplified nucleic acid sequences indicates an absence of M. tuberculosis infection. Another method for detecting M. tuberculosis infection in a biological sample includes contacting the sample with one or more oligonucleotide probes (e.g., at least about 15 contiguous bases) specific for the nucleic acid molecule described herein under high stringency conditions, sufficiently to allow hybridization between the sample and the probe; and detecting the nucleic acid molecule that hybridizes to the oligonucleotide probe in the sample. The presence of hybridization of the probe indicates M. tuberculosis infection, and the absence of hybridization indicates an absence of M. tuberculosis infection.

Furthermore, the present invention includes kits for diagnosing the presence or absence of M. tuberculosis infection in a person. The kit comprises one or more reagents for detecting one or more of polypeptide molecules or nucleic acid molecules described herein. The reagents can include those that are used for carrying out an enzyme-linked immunosorbent assay, a rapid immunochromatographic assay, a flow cytometric analysis, or a radioimmunoassay. Such kits can comprise one or more nucleic acid molecules having a sequence of SEQ ID NO: 1, 3, 5, 7, 9, 11, 13, 15, 17, 19, 21, 23, 25, 27, 29, 31, 33, 35, 37, 39, 41, 43, 45, 47, or combination thereof; the complements of said sequences, and nucleic acid sequences that hybridize to a sequence recited in SEQ ID NO:1, 3, 5, 7, 9, 11, 13, 15, 17, 19, 21, 23, 25, 27, 29, 31, 33, 35, 37, 39, 41, 43, 45, 47, or combination; and a detection reagent. Kits can include other items such as solid supports, and detection agents (e.g., a reporter group like radioisotopes, fluorescent groups, luminescent groups, enzymes, biotin and dye particles; conjugated to a binding agent such as anti-immunoglobulins, Protein G, Protein A and lectins).

Advantages of the present invention include new methods for preventing or reducing the severity of the TB disease by providing an effective vaccine composition. The assays of the present invention allow simple and easy to administer urine tests to quickly and efficiently distinguish between patients having active TB and those who do not. New vaccine compositions and more effective diagnostic assays will assist in reducing the present worldwide TB problem.

BRIEF DESCRIPTION OF THE DRAWINGS

FIGS. 1A-1G are schematics showing the nucleic acid sequences (in Bold) (SEQ ID NO: 1, 3, 5, 7, 9, 11, 13, 15, 17, 19, 21, 23, 25, and 27) and corresponding M. tuberculosis polypeptide sequences (in Bold) (SEQ ID NO: 2, 4, 6, 8, 10, 12, 14, 16, 18, 20, 22, 24, 26, and 28) eluted from MHC class 1 molecules from the macrophages of mice infected with the M. tuberculosis bacteria.

FIG. 1H is a table showing M. tuberculosis peptide sequences, SEQ ID Nos: 2, 6, 10, 14, 18, 22, and 26, eluted from MHC class 1 molecules from the macrophages of mice infected with the M. tuberculosis bacteria. The figure also shows The Institute for Genomic Research (TIGR) annotation, the Swiss-Prot designation, and the protein name.

FIG. 2 is a schematic showing a peptide, SEQ ID NO: 30, in bold, found in the urine of patients with pulmonary tuberculosis, and its corresponding nucleic acid sequence, SEQ ID NO: 29. The figure also shows a DNA sequence (SEQ ID NO: 31) and its corresponding protein sequence (SEQ ID NO: 32) which is a putative molybdopterin biosynthesis protein that is found in M. tuberculosis and has 100% homology to SEQ ID NO: 30.

FIG. 5 is a table showing M. tuberculosis peptide sequences, SEQ ID Nos: 34, 38, 42, and 46, found in the urine of patients with pulmonary tuberculosis and the M tuberculosis donor protein.

FIGS. 6A-B are schematics showing the nucleic acid sequence (in Bold and Underline) (SEQ ID NO: 33) and corresponding M. tuberculosis polypeptide sequence (in Bold and Underline) (SEQ ID NO: 34) found in the urine of patients with pulmonary tuberculosis. Also depicted are Homoserine O-acetyltransferase nucleic acid and polypeptide sequences from M. tuberculosis having 100% homology to the isolated sequences (SEQ ID NOs: 35 and 36, respectively), along with a table providing Genomic Research (TIGR) Locus name, primary locus name, the Swiss-Prot designation, putative identification, Gene Symbol, TIGR cellular roles, coordinates, DNA molecule name, gene length, protein length, molecular weight, pI, percent GC, enzyme Commission #, Kingdom, and Family.

FIGS. 7A-C are schematics showing the nucleic acid sequence (in Bold and Underline) (SEQ ID NO: 37) and corresponding M. tuberculosis polypeptide sequence (in Bold and Underline) (SEQ ID NO: 38) found in the urine of patients with pulmonary tuberculosis. Also depicted are Chromosome partition protein smc nucleic acid and polypeptide sequences from M. tuberculosis having 100% homology to the isolated sequences (SEQ ID NOs: 39 and 40, respectively), along with a table providing the TIGR Locus name, primary locus name, the Swiss-Prot designation, putative identification, Gene Symbol, TIGR cellular roles, coordinates, DNA molecule name, gene length, protein length, molecular weight, pI, percent GC, enzyme Commission #, Kingdom, and Family.

FIGS. 8A-B are schematics showing the nucleic acid sequence (in Bold and Underline) (SEQ ID NO: 41) and corresponding M. tuberculosis polypeptide sequence (in Bold and Underline) (SEQ ID NO: 42) found in the urine of patients with pulmonary tuberculosis. Also depicted are Ornithine carbamoyltransferase nucleic acid and polypeptide sequences from M. tuberculosis having 100% homology to the isolated sequences (SEQ ID NOs: 43 and 44, respectively), along with a table providing the TIGR Locus name, primary locus name, the Swiss-Prot designation, putative identification, Gene Symbol, TIGR cellular roles, coordinates, DNA molecule name, gene length, protein length, molecular weight, pI, percent GC, enzyme Commission #, Kingdom, and Family.

FIGS. 9A-B are schematics showing the nucleic acid sequence (in Bold and Underline) (SEQ ID NO: 45) and corresponding M. tuberculosis polypeptide sequence (in Bold and Underline) (SEQ ID NO: 46) found in the urine of patients with pulmonary tuberculosis. Also depicted are phosphoadenosine phosphosulfate reductase nucleic acid and polypeptide sequences from M. tuberculosis having 100% homology to the isolated sequences (SEQ ID NOs: 47 and 48, respectively), along with a table providing the TIGR Locus name, primary locus name, the Swiss-Prot designation, putative identification, Gene Symbol, TIGR cellular roles, coordinates, DNA molecule name, gene length, protein length, molecular weight, pI, percent GC, enzyme Commission #, Kingdom, and Family.

DETAILED DESCRIPTION OF THE INVENTION

Figure 3:
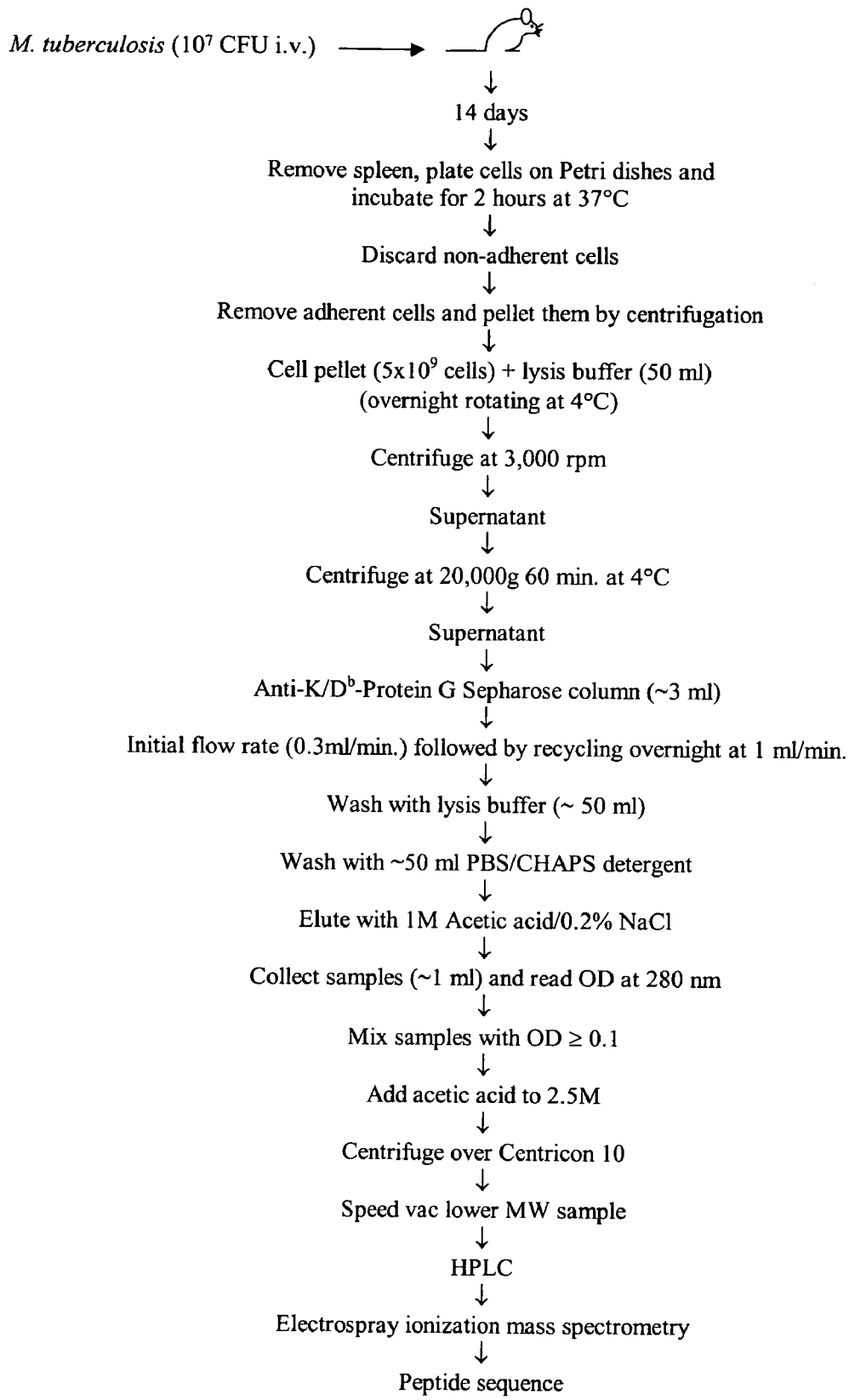
FIG. 3 is a schematic showing the protocol used to purify and sequence MHC Class 1 associated peptides isolated from M. tuberculosis-infected macrophages.

A description of preferred embodiments of the invention follows.

The present invention relates to vaccine compositions and diagnostic assays for the Tuberculosis (TB) disease. The present invention is based, in part, on the discovery of certain TB antigenic peptides presented on the MHC class 1 macrophage, when a host is infected with the bacteria that causes TB, namely the M. tuberculosis bacteria. MHC class-1 macrophages are cells that play a role in the CD8+ T-Cell pathway of the immune response. A second discovery that forms the basis of the present invention is the identification of a TB peptide present in the urine of people infected with active TB. The identity of the specific antigenic TB peptides presented on MHC class 1 cell, and the identity of the TB peptide found in urine of infected patients, provide the polypeptide sequences needed to create effective vaccines and/or diagnostic tests.

TB vaccine compositions of the present invention can include polypeptide sequences or nucleic acid sequences, and, optionally, additional immune enhancing molecules. Hence, the present invention, in part, relates to the specific antigenic TB polypeptide sequences discovered, which are shown in FIGS. 1, 2, and 5-9 namely, SEQ ID NOs 2, 4, 6, 8, 10, 12, 14, 16, 18, 20, 22, 24, 26, 28, 30, 32, 34, 36, 38, 40, 42, 44, 46, 48 and combinations thereof. SEQ ID NOs: 2, 6, 10, 14, 18, 22, and 26 were isolated by infecting mice with significant amounts of M. tuberculosis bacteria. About two weeks after the mice were infected, the spleen was removed, and MHC class 1 molecules, molecules that present antigens to CD8+ T cells, were separated, in accordance with the methods detailed in Example 1. A number of peptides that were found on MHC class 1 molecules were identified as being of *M. tuberculosis* origin. SEQ ID NOs: 1, 3, 5, 7, 9, 11, 13, 15, 17, 19, 21, 23, 25, and 27, the nucleic acid sequences that encode these identified polypeptides, are also shown in FIG. 1A-H.

SEQ ID NO: 30, MVIIELMRR, is a peptide found the in urine of persons with pulmonary TB, and this sequence has 100% homology with a *M. tuberculosis* biosynthesis protein, SEQ ID NO: 32, shown in FIG. 2. The nucleic acid sequence, SEQ ID NO: 31, that encodes this protein is also shown. Additionally, FIGS. 5-9 show SEQ ID NOs: 34, 38, 42, and 46 that were also found in the urine of persons with pulmonary TB, and have 100% homology with SEQ ID NOs: 36, 40, 44, and 48, respectively. The methods used to identify these TB protein in the urine of patients infected with active TB are described in Example 2.

Accordingly, the present invention relates to these sequences, SEQ ID NO: 1-48, that have been identified as being useful in eliciting a protective immune response against TB, and for diagnostic assays for identifying persons with active TB.

Polypeptides and Their Function

The present invention relates to isolated polypeptide molecules that have been isolated including antigenic portions of TB sequences presented by MHC class 1 molecule in an infected host, and TB sequences isolated from urine of infected patients. The present invention includes polypeptide molecules that contain the sequence of any one of the antigenic TB amino acid sequences (SEQ ID NO: 2, 4, 6, 8, 10, 12, 14, 16, 18, 20, 22, 24, 26, 28, 30, 32, 34, 36, 38, 40, 42, 44, 46, 48, or combinations thereof). See FIGS. 1, 2 and 5-9. The present invention also pertains to polypeptide molecules that are encoded by nucleic acid sequences, SEQ ID NO: 1, 3, 5, 7, 9, 11, 13, 15, 17, 19, 21, 23, 25, 27, 29, 31, 33, 35, 37, 39, 41, 43, 45, 47, or combinations thereof).

As used herein, the term "polypeptide" encompasses amino acid chains of any length, including full length proteins (i.e., antigens), wherein the amino acid residues are linked by covalent peptide bonds. Thus, a polypeptide comprising an immunogenic portion of a *M. tuberculosis* antigen can consist entirely of the immunogenic portion, or can contain additional sequences. The additional sequences can be derived from the native *M. tuberculosis* antigen or can be heterologous, and such sequences can (but need not) be immunogenic. In general, the polypeptides disclosed herein are prepared in substantially pure form. Preferably, the polypeptides are at least about 80% pure, more preferably at least about 90% pure and most preferably at least about 99% pure.

Antigenic TB polypeptides of the present invention referred to herein as "isolated" are polypeptides that separated away from other proteins and cellular material of their source of origin. Isolated antigenic TB polypeptides, peptides derived by infection with the *M. tuberculosis* bacteria, include essentially pure protein, proteins produced by chemical synthesis, by combinations of biological and chemical synthesis and by recombinant methods. The proteins of the present invention have been isolated and characterized as to its physical characteristics using the procedures described in the Exemplification, and can be done using laboratory techniques for protein purification. Such techniques include, for example, salting out, immunoprecipitation, column chromatography, high pressure liquid chromatography or electrophoresis.

The compositions and methods of the present invention also encompass variants of the above polypeptides and DNA molecules. A polypeptide "variant," as used herein, is a polypeptide that differs from the recited polypeptide only in conservative substitutions and/or modifications, such that the therapeutic, antigenic and/or immunogenic properties of the polypeptide are retained. A variant of a specific *M tuberculosis* antigen will therefore stimulate cell proliferation and/or IFN-γ in Th1 cells raised against that specific antigen. Polypeptide variants preferably exhibit at least about 70%, more preferably at least about 90% and most preferably at least about 95% homology to the identified polypeptides. For polypeptides with immunoreactive properties, variants can, alternatively, be identified by modifying the amino acid sequence of one of the above polypeptides, and evaluating the immunoreactivity of the modified polypeptide. Such modified sequences can be prepared and tested using, for example, the representative procedures described herein.

As used herein, a "conservative substitution" is one in which an amino acid is substituted for another amino acid that has similar properties, such that one skilled in the art of peptide chemistry would expect the secondary structure and hydropathic nature of the polypeptide to be substantially unchanged. In general, the following groups of amino acids represent conservative changes: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his.

Variants can also, or alternatively, contain other modifications, including the deletion or addition of amino acids that have minimal influence on the antigenic properties, secondary structure and hydropathic nature of the polypeptide. For example, a polypeptide can be conjugated to a signal (or leader) sequence at the N-terminal end of the protein which co-translationally or post-translationally directs transfer of the protein. The polypeptide can also be conjugated to a linker or other sequence for ease of synthesis, purification or identification of the polypeptide (e.g., poly-His), or to enhance binding of the polypeptide to a solid support. For example, a polypeptide can be conjugated to an immunoglobulin Fc region.

The present invention also encompasses TB proteins and polypeptides, variants thereof, or those having amino acid sequences analogous to the amino acid sequences of antigenic TB polypeptides described herein. Such polypeptides are defined herein as antigenic TB analogs (e.g., homologues), or mutants or derivatives. "Analogous" or "homologous" amino acid sequences refer to amino acid sequences with sufficient identity of any one of the TB amino acid sequences so as to possess the biological activity (e.g., the ability to elicit a protective immune response to TB bacteria) of any one of the native TB polypeptides. For example, an analog polypeptide can be produced with "silent" changes in the amino acid sequence wherein one, or more, amino acid residues differ from the amino acid residues of any one of the TB protein, yet still possesses the function or biological activity of the TB. Examples of such differences include additions, deletions or substitutions of residues of the amino acid sequence of TB. Also encompassed by the present invention are analogous polypeptides that exhibit greater, or lesser, biological activity of any one of the TB proteins of the present invention. Such polypeptides can be made by mutating (e.g., substituting, deleting or adding) one or more amino acid or nucleic acid residues to any of the isolated TB molecules described herein. Such mutations can be performed using methods described herein and those known in the art. In particular, the present invention relates to homologous polypeptide molecules having at least about 70% (e.g., 75%, 80%, 85%, 90% or 95%) identity or similarity with SEQ ID NO: 2, 4, 6, 8, 10, 12, 14, 16, 18, 20, 22, 24, 26, 28, 30, 32, 34, 36, 38, 40, 42, 44, 46, 48, or combination thereof. Percent "identity" refers to the amount of identical nucleotides or amino acids between two nucleotides or amino acid sequences, respectfully. As used herein, "percent similarity" refers to the amount of similar or conservative amino acids between two amino acid sequences.

The polypeptides of the present invention, including a full length sequence, partial sequences, functional fragments and homologues, that allow for or assist in stimulating an immunogenic specific or protective immune response to TB. "Immunogenic," as used herein, refers to the ability to elicit an immune response (e.g., cellular) in a patient, such as a human, and/or in a biological sample. In particular, antigens that are immunogenic (and immunogenic portions thereof) stimulate cell proliferation, interleukin-12 production and/or interferon-γ production in biological samples comprising one or more cells (e.g., T cells, NK cells, B cells and macrophage). Such cells are derived from an *M. tuberculosis*-immune individual. Immunogenic portions of the antigens described herein can be prepared and identified using the techniques described herein. Other techniques, such as those summarized in Paul, Fundamental Immunology, 3d ed., Raven Press, 1993, pp. 243-247 and references cited therein, can be used. Such techniques include screening polypeptide portions of the native antigen for immunogenic properties. An immunogenic portion of a polypeptide is a portion that, within such assays, generates an immune response (e.g., proliferation, interferon-γ production and/or interleukin-12 production) that is substantially similar to that generated by the full-length antigen. In other words, an immunogenic portion of an antigen can generate at least about 20%, and preferably about 100%, of the proliferation induced by the full length antigen in the model proliferation assay described herein. An immunogenic portion can also, or alternatively, stimulate the production of at least about 20%, and preferably about 100%, of the interferon-γ and/or interleukin-12 induced by the full length antigen in the model assay described herein. As used herein, "TB" or "TB disease" refers to the disease cause by the infection of *M. tuberculosis*.

Homologous polypeptides can be determined using methods known to those of skill in the art. Initial homology searches can be performed at NCBI against the GenBank, EMBL and SwissProt databases using, for example, the BLAST network service. Altschuler, S. F., et al., J. Mol. Biol., 215:403 (1990), Altschuler, S. F., Nucleic Acids Res., 25:3389-3402 (1998). Computer analysis of nucleotide sequences can be performed using the MOTIFS and the FindPatterns subroutines of the Genetics Computing Group (GCG, version 8.0) software. Protein and/or nucleotide comparisons were performed according to Higgins and Sharp (Higgins, D. G. and Sharp, P. M., Gene, 73:237-244 (1988) e.g., using default parameters).

Additionally, the individual isolated polypeptides of the present invention are biologically active or functional and play various roles in bacteria as well. For example, isolated polypeptide, such as SEQ ID NO: 6 is a glutamine-transport transmembrane protein ABC transporter. Likewise, SEQ ID NO: 22 is a cationic amino acid transport integral member protein, and SEQ ID NO: 26 is a Cationic transporting P-type ATPase. SEQ ID NO: 32, is a molybdopterin biosynthesis protein. The present invention includes fragments of these isolated amino acid sequences, yet possess the function or biological activity of the sequence. For example, polypeptide fragments comprising deletion mutants of the antigenic TB proteins can be designed and expressed by well-known laboratory methods. Fragments, homologues, or analogous polypeptides can be evaluated for biological activity, as described herein.

The present invention also encompasses biologically active derivatives or analogs of the above described antigenic TB polypeptides, referred to herein as peptide mimetics. Mimetics can be designed and produced by techniques known to those of skill in the art. (see e.g., U.S. Pat. Nos. 4,612,132; 5,643,873 and 5,654,276). These mimetics can be based, for example, on a specific TB amino acid sequence and maintain the relative position in space of the corresponding amino acid sequence. These peptide mimetics possess biological activity similar to the biological activity of the corresponding peptide compound, but possess a "biological advantage" over the corresponding antigenic TB amino acid sequence with respect to one, or more, of the following properties: solubility, stability and susceptibility to hydrolysis and proteolysis.

Methods for preparing peptide mimetics include modifying the N-terminal amino group, the C-terminal carboxyl group, and/or changing one or more of the amino linkages in the peptide to a non-amino linkage. Two or more such modifications can be coupled in one peptide mimetic molecule. Modifications of peptides to produce peptide mimetics are described in U.S. Pat. Nos. 5,643,873 and 5,654,276. Other forms of the antigenic TB polypeptides, encompassed by the present invention, include those which are "functionally equivalent." This term, as used herein, refers to any nucleic acid sequence and its encoded amino acid, which mimics the biological activity of the TB polypeptides and/or functional domains thereof.

TB Nucleic Acid Sequences, Plasmids, Vectors and Host Cells

The present invention, in one embodiment, includes an isolated nucleic acid molecule having a sequence of SEQ ID NO: 1, 3, 5, 7, 9, 11, 13, 15, 17, 19, 21, 23, 25, 27, 29, 31, 33, 35, 37, 39, 41, 43, 45, 47, or combinations thereof. See FIGS. 1, 2 and 5-9. The present invention includes sequences as recited in FIGS. 1, 2, and 5-9, as well as the coding regions thereof.

As used herein, the terms "DNA molecule" or "nucleic acid molecule" include both sense and anti-sense strands, cDNA, genomic DNA, recombinant DNA, RNA, and wholly or partially synthesized nucleic acid molecules. A nucleotide "variant" is a sequence that differs from the recited nucleotide sequence in having one or more nucleotide deletions, substitutions or additions. Such modifications can be readily introduced using standard mutagenesis techniques, such as oligonucleotide-directed site-specific mutagenesis as taught, for example, by Adelman et al. (DNA 2:183, 1983). Nucleotide variants can be naturally occurring allelic variants, or non-naturally occurring variants. Variant nucleotide sequences preferably exhibit at least about 70%, more preferably at least about 80% and most preferably at least about 90% homology to the recited sequence. Such variant nucleotide sequences will generally hybridize to the recited nucleotide sequence under stringent conditions. In one embodiment, "stringent conditions" refers to prewashing in a solution of 6×SSC, 0.2% SDS; hybridizing at 65 Celsius, 6×SSC, 0.2% SDS overnight; followed by two washes of 30 minutes each in 1×SSC, 0.1% SDS at 65° C. and two washes of 30 minutes each in 0.2×SSC, 0.1% SDS at 65° C.

The present invention also encompasses isolated nucleic acid sequences that encode TB polypeptides, and in particular, those which encode a polypeptide molecule having an amino acid sequence of SEQ ID NO: 2, 4, 6, 8, 10, 12, 14, 16, 18, 20, 22, 24, 26, 28, 30, 32, 34, 36, 38, 40, 42, 44, 46, 48, or combinations thereof. These TB nucleic acid sequences encode polypeptides that stimulate a protective immunogenic response to the *M. tuberculosis* bacteria and/or are involved the functions further described herein.

As used herein, an "isolated" gene or nucleotide sequence which is not flanked by nucleotide sequences which normally (e.g., in nature) flank the gene or nucleotide sequence (e.g., as in genomic sequences) and/or has been completely or partially purified from other transcribed sequences (e.g., as in a cDNA or RNA library). Thus, an isolated gene or nucleotide sequence can include a gene or nucleotide sequence which is synthesized chemically or by recombinant means. Nucleic acid constructs contained in a vector are included in the definition of "isolated" as used herein. Also, isolated nucleotide sequences include recombinant nucleic acid molecules and heterologous host cells, as well as partially or substantially or purified nucleic acid molecules in solution. In vivo and in vitro RNA transcripts of the present invention are also encompassed by "isolated" nucleotide sequences. Such isolated nucleotide sequences are useful for the manufacture of the encoded antigenic TB polypeptide, as probes for isolating homologues sequences (e.g., from other mammalian species or other organisms), for gene mapping (e.g., by in situ hybridization), or for detecting the presence (e.g., by Southern blot analysis) or expression (e.g., by Northern blot analysis) of related genes in cells or tissue.

The antigenic TB nucleic acid sequences of the present invention include homologues nucleic acid sequences. "Analogous" or "homologous" nucleic acid sequences refer to nucleic acid sequences with sufficient identity of any one of the TB nucleic acid sequences, such that once encoded into polypeptides, they possess the biological activity of any one of the antigenic TB polypeptides described herein. For example, an analogous nucleic acid molecule can be produced with "silent" changes in the sequence wherein one, or more, nucleotides differ from the nucleotides of any one of the TB polypeptides described herein, yet, once encoded into a polypeptide, still possesses its function or biological activity. Examples of such differences include additions, deletions or substitutions. Also encompassed by the present invention are nucleic acid sequences that encode analogous polypeptides that exhibit greater, or lesser, biological activity of the TB proteins of the present invention. In particular, the present invention is directed to nucleic acid molecules having at least about 70% (e.g., 75%, 80%, 85%, 90% or 95%) identity with SEQ ID NO: 1, 3, 5, 7, 9, 11, 13, 15, 17, 19, 21, 23, 25, 27, 29, 31, 33, 35, 37, 39, 41, 43, 45, 47, or combinations thereof.

The nucleic acid molecules of the present invention, including the full length sequences, the partial sequences, functional fragments and homologues, once encoded into polypeptides, elicit an specific immunogenic TB response, or has the function of the polypeptide, as further described herein. The homologous nucleic acid sequences can be determined using methods known to those of skill in the art, and by methods described herein including those described for determining homologous polypeptide sequences. Immunogenic antigens can then be sequenced using techniques such as Edman chemistry. See Edman and Berg, Eur. J. Biochem. 80:116-132, 1967.

Also encompassed by the present invention are nucleic acid sequences, DNA or RNA, which are substantially complementary to the DNA sequences encoding the antigenic TB polypeptides of the present invention, and which specifically hybridize with their DNA sequences under conditions of stringency known to those of skill in the art. As defined herein, substantially complementary means that the nucleic acid need not reflect the exact sequence of the TB sequences, but must be sufficiently similar in sequence to permit hybridization with TB nucleic acid sequence under high stringency conditions. For example, non-complementary bases can be interspersed in a nucleotide sequence, or the sequences can be longer or shorter than the TB nucleic acid sequence, provided that the sequence has a sufficient number of bases complementary to the TB sequence to allow hybridization therewith. Conditions for stringency are described in e.g., Ausubel, F. M., et al., Current Protocols in Molecular Biology, (Current Protocol, 1994), and Brown, et al., Nature, 366:575 (1993); and further defined in conjunction with certain assays.

Also encompassed by the present invention are nucleic acid sequences, genomic DNA, cDNA, RNA or a combination thereof, which are substantially complementary to the DNA sequences of the present invention and which specifically hybridize with the antigenic TB nucleic acid sequences under conditions of sufficient stringency (e.g., high stringency) to identify DNA sequences with substantial nucleic acid identity.

The present invention also includes portions and other variants of *M tuberculosis* antigens that are generated by synthetic or recombinant means. Synthetic polypeptides having fewer than about 100 amino acids, and generally fewer than about 50 amino acids, can be generated using techniques well known to those of ordinary skill in the art. For example, such polypeptides can be synthesized using any of the commercially available solid-phase techniques, such as the Merrifield solid-phase synthesis method, where amino acids are sequentially added to a growing amino acid chain. See Merrifield, J. Am. Chem. Soc. 85:2149-2146, 1963. Equipment for automated synthesis of polypeptides is commercially available from suppliers such as Applied BioSystems, Inc., Foster City, Calif., and can be operated according to the manufacturer's instructions. Variants of a native antigen can generally be prepared using standard mutagenesis techniques, such as oligonucleotide-directed site-specific mutagenesis. Sections of the DNA sequence can also be removed using standard techniques to permit preparation of truncated polypeptides.

In another embodiment, the present invention includes nucleic acid molecules (e.g., probes or primers) that hybridize to the TB sequences, SEQ ID NO:1, 3, 5, 7, 9, 11, 13, 15, 17, 19, 21, 23, 25, 27, 29, 31, 33, 35, 37, 39, 41, 43, 45, 47, or combinations thereof under high or moderate stringency conditions. In one aspect, the present invention includes molecules that are or hybridize to at least about 20 contiguous nucleotides or longer in length (e.g., 50, 100, 200, 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, or 4000). Such molecules hybridize to one of the TB nucleic acid sequences under high stringency conditions. The present invention includes such molecules and those that encode a polypeptide that has the functions or biological activity described herein.

Typically the nucleic acid probe comprises a nucleic acid sequence (e.g. SEQ ID NO: 1, 3, 5, 7, 9, 11, 13, 15, 17, 19, 21, 23, 25, 27, 29, 31, 33, 35, 37, 39, 41, 43, 45, 47, or combinations thereof) and is of sufficient length and complementarity to specifically hybridize to a nucleic acid sequence that encodes a TB antigenic polypeptide. For example, a nucleic acid probe can be at least about 5%, 10%, 20%, 30%, 40%, 50%, 60%, 70%, 80% or 90% the length of the TB nucleic acid sequence. The requirements of sufficient length and complementarity can be easily determined by one of skill in the art. Suitable hybridization conditions (e.g., high stringency conditions) are also described herein. Additionally, the present invention encompasses fragments of the polypeptides of the present invention or nucleic acid sequences that encodes a polypeptide wherein the polypeptide has the biologically activity of the TB polypeptides recited herein.

Such fragments are useful as probes for assays described herein, and as experimental tools, or in the case of nucleic acid fragments, as primers. A preferred embodiment includes primers and probes which selectively hybridize to the nucleic acid constructs encoding any one of the recited TB polypeptides. For example, nucleic acid fragments which encode any one of the domains described herein are also implicated by the present invention.

Stringency conditions for hybridization refers to conditions of temperature and buffer composition which permit hybridization of a first nucleic acid sequence to a second nucleic acid sequence, wherein the conditions determine the degree of identity between those sequences which hybridize to each other. Therefore, "high stringency conditions" are those conditions wherein only nucleic acid sequences which are very similar to each other will hybridize. The sequences can be less similar to each other if they hybridize under moderate stringency conditions. Still less similarity is needed for two sequences to hybridize under low stringency conditions. By varying the hybridization conditions from a stringency level at which no hybridization occurs, to a level at which hybridization is first observed, conditions can be determined at which a given sequence will hybridize to those sequences that are most similar to it. The precise conditions determining the stringency of a particular hybridization include not only the ionic strength, temperature, and the concentration of destabilizing agents such as formamide, but also factors such as the length of the nucleic acid sequences, their base composition, the percent of mismatched base pairs between the two sequences, and the frequency of occurrence of subsets of the sequences (e.g., small stretches of repeats) within other non-identical sequences. Washing is the step in which conditions are set so as to determine a minimum level of similarity between the sequences hybridizing with each other. Generally, from the lowest temperature at which only homologous hybridization occurs, a 1% mismatch between two sequences results in a 1° C. decrease in the melting temperature ($T_m$) for any chosen SSC concentration. Generally, a doubling of the concentration of SSC results in an increase in the $T_m$ of about 17° C. Using these guidelines, the washing temperature can be determined empirically, depending on the level of mismatch sought. Hybridization and wash conditions are explained in Current Protocols in Molecular Biology (Ausubel, F. M. et al., eds., John Wiley & Sons, Inc., 1995, with supplemental updates) on pages 2.10.1 to 2.10.16, and 6.3.1 to 6.3.6.

High stringency conditions can employ hybridization at either (1) 1×SSC (10×SSC=3 M NaCl, 0.3 M Na$_3$-citrate...2H$_2$O (88 g/liter), pH to 7.0 with 1 M HCl), 1% SDS (sodium dodecyl sulfate), 0.1-2 mg/ml denatured calf thymus DNA at 65° C., (2) 1×SSC, 50% formamide, 1% SDS, 0.1-2 mg/ml denatured calf thymus DNA at 42° C., (3) 1% bovine serum albumin (fraction V), 1 mM Na$_2$...EDTA, 0.5 M NaHPO$_4$ (pH 7.2) (1 M NaHPO$_4$=134 g Na$_2$HPO$_4$...7H$_2$O, 4 ml 85% H$_3$PO$_4$ per liter), 7% SDS, 0.1-2 mg/ml denatured calf thymus DNA at 65° C., (4) 50% formamide, 5×SSC, 0.02 M Tris-HCl (pH 7.6), 1×Denhardt's solution (100×=10 g Ficoll 400, 10 g polyvinylpyrrolidone, 10 g bovine serum albumin (fraction V), water to 500 ml), 10% dextran sulfate, 1% SDS, 0.1-2 mg/ml denatured calf thymus DNA at 42° C., (5) 5×SSC, 5×Denhardt's solution, 1% SDS, 100 µg/ml denatured calf thymus DNA at 65° C., or (6) 5×SSC, 5×Denhardt's solution, 50% formamide, 1% SDS, 100 µg/ml denatured calf thymus DNA at 42° C., with high stringency washes of either (1) 0.3-0.1×SSC, 0.1% SDS at 65° C., or (2) 1 mM Na$_2$EDTA, 40 mM NaHPO$_4$ (pH 7.2), 1% SDS at 65° C. The above conditions are intended to be used for DNA-DNA hybrids of 50 base pairs or longer. Where the hybrid is believed to be less than 18 base pairs in length, the hybridization and wash temperatures should be 5-10° C. below that of the calculated $T_m$ of the hybrid, where $T_m$ in ° C.=(2× the number of A and T bases)+(4× the number of G and C bases). For hybrids believed to be about 18 to about 49 base pairs in length, the $T_m$ in ° C.=(81.5° C.+16.6(log$_{10}$M)+0.41(% G+C)−0.61 (% formamide)−500/L), where "M" is the molarity of monovalent cations (e.g., Na$^+$), and "L" is the length of the hybrid in base pairs.

Moderate stringency conditions can employ hybridization at either (1) 4×SSC, (10×SSC=3 M NaCl, 0.3 M Na$_3$-citrate...2H$_2$O (88 g/liter), pH to 7.0 with 1 M HCl), 1% SDS (sodium dodecyl sulfate), 0.1-2 mg/ml denatured calf thymus DNA at 65° C., (2) 4×SSC, 50% formamide, 1% SDS, 0.1-2 mg/ml denatured calf thymus DNA at 42° C., (3) 1% bovine serum albumin (fraction V), 1 mM Na$_2$...EDTA, 0.5 M NaHPO$_4$ (pH 7.2) (1 M NaHPO$_4$=134 g Na$_2$HPO$_4$...7H$_2$O, 4 ml 85% H$_3$PO$_4$ per liter), 7% SDS, 0.1-2 mg/ml denatured calf thymus DNA at 65° C., (4) 50% formamide, 5×SSC, 0.02 M Tris-HCl (pH-7.6), 1×Denhardt's solution (100×=10 g Ficoll 400, 10 g polyvinylpyrrolidone, 10 g bovine serum albumin (fraction V), water to 500 ml), 10% dextran sulfate, 1% SDS, 0.1-2 mg/ml denatured calf thymus DNA at 42° C., (5) 5×SSC, 5×Denhardt's solution, 1% SDS, 100 µg/ml denatured calf thymus DNA at 65° C., or (6) 5×SSC, 5×Denhardt's solution, 50% formamide, 1% SDS, 100 µg/ml denatured calf thymus DNA at 42° C., with moderate stringency washes of 1×SSC, 0.1% SDS at 65° C. The above conditions are intended to be used for DNA-DNA hybrids of 50 base pairs or longer. Where the hybrid is believed to be less than 18 base pairs in length, the hybridization and wash temperatures should be 5-10° C. below that of the calculated $T_m$ of the hybrid, where $T_m$ in ° C.=(2× the number of A and T bases)+(4× the number of G and C bases). For hybrids believed to be about 18 to about 49 base pairs in length, the $T_m$ in ° C.=(81.5° C.+16.6(log$_{10}$M)+0.41(% G+C)−0.61 (% formamide)-500/L), where "M" is the molarity of monovalent cations (e.g., Na$^+$), and "L" is the length of the hybrid in base pairs.

Low stringency conditions can employ hybridization at either (1) 4×SSC, (10×SSC=3 M NaCl, 0.3 M Na$_3$-citrate...2H$_2$O (88 g/liter), pH to 7.0 with 1 M HCl), 1% SDS (sodium dodecyl sulfate), 0.1-2 mg/ml denatured calf thymus DNA at 50° C., (2) 6×SSC, 50% formamide, 1% SDS, 0.1-2 mg/ml denatured calf thymus DNA at 40° C., (3) 1% bovine serum albumin (fraction V), 1 mM Na$_2$...EDTA, 0.5 M NaHPO$_4$ (pH 7.2) (1 M NaHPO$_4$=134 g Na$_2$HPO$_4$...7H$_2$O, 4 ml 85% H$_3$PO$_4$ per liter), 7% SDS, 0.1-2 mg/ml denatured calf thymus DNA at 50° C., (4) 50% formamide, 5×SSC, 0.02 M Tris-HCl (pH 7.6), 1×Denhardt's solution (100×=10 g Ficoll 400, 10 g polyvinylpyrrolidone, 10 g bovine serum albumin (fraction V), water to 500 ml), 10% dextran sulfate, 1% SDS, 0.1-2 mg/ml denatured calf thymus DNA at 40° C., (5) 5×SSC, 5×Denhardt's solution, 1% SDS, 100 µg/ml denatured calf thymus DNA at 50° C., or (6) 5×SSC, 5×Denhardt's solution, 50% formamide, 1% SDS, 100 µg/ml denatured calf thymus DNA at 40° C., with low stringency washes of either 2×SSC, 0.1% SDS at 50° C., or (2) 0.5% bovine serum albumin (fraction V), 1 mM Na$_2$EDTA, 40 mM NaHPO$_4$ (pH 7.2), 5% SDS. The above conditions are intended to be used for DNA-DNA hybrids of 50 base pairs or longer. Where the hybrid is believed to be less than 18 base pairs in length, the hybridization and wash temperatures should be 5-10° C.

below that of the calculated $T_m$ of the hybrid, where $T_m$ in ° C.=(2× the number of A and T bases)+(4× the number of G and C bases). For hybrids believed to be about 18 to about 49 base pairs in length, the $T_m$ in ° C.=(81.5° C.+16.6($\log_{10}$M)+ 0.41(% G+C)−0.61 (% formamide)−500/L), where "M" is the molarity of monovalent cations (e.g., Na.+), and "L" is the length of the hybrid in base pairs.

The TB nucleic acid sequences of the present invention, or a fragment thereof, can also be used to isolate additional homologs. For example, a cDNA or genomic DNA library from the appropriate organism can be screened with labeled TB nucleic acid sequence to identify homologous genes as described in e.g., Ausebel, et al., Eds., Current Protocols In Molecular Biology, John Wiley & Sons, New York (1997).

Immunogenic antigens can be produced recombinantly using a DNA sequence that encodes the antigen, which has been inserted into an expression vector and expressed in an appropriate host cell. DNA sequences encoding *M. tuberculosis* antigens can, for example, be identified by screening an appropriate *M. tuberculosis* genomic or cDNA expression library with sera obtained from patients infected with *M tuberculosis*. Such screens can generally be performed using techniques well known to those of ordinary skill in the art, such as those described in Sambrook et al., Molecular Cloning: A Laboratory Manual, Cold Spring Harbor Laboratories, Cold Spring Harbor, N.Y., 1989. Degenerate oligonucleotide sequences for use in such a screen can be designed and synthesized, and the screen can be performed. Polymerase chain reaction (PCR) can also be employed, using the above oligonucleotides in methods well known in the art, to isolate a nucleic acid probe from a cDNA or genomic library. The library screen can then be performed using the isolated probe. The present method can optionally include a labeled TB antigenic probe.

Alternatively, genomic or cDNA libraries derived from *M. tuberculosis* can be screened directly using peripheral blood mononuclear cells (PBMCs) or T cell lines or clones derived from one or more *M. tuberculosis*-immune individuals. In general, PBMCs and/or T cells for use in such screens can be prepared as described below. Direct library screens can generally be performed by assaying pools of expressed recombinant proteins for the ability to induce proliferation and/or interferon-γ production in T cells derived from an *M. tuberculosis*-immune individual.

The invention also provides vectors, plasmids or viruses containing one or more of the TB nucleic acid molecules (e.g., having the sequence of SEQ ID NO:1, 3, 5, 7, 9, 11, 13, 15, 17, 19, 21, 23, 25, 27, 29, 31, 33, 35, 37, 39, 41, 43, 45, 47, or combinations thereof). Suitable vectors for use in eukaryotic and prokaryotic cells are known in the art and are commercially available or readily prepared by a skilled artisan. Additional vectors can also be found, for example, in Ausubel, F. M., et al., Current Protocols in Molecular Biology, (Current Protocol, 1994) and Sambrook et al., "Molecular Cloning: A Laboratory Manual," 2nd ED. (1989).

Recombinant polypeptides containing portions and/or variants of a native antigen can be readily prepared from a DNA sequence encoding the polypeptide using a variety of techniques well known to those of ordinary skill in the art. For example, supernatants from suitable host/vector systems which secrete recombinant protein into culture media can be first concentrated using a commercially available filter. Following concentration, the concentrate can be applied to a suitable purification matrix such as an affinity matrix or an ion exchange resin. Finally, one or more reverse phase HPLC steps can be employed to further purify a recombinant protein.

Any of a variety of expression vectors known to those of ordinary skill in the art can be employed to express recombinant polypeptides of this invention. Expression can be achieved in any appropriate host cell that has been transformed or transfected with an expression vector containing a DNA molecule that encodes a recombinant polypeptide. Suitable host cells include prokaryotes, yeast and higher eukaryotic cells. Preferably, the host cells employed are *E. coli*, yeast or a mammalian cell line such as COS or CHO. The DNA sequences expressed in this manner can encode naturally occurring antigens, portions of naturally occurring antigens, or other variants thereof.

Uses of plasmids, vectors or viruses containing the cloned TB receptors or receptor fragments include one or more of the following; (1) generation of hybridization probes for detection and measuring level of TB in tissue or isolation of TB homologs; (2) generation of TB mRNA or protein in vitro or in vivo; and (3) generation of transgenic non-human animals or recombinant host cells.

In one embodiment, the present invention encompasses host cells transformed with the plasmids, vectors or viruses described above. Nucleic acid molecules can be inserted into a construct which can, optionally, replicate and/or integrate into a recombinant host cell, by known methods. The host cell can be a eukaryote or prokaryote and includes, for example, yeast (such as *Pichia pastorius* or *Saccharomyces cerevisiae*), bacteria (such as *E. coli, M. tuberculosis*, or *Bacillus subtilis*), animal cells or tissue, insect Sf9 cells (such as baculoviruses infected SF9 cells) or mammalian cells (somatic or embryonic cells, Human Embryonic Kidney (HEK) cells, Chinese hamster ovary cells, HeLa cells, human 293 cells and monkey COS-7 cells). Host cells suitable in the present invention also include a mammalian cell, a bacterial cell, a yeast cell, an insect cell, and a plant cell.

The nucleic acid molecule can be incorporated or inserted into the host cell by known methods. Examples of suitable methods of transfecting or transforming cells include calcium phosphate precipitation, electroporation, microinjection, infection, lipofection and direct uptake. "Transformation" or "transfection" as used herein refers to the acquisition of new or altered genetic features by incorporation of additional nucleic acids, e.g., DNA. "Expression" of the genetic information of a host cell is a term of art which refers to the directed transcription of DNA to generate RNA which is translated into a polypeptide. Methods for preparing such recombinant host cells and incorporating nucleic acids are described in more detail in Sambrook et al., "Molecular Cloning: A Laboratory Manual," Second Edition (1989) and Ausubel, et al. "Current Protocols in Molecular Biology," (1992), for example.

The host cell is then maintained under suitable conditions for expression and recovery of the antigenic TB polypeptide of the present invention. Generally, the cells are maintained in a suitable buffer and/or growth medium or nutrient source for growth of the cells and expression of the gene product(s). The growth media are not critical to the invention, are generally known in the art and include sources of carbon, nitrogen and sulfur. Examples include Luria broth, Superbroth, Dulbecco's Modified Eagles Media (DMEM), RPMI-1640, M199 and Grace's insect media. The growth media can contain a buffer, the selection of which is not critical to the invention. The pH of the buffered media can be selected and is generally one tolerated by or optimal for growth for the host cell.

The host cell is maintained under a suitable temperature and atmosphere. Alternatively, the host cell is aerobic and the host cell is maintained under atmospheric conditions or other suitable conditions for growth. The temperature should also be selected so that the host cell tolerates the process and can be for example, between about 13-40 degree Celsius.

Antibodies and Methods of Assessment

Method for assessing the presence or absence of the antigenic TB polypeptides described herein, in a sample, are encompassed by the present invention. Suitable assays include immunological methods, such as radioimmunoassay, enzyme-linked immunosorbent assays (ELISA), chemiluminescence assays, and rapid immunochromatographic assays. Any method known now or developed later can be used for measuring antigenic TB polypeptides.

Antibodies reactive with any one of the antigenic TB polypeptides, namely, SEQ ID Nos: 2, 4, 6, 8, 10, 12, 14, 16, 18, 20, 22, 24, 26, 28, 30, 32, 34, 36, 38, 40, 42, 44, 46, 48, or combination thereof, or portions thereof can be used. In a preferred embodiment, the antibodies specifically bind with antigenic TB polypeptides or a portion thereof. The antibodies can be polyclonal or monoclonal, and the term antibody is intended to encompass polyclonal and monoclonal antibodies, and functional fragments thereof. The terms polyclonal and monoclonal refer to the degree of homogeneity of an antibody preparation, and are not intended to be limited to particular methods of production.

In several of the preferred embodiments, immunological techniques detect the presence, absence of levels of antigenic TB polypeptides described herein by means of an anti-TB antibody (i.e., one or more antibodies). The term "anti-TB antibody" includes monoclonal and/or polyclonal antibodies, and mixtures or cocktails thereof, and refers to antibodies specific to polypeptides having a sequence set forth in SEQ ID Nos: 2, 4, 6, 8, 10, 12, 14, 16, 18, 20, 22, 24, 26, 28, 30, 32, 34, 36, 38, 40, 42, 44, 46, 48, or combination thereof, or portions thereof.

Anti-TB antibodies can be raised against appropriate immunogens, such as isolated and/or recombinant antigenic TB polypeptides described herein, analogs or portion thereof (including synthetic molecules, such as synthetic peptides). In one embodiment, antibodies are raised against an isolated and/or recombinant antigenic TB polypeptides described herein or portion thereof (e.g., a peptide) or against a host cell which expresses recombinant antigenic TB polypeptides. In addition, cells expressing recombinant antigenic TB polypeptides described herein, such as transfected cells, can be used as immunogens or in a screen for antibody which binds receptor.

Any suitable technique can prepare the immunizing antigen and produce polyclonal or monoclonal antibodies. The art contains a variety of these methods (see e.g., Kohler et al., Nature, 256: 495-497 (1975) and Eur. J. Immunol. 6: 511-519 (1976); Milstein et al., Nature 266: 550-552 (1977); Koprowski et al., U.S. Pat. No. 4,172,124; Harlow, E. and D. Lane, 1988, Antibodies: A Laboratory Manual, (Cold Spring Harbor Laboratory: Cold Spring Harbor, N.Y.); Current Protocols In Molecular Biology, Vol. 2 (Supplement 27, Summer '94), Ausubel, F. M. et al., Eds., (John Wiley & Sons: New York, N.Y.), Chapter 11, (1991)). Generally, fusing a suitable immortal or myeloma cell line, such as SP2/0, with antibody producing cells can produce a hybridoma. Animals immunized with the antigen of interest provide the antibody producing cell, preferably cells from the spleen or lymph nodes. Selective culture conditions isolate antibody producing hybridoma cells while limiting dilution techniques produce them. Researchers can use suitable assays such as ELISA to select antibody producing cells with the desired specificity.

Other suitable methods can produce or isolate antibodies of the requisite specificity. Examples of other methods include selecting recombinant antibody from a library or relying upon immunization of transgenic animals such as mice.

The present invention includes assays to determine if a person is infected with active TB, as compared with person who does not have active TB (e.g., has latent TB, no TB infection, or has been immunized against TB infection). Latent TB occurs when a person has been infected with *M. tuberculosis*, but the bacteria is dormant or inactive. Active TB infection refers to a person infected with *M. tuberculosis* and the bacteria is acutely affecting portions of the bodying, including the lungs, and other tissues. The present invention, based on the discovery that certain TB antigens are found in the urine of patients with active TB, includes assays for determining the absence or presence of active TB infection.

According to the method, an assay can determine the presence, absence or level of antigenic TB polypeptides in a biological sample. Such an assay includes combining the sample to be tested with an antibody having specificity for antigenic TB polypeptides described herein, under conditions suitable for formation of a complex between antibody and antigenic TB polypeptides, and detecting or measuring (directly or indirectly) the formation of a complex. The sample can be obtained directly or indirectly (e.g., provided by a healthcare provider), and can be prepared by a method suitable for the particular sample (e.g., urine, sputum, cerebral spinal fluid, whole blood, platelet rich plasma, platelet poor plasma, serum) and assay format selected. Methods of combining sample and antibody, and methods of detecting complex formation are also selected to be compatible with the assay format.

Suitable labels can be detected directly, such as radioactive, fluorescent or chemiluminescent labels. They can also be indirectly detected using labels such as enzyme labels and other antigenic or specific binding partners like biotin. Examples of such labels include fluorescent labels such as fluorescein, rhodamine, chemiluminescent labels such as luciferase, radioisotope labels such as $^{32}P$, $^{125}I$, $^{131}I$, enzyme labels such as horseradish peroxidase, and alkaline phosphatase, galactosidase, biotin, avidin, spin labels and the like. The detection of antibodies in a complex can also be done immunologically with a second antibody, which is then detected (e.g., by means of a label). Conventional methods or other suitable methods can directly or indirectly label an antibody. Labeled primary and secondary antibodies can be obtained commercially or prepared using methods know to one of skill in the art (see Harlow, E. and D. Lane, 1988, Antibodies: A Laboratory Manual, (Cold Spring Harbor Laboratory: Cold Spring Harbor, N.Y.).

In a preferred embodiment, the presence, absence, or level of antigenic TB polypeptides in a sample is determined using an ELISA assay, a sandwich ELISA assay, or immunochromatographic assay. For detection of antigenic TB polypeptides in a suitable sample, a sample (e.g., urine) is collected. Samples can be processed as known in the art. The assay further includes combining a suitable sample with a composition having an anti-TB polypeptide antibody as detector (e.g., biotinylated anti-TB polypeptides MAb and HRP-streptavidin, or HRP-conjugated anti-TB polypeptides Mab), and a solid support, such as a microtiter plate or dipstick, having an anti-TB polypeptide capture antibody bound (directly or indirectly) thereto. The detector antibody binds to a different antigenic TB polypeptide epitope from that recognized by the capture antibody, under conditions suitable for the formation of the complex. The assay then involves determining the formation of complex in the samples. The presence of one or more of the antigenic TB polypeptide in a sample of an individual indicates the presence of active TB infection, whereas the absence of a TB polypeptide indicates that the patient does not have active TB infection.

The solid support, such as a microtiter plate, dipstick, bead, pad, strip, or other suitable support, can be coated directly or indirectly with an anti-TB polypeptide antibody or TB specific antigen. For example, an anti-TB polypeptide antibody can coat a microtiter well, or a biotinylated anti-TB polypeptide Mab can be added to a streptavidin coated support. With respect to a immunochromatographic assay, a pad or strip can be coated with an antibody specific for the antigen, and when a sample having the one or more of antigens described herein comes into contact with the antibody, the complex can turn a color with aid of a detector, as further described herein. See FIG. 4. A variety of immobilizing or coating methods as well as a number of solid supports can be used, and can be selected according to the desired format.

Figure 4:
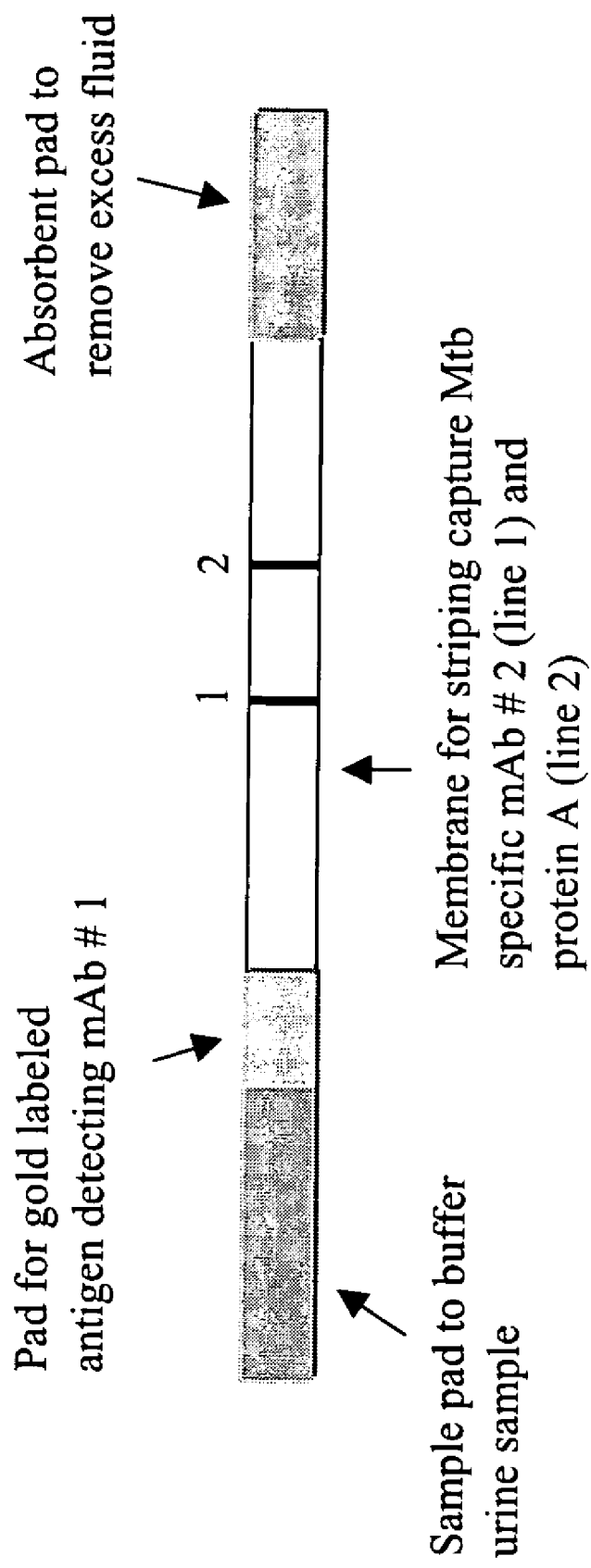
FIG. 4 is a drawing showing an example of a immunochromatographic assay for the detection of TB antigens of the present invention in a sample.
Figure 10:
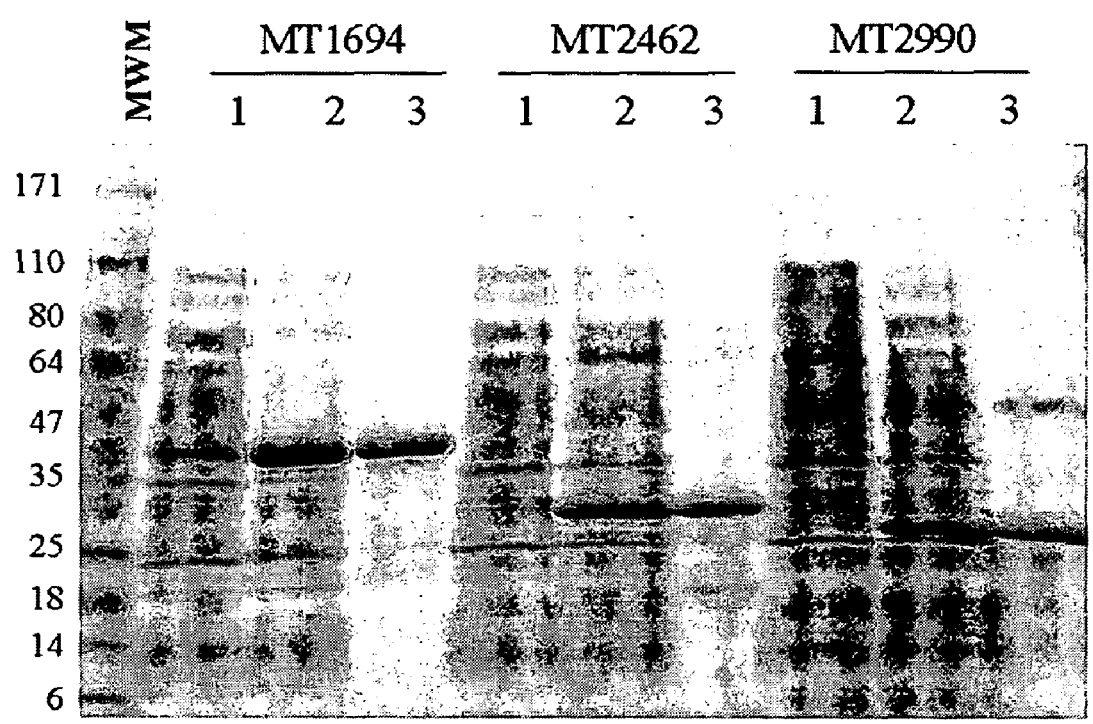
FIG. 10 is a representation of Western Blot showing overexpression and purification of recombinants MT1694, MT2462 and MT2990 from E. coli lysates from non-induced cultures (lanes 1); E. coli lysates from isopropyl-beta-D-thiogalactopyranoside (IPTG) induced cultures (lanes 2); and purified recombinant proteins (lanes 3), and the molecular weight markers (MWM).
Figure 11:
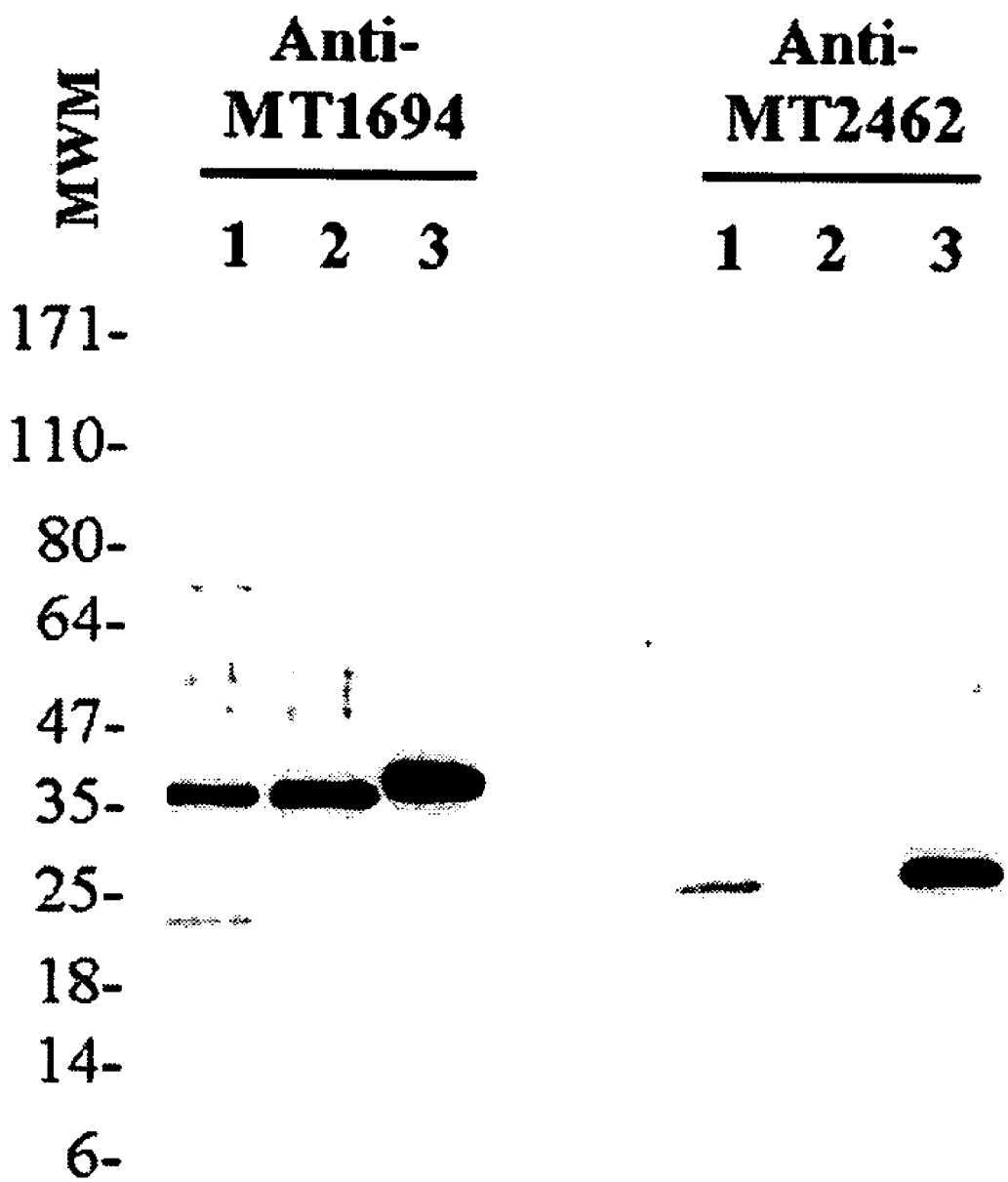
FIG. 11 is a representation of Western Blot showing identification of native MTB1694 and MT2462 in crude whole M. tuberculosis cell lysate (Lane 1); culture filtrate (CF) proteins (Lane 2); purified recombinant antigen (Lane 3); and molecular weight markers (MWM), wherein antigens were electrophoresed and transferred to nitrocellulose membrane followed by probing with either rabbit anti-MTB1694 or anti-MT2462 antisera.
Figure 12A:
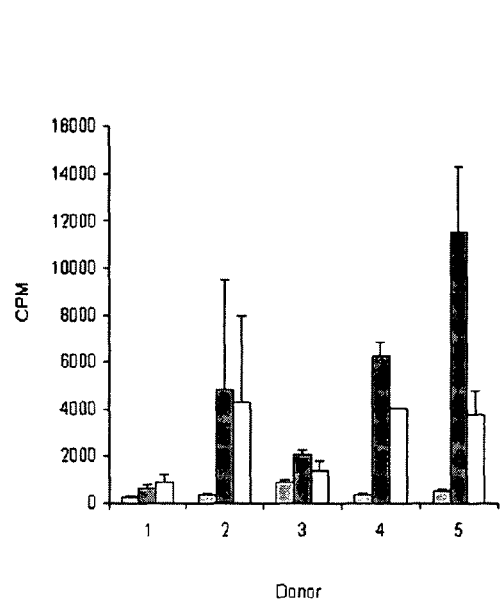
FIG. 12A is a bar graph showing the recognition of MT1694 and MT2452 by proliferative responses expressed as counts per minute (CPM) from healthy PPD (an intradermal skin test response to tuberculosis proteins using a Purified Protein Derivative) negative (donor 1) and PPD positive (donors 2-5) individuals following stimulation with recombinant antigens (5 ug/ml).
Figure 12B:
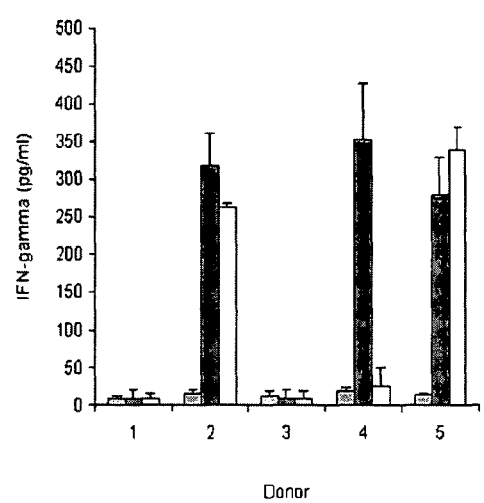
FIG. 12B is a bar graph showing the recognition of MT1694 and MT2452 by IFN-γ production of peripheral blood mononuclear cells (PBMC) from healthy PPD negative (donor 1) and PPD positive (donors 2-5) individuals following stimulation with recombinant antigens (5 ug/ml).

In one immunochromatographic assay, a sample having the TB antigens of the present invention can be added to the pad like that shown in FIG. 4. The sample diffuses across a gold labeled antibody (mAb# 1) that is specific to a portion of the antigen, and a complex between the antigen in the sample and the antibody is formed. As the complex further diffuses across the pad having a second antibody (mAb #2), the antibody binds to a different portion of the antigen. When it hits the line labeled "line 1", the labeled complex turns a color, and the control line ("line 2") will also change color. If the sample does not contain the TB antigens of the present invention, then line 1 will not turn color because the gold-labeled antibody will not bind to the sample and therefore will not come into contact with line 1.

In another embodiment, the sample (or an antigenic TB polypeptide standard) is combined with the solid support simultaneously with the detector antibody, and optionally with a one or more reagents by which detection is monitored. For example, the sample can be combined with the solid support simultaneously with (a) HRP-conjugated anti-TB polypeptide Mab, or (b) a biotinylated anti-TB polypeptide Mab and HRP-streptavidin.

A known amount of an antigenic TB polypeptide standard can be prepared and processed as described above for a suitable sample. This antigenic TB polypeptide standard assists in quantifying the amount of antigenic TB polypeptides detected by comparing the level of antigenic TB polypeptides in the sample relative to that in the standard.

A physician, technician, apparatus or a qualified person can compare the amount of detected complex with a suitable control to determine if the levels are elevated. For example, the level of antigenic TB polypeptides following treatment can be compared with a baseline level prior to treatment, or with levels in normal individuals or suitable controls. A decrease in or maintenance of the levels of one or more TB polypeptides in the urine, as compared to baseline levels, indicates that the treatment is working, whereas increases in levels indicates that is not effective.

Typical assays for antigenic TB polypeptides are sequential assays in which a plate is coated with first antibody, sample is added, the plate is washed, second tagged antibody is added, and the plate is washed and bound second antibody is quantified. In another embodiment, a format in which antibodies and the sample are added simultaneously, in a competitive ELISA format, can achieve greater sensitivity.

A variety of methods can determine the amount of antigenic TB polypeptides in complexes. For example, when HRP is used as a label, a suitable substrate such as OPD can be added to produce color intensity directly proportional to the bound anti-TB polypeptides Mab (assessed e.g., by optical density), and therefore to the antigenic TB polypeptides in the sample.

A technician, physician, qualified person or apparatus can compare the results to a suitable control such as a standard, or baseline levels of antigenic TB polypeptides in a sample from the same donor. For example, the assay can be performed using a known amount of antigenic TB polypeptides standard in lieu of a sample, and a standard curved established. One can relatively compare known amounts of the antigenic TB polypeptides standard to the amount of complex formed or detected.

The nucleic acid that encodes the antigenic TB polypeptides can also be assayed by hybridization, e.g., by hybridizing one of the TB sequences provided herein (e.g., SEQ ID NO: 1, 3, 5, 7, 9, 11, 13, 15, 17, 19, 21, 23, 25, 27, 29, 31, 33, 35, 37, 39, 41, 43, 45, 47, or combinations thereof) or an oligonucleotide derived from one of the sequences, to a DNA or RNA-containing tissue sample from a person. Such a hybridization sequence can have a detectable label, e.g., radioactive, fluorescent, etc., attached to allow the detection of hybridization product. Such methods include contacting the sample with one or more oligonucleotide probes (e.g., at least about 15 contiguous bases) specific for the nucleic acid molecule described herein under high stringency conditions, sufficiently to allow hybridization between the sample and the probe; and detecting the nucleic acid molecule that hybridizes to the oligonucleotide probe in the sample. The presence of hybridization of the probe indicates *M tuberculosis* infection, and the absence of hybridization indicates an absence of *M tuberculosis* infection. Methods for hybridization are well known, and such methods are provided in U.S. Pat. No. 5,837,490, by Jacobs et al., the entire teachings of which are herein incorporated by reference in their entirety. The design of the oligonucleotide probe should preferably follow these parameters: (a) it should be designed to an area of the sequence which has the fewest ambiguous bases ("N's"), if any, and (b) it should be designed to have a $T_m$ of approx. 80° Celsius (assuming 2° Celsius for each A or T and 4° C. for each G or C).

The present invention encompasses detection of TB polypeptides of the present invention in a sample using with PCR methods using primers disclosed or derived from sequences described herein. For example, the sequences described herein can be detected by PCR using SEQ ID Nos: 1, 3, 5, 7, 9, 11, 13, 15, 17, 19, 21, 23, 25, 27, 29, 31, 33, 35, 37, 39, 41, 43, 45, 47, or combinations thereof. PCR is the selective amplification of a target sequence by repeated rounds of nucleic acid replication utilizing sequence-specific primers and a thermostable polymerase. PCR allows recovery of entire sequences between two ends of known sequence. Specifically, contacting the sample with at least two oligonucleotide primers in a PCR, wherein at least one of the oligonucleotide primers (e.g., at least about 10 contiguous bases) is specific for one or more of the isolated nucleic acid molecules described herein. The two are contacted sufficiently to allow amplification of the primers. The amplified nucleic acid sequence in the sample is detected. The presence any one of the amplified nucleic acid sequences indicate *M. tuberculosis* infection, and the absence of any one of the amplified nucleic acid sequences indicate an absence of *M. tuberculosis* infection. Methods of PCR are described herein and are known in the art.

Hence, the present invention includes kits for the detection of SEQ ID Nos:2, 4, 6, 8, 10, 12, 14, 16, 18, 20, 22, 24, 26, 28, 30, 32, 34, 36, 38, 40, 42, 44, 46, 48, or combinations thereof, or the quantification of these sequences, having either antibodies specific for them or a portion thereof, or a nucleic acid sequence that can hybridize to the nucleic acid of encoding these sequences.

Additional immunological or nucleic acid assessments can be performed using methods known in the art. Assays, known in the art or those later developed can be used to assess the antigenic TB polypeptides in a sample.

In addition to measuring the presence of antigenic TB polypeptides in a sample, assays exist to determine the efficacy of a TB vaccine (e.g., the extent to which the immune response is stimulated). These types of assays can be used together to fully assess a person's TB status. For examples, an individual who has a TB-specific immunogenic response, but tests negative to the presence of one or more the antigenic TB polypeptides in a sample, is one who has a level of immunity to the disease. However, a person who has a TB-specific immunogenic response and tests positive to the presence of the antigenic TB polypeptides of the present invention is someone who likely has TB.

The efficacy of a TB vaccine can be measured by determining the immunogenic response of the person who received the vaccine. The TB antigens of the present invention (and immunogenic portions thereof) described herein have the ability to induce an immunogenic response. More specifically, the antigens have the ability to induce proliferation and/or cytokine production (i.e., interferon-γ and/or interleukin-12 production) in T cells, NK cells, B cells and/or macrophages derived from an M tuberculosis-immune individual. See Example 3.

The selection of cell type for use in evaluating an immunogenic response to a antigen will, of course, depend on the desired response. For example, interleukin-12 production is most readily evaluated using preparations containing B-cells and/or macrophages. An M. tuberculosis-immune individual is one who is considered to be resistant to the development of tuberculosis by virtue of having mounted an effective T cell response to M. tuberculosis (i.e., substantially free of disease symptoms). Such individuals can be identified based on a strongly positive (i.e., greater than about 10 mm diameter induration) intradermal skin test response to tuberculosis proteins using a Purified Protein Derivative (PPD) and an absence of any signs or symptoms of tuberculosis disease. T cells, NK cells, B cells and macrophages derived from M. tuberculosis-immune individuals can be prepared using methods known to those of ordinary skill in the art. For example, a preparation of PBMCs (i.e., peripheral blood mononuclear cells) can be employed without further separation of component cells. PBMCs can generally be prepared, for example, using density centrifugation through Ficoll (Winthrop Laboratories, NY). T cells for use in the assays described herein can also be purified directly from PBMCs. Alternatively, an enriched T cell line reactive against mycobacterial proteins, or T cell clones reactive to individual mycobacterial proteins, can be employed. Such T cell clones can be generated by, for example, culturing PBMCs from M. tuberculosis-immune individuals with mycobacterial proteins for a period of 2-4 weeks. This allows expansion of only the mycobacterial protein-specific T cells, resulting in a line composed solely of such cells. These cells can then be cloned and tested with individual proteins, using methods known to those of ordinary skill in the art, to more accurately define individual T cell specificity. In general, antigens that test positive in assays for proliferation and/or cytokine production (i.e., interferon-γ and/or interleukin-12 production) performed using T cells, NK cells, B cells and/or macrophages derived from an M. tuberculosis-immune individual are considered immunogenic. Such assays can be performed, for example, using the representative procedures described below. Immunogenic portions of such antigens can be identified using similar assays, and can be present within the polypeptides described herein.

The ability of a polypeptide (e.g., an immunogenic antigen, or a portion or other variant thereof) to induce cell proliferation can be evaluated by contacting the cells (e.g., T cells and/or NK cells) with the polypeptide and measuring the proliferation of the cells. In general, the amount of polypeptide that is sufficient for evaluation of about $10^5$ cells ranges from about 10 ng/mL to about 100 μg/mL and preferably is about 10 μg/mL. The incubation of polypeptide with cells is typically performed at 37° C. for about six days. Following incubation with polypeptide, the cells are assayed for a proliferative response, which can be evaluated by methods known to those of ordinary skill in the art, such as exposing cells to a pulse of radiolabeled thymidine and measuring the incorporation of label into cellular DNA. In general, a polypeptide that results in at least a three fold increase in proliferation above background (i.e., the proliferation observed for cells cultured without polypeptide) is considered to be able to induce proliferation.

The ability of a polypeptide to stimulate the production of interferon-γ and/or interleukin-12 in cells can be evaluated by contacting the cells with the polypeptide and measuring the level of interferon-γ or interleukin-12 produced by the cells, as demonstrated in Example 3. In general, the amount of polypeptide that is sufficient for the evaluation of about $10^5$ cells ranges from about 10 ng/mL to about 100 μg/mL and preferably is about 10 μg/mL. The polypeptide can, but need not, be immobilized on a solid support, such as a bead or a biodegradable microsphere, such as those described in U.S. Pat. Nos. 4,897,268 and 5,075,109. The incubation of polypeptide with the cells is typically performed at 37° C. for about six days. Following incubation with polypeptide, the cells are assayed for interferon-γ and/or interleukin-12 (or one or more subunits thereof), which can be evaluated by methods known to those of ordinary skill in the art, such as an enzyme-linked immunosorbent assay (ELISA) or, in the case of IL-12 P70 subunit, a bioassay such as an assay measuring proliferation of T cells. In general, a polypeptide that results in the production of at least 50 pg of interferon-γ per mL of cultured supernatant (containing $10^4$-$10^5$ T cells per mL) is considered able to stimulate the production of interferon-γ. A polypeptide that stimulates the production of at least 10 pg/mL of IL-12 P70 subunit, and/or at least 100 pg/mL of IL-12 P40 subunit, per $10^5$ macrophages or B cells (or per $3 \times 10^5$ PBMC) is considered able to stimulate the production of IL-12.

In general, immunogenic antigens are those antigens that stimulate proliferation and/or cytokine production (i.e., interferon-γ and/or interleukin-12 production) in T cells, NK cells, B cells and/or macrophages derived from at least about 25% of M. tuberculosis-immune individuals. Among these immunogenic antigens, polypeptides having superior therapeutic properties can be distinguished based on the magnitude of the responses in the above assays and based on the percentage of individuals for which a response is observed. In addition, antigens having superior therapeutic properties will not stimulate proliferation and/or cytokine production in vitro in cells derived from more than about 25% of individuals who are not M. tuberculosis-immune, thereby eliminating responses that are not specifically due to M. tuberculosis-responsive cells. Those antigens that induce a response in a high percentage of T cell, NK cell, B cell and/or macrophage preparations from M. tuberculosis-immune individuals (with a low incidence of responses in cell preparations from other individuals) have superior therapeutic properties.

Fusion Proteins, Vaccine Compositions, Mode and Manner of Administration

The TB polypeptides of the present invention can be in the form of a conjugate or a fusion protein, which can be manufactured by known methods. In particular, 2 or more of the sequences, SEQ ID NO: 2, 4, 6, 8, 10, 12, 14, 16, 18, 20, 22, 24, 26, 28, 30, 32, 34, 36, 38, 40, 42, 44, 46, or 48 can be fused to one another, or with other proteins, to provide a more effective vaccine composition, and stimulate an improved immunogenic response. Other proteins that can be used to make such a fusion protein include TB antigens that simulate the CD4+ T cell pathway of the immune response. Examples of such antigens include Antigen 85b, ESAT-6, MtB41, Mtb39. The TB polypeptides of the present invention were isolated from MHC class 1 molecules, molecules known for presenting antigens to CD8+ T cells. Although it is possible for these polypeptides to be also presented in the CD4+ pathway, fusing a CD4+ T-cell pathway antigen with one of the polypeptides of the present invention can serve to increase effectiveness of the TB vaccine. Fusion proteins can be manufactured according to known methods of recombinant DNA technology. For example, fusion proteins can be expressed from a nucleic acid molecule comprising sequences which code for a biologically active portion of the TB polypeptides or the entire TB polypeptides set forth in SEQ ID Nos:2, 4, 6, 8, 10, 12, 14, 16, 18, 20, 22, 24, 26, 28, 30, 32, 34, 36, 38, 40, 42, 44, 46, 48 or combinations thereof, and its fusion partner, for example another sequence of the present invention, a portion of an immunoglobulin molecule, or another TB antigen from the CD4+ T cell pathway. For example, some embodiments can be produced by the intersection of a nucleic acid encoding immunoglobulin sequences into a suitable expression vector, phage vector, or other commercially available vectors. The resulting construct can be introduced into a suitable host cell for expression. Upon expression, the fusion proteins can be isolated or purified from a cell by means of an affinity matrix. By measurement of the alternations in the functions of transfected cells occurring as a result of expression of recombinant TB proteins, either the cells themselves or TB proteins produced from the cells can be utilized in a variety of screening assays.

As noted above, in certain aspects the inventive compositions comprise fusion proteins or DNA fusion molecules. Each fusion protein comprises a first and a second inventive polypeptide or, alternatively, a polypeptide of the present invention and a known *M. tuberculosis* antigen, together with variants of such fusion proteins. The fusion proteins of the present invention can also include a linker peptide between the first and second polypeptides. The DNA fusion molecules of the present invention comprise a first and a second isolated DNA molecule, each isolated DNA molecule encoding either an inventive *M. tuberculosis* antigen or a known *M. tuberculosis* antigen.

A DNA sequence encoding a fusion protein of the present invention is constructed using known recombinant DNA techniques to assemble separate DNA sequences encoding the first and second polypeptides into an appropriate expression vector, as described in detail below. The 3' end of a DNA sequence encoding the first polypeptide is ligated, with or without a peptide linker, to the 5' end of a DNA sequence encoding the second polypeptide so that the reading frames of the sequences are in phase to permit mRNA translation of the two DNA sequences into a single fusion protein that retains the biological activity of both the first and the second polypeptides.

A peptide linker sequence can be employed to separate the first and the second polypeptides by a distance sufficient to ensure that each polypeptide folds into its secondary and tertiary structures. Such a peptide linker sequence is incorporated into the fusion protein using standard techniques well known in the art. Suitable peptide linker sequences can be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala can also be used in the linker sequence. Amino acid sequences which can be usefully employed as linkers include those disclosed in Maratea et al., Gene 40:39-46, 1985; Murphy et al., Proc. Natl. Acad. Sci. USA 83:8258-8262, 1986; U.S. Pat. No. 4,935,233 and U.S. Pat. No. 4,751,180. The linker sequence can be from 1 to about 50 amino acids in length. Peptide sequences are not required when the first and second polypeptides have non-essential N-terminal amino acid regions that can be used to separate the functional domains and prevent steric interference.

The ligated DNA sequences are operably linked to suitable transcriptional or translational regulatory elements. The regulatory elements responsible for expression of DNA are located only 5' to the DNA sequence encoding the first polypeptides. Similarly, stop codons require to end translation and transcription termination signals are only present 3' to the DNA sequence encoding the second polypeptide.

Efficacy of a vaccine including the isolated sequences of the present invention can be determined based on the ability of the antigen to provide at least about a 50% (e.g., about a 60%, about a 70%, about a 80%, about a 90%, or about a 100%) reduction in bacterial numbers and/or at least about a 40% (e.g., about a 50%, about a 60%, about a 70%, about a 80%, about a 90%, or about a 100%) decrease in mortality following experimental infection in a challenge experiment. Suitable experimental animals include mice, guinea pigs and primates.

The compositions of the present invention are preferably formulated as either pharmaceutical compositions or as vaccines for in the induction of protective immunity against tuberculosis in a patient. A patient can be afflicted with a disease, or can be free of detectable disease and/or infection. In other words, protective immunity can be induced to prevent, reduce the severity of, or treat tuberculosis.

In one embodiment, pharmaceutical compositions of the present invention comprise one or more of the above polypeptides, either present as a mixture or in the form of a fusion protein, and a physiologically acceptable carrier. Similarly, vaccines comprise one or more the above polypeptides and a non-specific immune response enhancer, such as an adjuvant or a liposome (into which the polypeptide is incorporated).

In another embodiment, a pharmaceutical composition and/or vaccine of the present invention can contain one or more of the DNA molecules of the present invention, either present as a mixture or in the form of a DNA fusion molecule, each DNA molecule encoding a polypeptide as described above, such that the polypeptide is generated in situ. In such vaccines, the DNA can be present within any of a variety of delivery systems known to those of ordinary skill in the art, including nucleic acid expression systems, bacterial and viral expression systems. Appropriate nucleic acid expression systems contain the necessary DNA sequences for expression in the patient (such as a suitable promoter and terminating signal). Bacterial delivery systems involve the administration of a bacterium (such as *Bacillus*-Calmette-Guerrin) that expresses an immunogenic portion of the polypeptide on its cell surface. In a preferred embodiment, the DNA can be introduced using a viral expression system (e.g., vaccinia or other pox virus, retrovirus, or adenovirus), which can involve the use of a non-pathogenic (defective), replication competent virus. Techniques for incorporating DNA into such expression systems are well known to those of ordinary skill in the art. The DNA can also be "naked," as described, for example, in Ulmer et al., Science 259:1745-1749, 1993 and reviewed by Cohen, Science 259:1691-1692, 1993. The uptake of naked DNA can be increased by coating the DNA onto biodegradable beads, which are efficiently transported into the cells.

The antigenic TB molecules of the present invention can be administered with or without a carrier. The terms "pharmaceutically acceptable carrier" or a "carrier" refer to any generally acceptable excipient or drug delivery composition that is relatively inert and non-toxic. Exemplary carriers include sterile water, salt solutions (such as Ringer's solution), alcohols, gelatin, talc, viscous paraffin, fatty acid esters, hydroxymethylcellulose, polyvinyl pyrolidone, calcium carbonate, carbohydrates (such as lactose, sucrose, dextrose, mannose, albumin, starch, cellulose, silica gel, polyethylene glycol (PEG), dried skim milk, rice flour, magnesium stearate, and the like. Suitable formulations and additional carriers are described in Remington's Pharmaceutical Sciences, (17$^{th}$ Ed., Mack Pub. Co., Easton, Pa.). Such preparations can be sterilized and, if desired, mixed with auxiliary agents, e.g., lubricants, preservatives, stabilizers, wetting agents, emulsifiers, salts for influencing osmotic pressure, buffers, coloring, preservatives and/or aromatic substances and the like which do not deleteriously react with the active compounds. Typical preservatives can include, potassium sorbate, sodium metabisulfite, methyl paraben, propyl paraben, thimerosal, etc. The compositions can also be combined where desired with other active substances, e.g., enzyme inhibitors, to reduce metabolic degradation. A carrier (e.g., a pharmaceutically acceptable carrier) is preferred, but not necessary to administer the compound.

The composition can be a liquid solution, suspension, emulsion, tablet, pill, capsule, sustained release formulation, or powder. The method of administration can dictate how the composition will be formulated. For example, the composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc.

The antigenic TB molecules used in the invention can be administered intravenously, parenterally, intramuscular, subcutaneously, orally, nasally, topically, by inhalation, by implant, by injection, or by suppository. The composition can be administered in a single dose or in more than one dose over a period of time to confer the desired effect.

The actual effective amounts of compound or drug can vary according to the specific composition being utilized, the mode of administration and the age, weight and condition of the patient. For example, as used herein, an effective amount of the drug is an amount which reduces the number of bacteria. Dosages for a particular individual patient can be determined by one of ordinary skill in the art using conventional considerations, (e.g. by means of an appropriate, conventional pharmacological protocol).

For enteral or mucosal application (including via oral and nasal mucosa), particularly suitable are tablets, liquids, drops, suppositories or capsules. A syrup, elixir or the like can be used wherein a sweetened vehicle is employed. Liposomes, microspheres, and microcapsules are available and can be used.

Pulmonary administration can be accomplished, for example, using any of various delivery devices known in the art such as an inhaler. See. e.g., S. P. Newman (1984) in *Aerosols and the Lung*, Clarke and Davis (eds.), Butterworths, London, England, pp. 197-224; PCT Publication No. WO 92/16192; PCT Publication No. WO 91/08760.

For parenteral application, particularly suitable are injectable, sterile solutions, preferably oily or aqueous solutions, as well as suspensions, emulsions, or implants, including suppositories. In particular, carriers for parenteral administration include aqueous solutions of dextrose, saline, pure water, ethanol, glycerol, propylene glycol, peanut oil, sesame oil, polyoxyethylene-polyoxypropylene block polymers, and the like. Ampules are convenient unit dosages.

Biodegradable microspheres (e.g., polylactic galactide) can also be employed as carriers for the pharmaceutical compositions of this invention. Suitable biodegradable microspheres are disclosed, for example, in U.S. Pat. Nos. 4,897, 268 and 5,075,109.

Any of a variety of adjuvants can be employed in the vaccines of this invention to enhance the immune response. Most adjuvants contain a substance designed to protect the antigen from rapid catabolism, such as aluminum hydroxide or mineral oil, and a nonspecific stimulator of immune responses, such as lipid A, Bortadella pertussis or *Mycobacterium tuberculosis*. Suitable adjuvants are commercially available and include, for example, Freund's Incomplete Adjuvant and Freund's Complete Adjuvant (Difco Laboratories) and Merck Adjuvant 65 (Merck and Company, Inc., Rahway, N.J.). Other suitable adjuvants include alum, biodegradable microspheres, monophosphoryl lipid A and quil A.

In the inventive vaccines, it is preferred that the adjuvant induces an immune response comprising Th1 aspects. Suitable adjuvant systems include, for example, a combination of monophosphoryl lipid A, preferably 3-de-O-acylated monophosphoryl lipid A (3D-MLP) together with an aluminum salt. An enhanced system involves the combination of a monophosphoryl lipid A and a saponin derivative, particularly the combination of 3D-MLP and the saponin QS21 as disclosed in WO 94/00153, or a less reactogenic composition where the QS21 is quenched with cholesterol as disclosed in WO 96/33739. Previous experiments have demonstrated a clear synergistic effect of combinations of 3D-MLP and QS21 in the induction of both humoral and Th1 type cellular immune responses. A particularly potent adjuvant formation involving QS21, 3D-MLP and tocopherol in an oil-in-water emulsion is described in WO 95/17210 and is a preferred formulation.

The administration of the antigenic TB polypeptide molecules of the present invention and other compounds can occur simultaneously or sequentially in time. A DNA vaccine and/or pharmaceutical composition as described above can be administered simultaneously with or sequentially to an additional polypeptide of the present invention, a known *M. tuberculosis* antigen, an immune enhancer, or other compound known in the art that would be administered with such a vaccine. The compound can be administered before, after or at the same time as the antigenic TB molecules. Thus, the term "co-administration" is used herein to mean that the antigenic TB molecules and the additional compound (e.g., immune stimulating compound) will be administered at times to achieve a specific TB immune response, as described herein. The methods of the present invention are not limited to the sequence in which the compounds are administered, so long as the compound is administered close enough in time to produce the desired effect.

Routes and frequency of administration of the inventive pharmaceutical compositions and vaccines, as well as dosage, will vary from individual to individual and can parallel those currently being used in immunization using BCG. In general, the pharmaceutical compositions and vaccines can be administered by injection (e.g., intracutaneous, intramuscular, intravenous or subcutaneous), intranasally (e.g., by aspiration), intralung, or orally. Between 1 and 3 doses can be administered for a 1-36 week period. Preferably, 3 doses are administered, at intervals of 3-4 months, and booster vaccinations can be given periodically thereafter. Alternate protocols can be appropriate for individual patients. A suitable dose is an amount of polypeptide or DNA that, when administered as described above, is capable of raising an immune response in an immunized patient sufficient to protect the patient from *M. tuberculosis* infection for at least 1-2 years. In general, the amount of polypeptide present in a dose (or produced in situ by the DNA in a dose) ranges from about 1 pg to about 100 mg per kg of host, typically from about 10 pg to about 1 mg, and preferably from about 100 pg to about 1 μg. Suitable dose sizes will vary with the size of the patient, but will typically range from about 0.1 mL to about 5 mL.

EXEMPLIFICATION

Example 1

*M. tuberculosis* Peptides Associated With MHC Class 1 Molecules

A strategy to detect *M. tuberculosis* peptides associated with MHC Class I molecules of mouse macrophages infected in vivo was applied to identify the microbial antigens.

The rationale to search for *M. tuberculosis* antigens or peptides associated with the MHC class I molecules of infected cells is based on the fact that these host cell molecules are crucial to present antigens to CD8+ T cells, a subset of T cells involved in resistance and against tuberculosis. Therefore, this approach of antigen discovery has direct implication in vaccine development strategies against this disease.

The MHC class I-associated *M. tuberculosis* peptides were isolated from adherent spleen cells of C57BL/6 mice infected with 107 CFU of *M. tuberculosis*. C57BL/6 mice are considered to be relatively resistant to *M. tuberculosis* infection, therefore ideal for these studies. The infection with a high inoculum is important to achieve high degree of intra cellular infection in the animals' spleen cells. Between days 10 and 14 of infection the mice spleens contain approximately five times more cells than non-infected controls. A great percentage of the spleen cells are macrophages infected with *M. tuberculosis*. The mice were sacrificed and their splenic adherent cells were obtained, lysed with CHAPS detergent (Boehringer Mannheim Corp., Indianapolis, Ind.), and the MHC class I molecules isolated by affinity purification on a protein G sepharose column linked to the anti-H-2 K/$D^b$ monoclonal antibody (ATCC HB-11). The procedure is summarized in FIG. 3.

The eluted peptides comprising a mixture of molecules below 5 kDa were ultra filtrated over a Millipore Ultrafree-CL 5 kDa cutoff were then fractionated by microbore reverse phase HPLC (Delta-Pak C18 column, 300 Å pore size, 5μ particle). The HPLC profiles rendered several peaks, which were individually analyzed by microcapillary liquid chromatography coupled with electrospray ionization mass spectrometry (LC-MS) to determine the molecular weight and abundance of all peptide species. The mass of the candidate peptides was then obtained by collision activated dissociation (CAD) tandem mass spectra (MS/MS).

The peptide sequences were searched for identity with known proteins in both the *M. tuberculosis* and mouse genome databases (The Institute for Genomic Research). Several peptides had strong homology with mouse protein. However seven peptide and nucleic acid sequences were identified to being of *M. tuberculosis* origin (FIG. 1). The corresponding genes encoding the protein donor of these peptides are being cloned and will be expressed using standard procedures. In addition, bacterial plasmid DNA containing these *M. tuberculosis* genes will be prepared. Both, recombinant protein and plasmid DNA will be used in immunization protocols aiming to investigate the protection potential of these molecules to protect mice against challenge with virulent *M. tuberculosis*. The protein formulation will the used to test CD4+ response and the DNA immunization will target CD8+ T cell response.

Example 2

A *M. tuberculosis* Antigen Found in the Urine of Infected Mice

A strategy to detect *M. tuberculosis* antigens in the urine of infected mice was applied to identify the microbial antigens in the urine of patients with active tuberculosis.

Antigen detection assays, in contrast to conventional serology, detect disease status and not the host antibody response to the disease etiological agent. It can therefore be used for both diagnosis and treatment follow up. In the present project an antigen discovery approach to identify *M. tuberculosis* antigens in the urine of human patients was used. Additionally, recombinant proteins will be produced and validated as markers of active disease.

Individual urines (15 mL) were loaded onto a 15 mL capacity Vivaspin 5K MWCO filtered and centrifuged at 3000 G at 4° C. until the retentate volume was <2 mL. The concentrate was removed from the membrane by rinsing with 6M urea 100 mM ammonium bicarbonate. Final concentrates were brought up to 4 mL with 6M Urea 100 mM ammonium bicarbonate pH 8.5. To each protein concentrate sample was added 20 mL of 2M DTT. Samples were vortexed and incubated at 37° C. for 1 hour. Reduced cysteines were alkylated by adding 200 mL of 0.5M iodoacetamide to each sample. Samples were vortexed and allowed to react for 1 hour at room temperature in the dark. Residual iodoacetamide was quenched with 15 mL of 2M DTT. From the 4 mL stock sample, 300 uL was removed for gel analysis.

Gels were imaged with a Kodak DC280 Digital Camera fitted with a +10 Macro lens. Images were processed using Adobe Photoshop and printed out. Gels were cut with a clean razor blade into 33 gel slices each while marking positions of the cuts for each slice. Slices were then placed into 2 mL centrifuge tubes. All further processing of the samplers was perfomed in a dual isolation BioSafety Cabinet. The tubes with gel slices were filled to 2 mL with 50% methanol, 5% acetic acid, and rinsed three times with additional aliquots of 50% methanol, 5% acetic acid. The destain solution was removed and the tubes filled with 2 mL of acetonitrile. After 30 minutes with agitation, the acetonitrile was removed and replaced with 100 mM ammonium bicarbonate. After 30 minutes the ammonium bicarbonate solution was removed and the tubes were filled with acetonitrile. This acetonitrile, ammonium bicarbonate rinsing step was repeated once. The final acetonitrile wash was removed just prior to digestion and the gel slices dried for 30 minutes in a speedvac. The tubes containing the dried gel slices were placed on ice and allowed to cool. Promega Sequencing grade trypsin was dissolved in ice cold 50 mM ammonium bicarbonate to a concentration of 13.3 mg/mL. Using a repeating pipettor, 125 mL of the trypsin solution was added to the bottom of each tube. The gel slices were allowed to swell for 15 minutes on ice, after which an additional 125 mL of 50 mM ammonium bicarbonate was added to each tube. The tubes were then capped and incubated for 16 hours at 37° C. After digestion 650 mL of 50 mM ammonium bicarbonate was added to each tube. The samples were then incubated for 1 hour at 37° C. The first set of extracts were removed and placed into labeled Axygen 1.5 mL tubes, a second extraction of 650 mL ammonium bicarbonate was carried out and pooled with the first. These extracts were then lyophilized while two acidic extractions of 650 mL of 50% acetonitrile 0.1% formic acid were carried out. All extracts were frozen to −80° C. and lyophilized to dryness in a ThermoSavant SC280 speedvac <10 mTorr. The lyophilate was redissolved into 200 mL of 5% acetonitrile 0.1% formic acid. Appropriate volumes of each extract (1-6, 10 mL)(7-12, 20 mL) (13-18, 35 mL) (19-23, 50 mL) were added to a 96 well plate to approximate protein molarity load and protein from each MW region of the gel, the plate was frozen to −80° C. and lyophilized again. All samples were redissolved in 12 mL of 5% acetonitrile 0.1% formic acid.

Samples were then evaluated by Mass Spectrometry on a LCQ DECA XP plus Proteome X workstation from Thermofinnigan. For each run 10 mL of each reconstituted sample were injected with a Famos Autosampler while the separation was done on a 75 mm i.d.×18 cm column packed with C18 media running at a 235 nL a minute flow rate provided from a Surveyor MS pump with a flow splitter with a gradient of 5-60% water 0.1% formic acid, acetonitrile 0.1% formic acid over the course of 90 min. (2.5 hour run), 180 minutes (4 hour run), or 400 minutes (8 hour run). In between each set of samples was run two standards of a 5 Angio mix peptides (Michrom BioResources) to ascertain column performance, and observe any potential carryover that might have occurred. The LCQ was run in a top five configuration with one MS scans and five MS/MS scans. Dynamic exclusion was set to 1 with a limit of 30 seconds. Peptide ID's were made using Sequest through the Bioworks Browser 3.1. Sequential database searches was made using the NCBI RefSeqHuman Database using differential carbamidomethyl modified cysteines and oxidized methionines, followed by further searches using differential modifications. Secondary searches were performed using Sequest using RefSeqHuman Gnomon predicted protein database. In this fashion known and theoretical protein hits can be found without compromising the statistical relevance of all the data. Peptide score cutoff values were chosen at Xcorr of 1.8 for singly charged ions, 2.5 for doubly charged ions, and 3.0 for triply charged ions, along with deltaCN values of 0.1, and RSP values of 1. The cross correlation values chosen for each peptide assure a high confidence match for the different charge states, while the deltaCN cutoff insures the uniqueness of the peptide hit. The RSP value of 1 ensured that the peptide matched the top hit in the preliminary scoring and that the peptide fragment file only matched to one protein hit. Using this state of art approach several human peptides were identified but most importantly we were able thus far to identify at least five M. tuberculosis peptides in the urine of three out of the six urine samples studied. One of the sequences of the identified peptide (MVIIELMRR—SEQ ID NO: 30) has identical homology with the deduced sequence of a M. tuberculosis protein (FIG. 2) [The Institute for Genomic Research (TIGR), and SWISS-PROT/TrEMBL AC # O33183]. Four other sequences were identified, SEQ ID NO: 34, 38, 42, 46, shown in FIGS. 5-9, respectively. These peptide sequence was found in three out of six urine samples from tuberculosis patients. PCR primers were designed and synthesized and used to amplify the full-length gene encoding this protein from M. tuberculosis genomic DNA. A DNA fragment (~1 kb) containing at the 5' end an Nde I site and at the 3' end a Bam HI site, was obtained and is currently been used to clone and expressed the gene.

Example 3

Production, Purification and Characterization of M. tuberculosis Recombinant Proteins Concentrated efforts have been made to produce, purify, and characterize the proteins of *M. tuberculosis* found in the urine of patients with pulmonary tuberculosis, as described herein. Three of them (MTP1694 (SEQ ID NO: 42), MTP2462 (SEQ ID NO: 46)) and (MT2990 (SEQ ID NO: 38)) have been obtained and their biochemical and biological properties characterized. The three proteins were purified from inclusion bodies with yields ranging from 10 to 15 mg of purified protein per liter of induced culture. FIG. 10 illustrates the over-expression of the recombinant molecules, MT1694, MT2462, and MT2990, in *E. coli* and shows that they migrated to positions in the gel that correspond to their expected Molecular Weight (MW). Recombinant proteins were expressed in *E. coli* BL-21(DE3)/pLysS host cells with six His-tag amino terminal residues. Proteins were purified by affinity chromatography using Ni-NTA agarose matrix. Purity was evaluated by SDS-PAGE (4-20% gradient polyacrylamide gel) followed by Coomassie blue stain. Because the MT2990 gene codes for a protein of 130.6 kDa MW, which is a molecule size that is difficult to express as recombinant protein, overlapping/truncated forms of this molecule were cloned and expressed. The cloned and expressed protein illustrated in FIG. 10 represents a fragment of the full length gene that spans 100 amino acids, both upstream and downstream of the amino acid sequence of the M tuberculosis protein (MT2990) that has identical homology with the peptide found in the urine of tuberculosis patients. This fragment of the molecule was chosen because this portion of the protein it is stable and resistant to the host proteolytic enzyme machinery, therefore a vaccine target.

Rabbit antisera to MTP1694 and MTP2462 recombinant proteins were produced and an antiserum to MT2990 is being and can be generated. The antisera to MTP1694 and MTP2462 were used to validate identified proteins as a genuine *M. tuberculosis* molecules, which was carried out by Western blot analyses using a crude antigenic preparations of *M. tuberculosis* antigen (whole bacterial cell extract) as well as culture filtrate (CF) or CF antigens (supplied by the Dept. Microbiol. Immunol. Pathol., Colorado State University, Fort Collins Colo.). Antigens were electrophoresed under reducing conditions in a 4-20% gradient gel and transferred to nitrocellulose membrane followed by probing with either rabbit anti-MTB1694 or anti-MT2462 antisera. Reactivity was detected with peroxidase labeled goat-anti-rabbit immunoglobulin and developed using a chemiluminescent reagent (ECL). FIG. 11 indicates that the anti-MTP1694 antiserum recognizes a band of ~37 kDa in both the mycobacterial lysate and culture filtrate preparations (lanes 1 and 2) as well as, as expected, the recombinant protein (lane 3). In contrast, the anti-MTP2462 antiserum recognizes a band of ~27 kDa in only in the bacterial lysate and not in the culture filtrate. The MW bands of both antigens match their predicted MW. In addition, the MW of the recombinant molecules are slightly higher than the native molecules, which is expected because the recombinant molecules have, in addition to the sequences of the native molecules, a stretch of 16 amino acids derived from the cloning vector (a tag of six histidines to facilitate purification and a thrombin site composed of 10 amino acids to allow cleavage of the his-tag). These results therefore confirm that both MTP1694 and MTP2462 are genuine *M. tuberculosis* proteins that are actively produced during the bacterial growth. In addition, because the antigen MTP1694 is present in the culture filtrate preparation ("*M. tuberculosis* secrete protein") these results demonstrate this molecule to be useful as a vaccine.

To evaluate the use of the identified antigens as vaccine targets for humans, the response of peripheral blood mononuclear cells (PBMC) obtained from healthy PPD (an intradermal skin test response to tuberculosis proteins using a Purified Protein Derivative) positive donors to these antigens was analyzed. Thus far, four healthy PPD positive and one PPD negative donors have been tested with the antigens MTP1694 and MTP2462. The recombinant protein (MT299) mentioned above, had not been available at the time that these assays were performed. To test for the antigen recognition, both antigen induced proliferative response and production of IFN-γ were used, following stimulation with recombinant antigens (5 ug/ml). Proliferation was measured by [3H]TdR incorporation and results are expressed as counts per minute (CPM). IFN-γ was measured by sandwich ELISA in the culture supernatants. The results are expressed in FIGS. 12A and B and indicate that both antigens are readily recognized by PBMC of three out the four PPD positive donors. No response was observed with the PBMC obtained from the PPD negative donor. These results suggest that these antigens will be recognized by a high percentage of the healthy PPD positive individuals (presumably resistant). In addition, because the proliferative response was accompanied by the production of IFN-γ, MT1649 and MT2462 is associated with protection against tuberculosis, therefore these molecules are vaccine targets.

The relevant teachings of all the references, patents and/or patent applications cited herein are incorporated herein by reference in their entirety.

The teachings of the following patents are incorporated herein by reference in their entirety: U.S. Pat. No. 6,627,198, entitled, "Fusion proteins of *Mycobacterium tuberculosis* antigens and their uses;" U.S. Pat. No. 6,613,881, entitled, "Compounds for immunotherapy and diagnosis of tuberculosis and methods of their use;" "U.S. Pat. No. 6,592,877, entitled, "Compounds and methods for immunotherapy and diagnosis of tuberculosis;" "U.S. Pat. No. 6,555,653, entitled, "Compounds for diagnosis of tuberculosis and methods of their uses;"U.S. Pat. No. 6,544,522, entitled, "Fusion proteins of *Mycobacterium tuberculosis* antigens and their uses;"U.S. Pat. No. 6,458,366, entitled, "Compounds and methods for diagnosis of tuberculosis;""U.S. Pat. No. 6,338,852 entitled, "Compounds and methods for diagnosis of tuberculosis;" and "U.S. Pat. No. 6,290,969, entitled, "Compounds and methods for immunotherapy and diagnosis of tuberculosis."

While this invention has been particularly shown and described with references to preferred embodiments thereof, it will be understood by those skilled in the art that various changes in form and details can be made therein without departing from the scope of the invention encompassed by the appended claims.

What is claimed is:

1. An isolated nucleic acid molecule, vector or plasmid, wherein the nucleic acid molecule, vector or plasmid consists of a sequence that encodes a polypeptide molecule that consists of an immunogenic portion of a *M. tuberculosis* antigen, wherein said antigen is encoded by a nucleic acid sequence consisting of:
   a) SEQ ID NO: 1, 3, 5, 7, 9, 11, 13, 15, 17, 19, 21, 23, 25, 27, 29, 31, 33, 35, 37, 39, 41, 43, 45, 47, or combination thereof;
   b) the coding region of SEQ ID NO:1, 3, 5, 7, 9, 11, 13, 15, 17, 19, 21, 23, 25, 27, 29, 31, 33, 35, 37, 39, 41, 43, 45, 47, or combination thereof;
   c) a complement of SEQ ID NO: 1, 3, 5, 7, 9, 11, 13, 15, 17, 19, 21, 23, 25, 27, 29, 31, 33, 35, 37, 39, 41, 43, 45, 47, or combination thereof;
   d) a sequence that hybridizes to SEQ ID NO:1, 3, 5, 7, 9, 11, 13, 15, 17, 19, 21, 23, 25, 27, 29, 31, 33, 35, 37, 39, 41, 43, 45, 47, or combination thereof under high stringency conditions, wherein said conditions comprise 1XSSC, 1% SDS and 0.1-2 mg/ml denatured calf thymus DNA at 65° C.; or
   e) a sequence that encodes SEQ ID NO: 2, 4, 6, 8, 10, 12, 14, 16, 18, 20, 22, 24, 26, 28, 30, 32, 34, 36, 38, 40, 42, 44, 46, 48 or combination thereof.

2. The isolated nucleic acid molecule of claim 1, wherein the isolated nucleic acid molecule encodes a polypeptide molecule that stimulates an immunogenic specific TB response in a host.

3. The isolated nucleic acid molecule of claim 1, wherein the nucleic acid molecule is an RNA molecule.

4. An isolated nucleic acid molecule, vector or plasmid, wherein the nucleic acid molecule, vector or plasmid consists of a sequence that encodes a polypeptide molecule that consists of a *M. tuberculosis* antigen, wherein said antigen is encoded by a nucleic acid sequence having greater than or equal to about 70% identity with a sequence consisting of:
   a) SEQ ID NO: 1, 3, 5, 7, 9, 11, 13, 15, 17, 19, 21, 23, 25, 27, 29, 31, 33, 35, 37, 39, 41, 43, 45, 47, or combination thereof;
   b) the coding region of SEQ ID NO: 1, 3, 5, 7, 9, 11, 13, 15, 17, 19, 21, 23, 25, 27, 29, 31, 33, 35, 37, 39, 41, 43, 45, 47, or combination thereof;
   c) a complement of SEQ ID NO: 1, 3, 5, 7, 9, 11, 13, 15, 17, 19, 21, 23, 25, 27, 29, 31, 33, 35, 37, 39, 41, 43, 45, 47, or combination thereof;
   d) a sequence that hybridizes to SEQ ID NO: 1, 3, 5, 7, 9, 11, 13, 15, 17, 19, 21, 23, 25, 27, 29, 31, 33, 35, 37, 39, 41, 43, 45, 47, or combination thereof under high stringency conditions, wherein said conditions comprise 1XSSC, 1% SDS and 0.1-2 mg/ml denatured calf thymus DNA at 65° C.; or e) a sequence that encodes SEQ ID NO: 2, 4, 6, 8, 10, 12, 14, 16, 18, 20, 22, 24, 26, 28, 30, 32, 34, 36, 38, 40, 42, 44, 46, 48, or combination thereof.

5. The isolated nucleic acid molecule of claim 4, wherein the nucleic acid molecule has greater than or equal to about 80% identity with said sequences.

6. The isolated nucleic acid molecule of claim 5, wherein the nucleic acid molecule has greater than or equal to about 90% identity with said sequences.

7. A host cell transformed with the nucleic acid sequence of claim 1.

8. A kit that comprises:
a) one or more nucleic acid molecules of claim 1; and
b) a detection reagent.

9. A composition that comprises the nucleic acid molecule of claim 1 and a physiologically acceptable carrier.

10. The composition of claim 9, further including an immune response enhancer.

11. The composition of claim 10, wherein the immune response enhancer is an adjuvant or another TB antigen.

12. The composition of claim 11, wherein the adjuvant includes at least one component of 3D-MPL or QS21.

13. The composition of claim 9, wherein the composition is formulated in an oil in water emulsion.

14. The composition of claim 10, wherein the immune response enhancer is an immunostimulatory cytokine or chemokine.

15. The kit of claim 8, wherein the nucleic acid molecules are immobilized on a solid support.

16. The kit of claim 8, wherein the detection reagent comprises a reporter group conjugated to a binding agent.

17. The kit of claim 16, wherein the binding agent is an anti-immunoglobulin, Protein G, Protein A or a lectin.

18. The kit of claim 16, wherein the reporter group is a radioisotope, a fluorescent group, a luminescent group, an enzyme, biotin or a dye particle.

* * * * *